US009957535B2

(12) United States Patent
Conradie et al.

(10) Patent No.: US 9,957,535 B2
(45) Date of Patent: *May 1, 2018

(54) METHODS, REAGENTS AND CELLS FOR BIOSYNTHESIZING COMPOUNDS

(71) Applicant: INVISTA North America S.á r.l., Wilmington, DE (US)

(72) Inventors: Alex Van Eck Conradie, Eaglescliffe (GB); Adriana Leonora Botes, Rosedale East (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/741,342

(22) Filed: Jun. 16, 2015

(65) Prior Publication Data
US 2015/0361468 A1    Dec. 17, 2015

Related U.S. Application Data

(60) Provisional application No. 62/012,592, filed on Jun. 16, 2014.

(51) Int. Cl.
| C12P 13/00 | (2006.01) |
| C12P 7/44 | (2006.01) |
| C12P 7/42 | (2006.01) |
| C12P 7/18 | (2006.01) |
| C12N 9/02 | (2006.01) |
| C12N 9/10 | (2006.01) |
| C08G 69/26 | (2006.01) |
| C12P 7/62 | (2006.01) |
| C12P 7/40 | (2006.01) |
| C12N 15/52 | (2006.01) |
| C12P 13/04 | (2006.01) |
| C12N 9/00 | (2006.01) |

(52) U.S. Cl.
CPC ............ *C12P 13/001* (2013.01); *C08G 69/26* (2013.01); *C12N 9/0008* (2013.01); *C12N 9/1096* (2013.01); *C12N 15/52* (2013.01); *C12P 7/18* (2013.01); *C12P 7/40* (2013.01); *C12P 7/42* (2013.01); *C12P 7/44* (2013.01); *C12P 7/62* (2013.01); *C12Y 102/99006* (2013.01); *C12Y 206/01018* (2013.01); *C12N 9/00* (2013.01); *C12P 13/04* (2013.01)

(58) Field of Classification Search
CPC ........... C12P 7/62; C12P 13/04; C12P 13/001; C12N 9/00; C07C 69/42
See application file for complete search history.

(56) References Cited

U.S. PATENT DOCUMENTS

| 2,439,513 A | 4/1948 | Hamblet et al. |
| 2,557,282 A | 6/1951 | Hamblet et al. |
| 2,791,566 A | 5/1957 | Jeffers |
| 2,840,607 A | 6/1958 | Attane, Jr. et al. |
| 2,971,010 A | 2/1961 | Gilby, Jr. et al. |
| 3,023,238 A | 2/1962 | Chapman et al. |
| 3,338,959 A | 8/1967 | Sciance et al. |
| 3,365,490 A | 1/1968 | Arthur et al. |
| 3,515,751 A | 6/1970 | Oberster |
| 3,719,561 A | 3/1973 | Tanaka et al. |
| 4,058,555 A | 11/1977 | Mims |
| 6,255,451 B1 | 7/2001 | Koch et al. |
| 6,372,939 B1 | 4/2002 | Bunnel et al. |
| 8,088,607 B2 | 1/2012 | Buggard et al. |
| 8,361,769 B1 | 1/2013 | Koch et al. |
| 2004/0054235 A1 | 3/2004 | Fodor et al. |
| 2010/0035309 A1 | 2/2010 | Havemen et al. |
| 2010/0151536 A1 | 6/2010 | Baynes et al. |
| 2010/0203600 A1 | 8/2010 | Dubois |
| 2010/0298612 A1 | 11/2010 | Behrouzian et al. |
| 2010/0317069 A1 | 12/2010 | Burk et al. |
| 2011/0171699 A1 | 7/2011 | Raemakers-Franken et al. |
| 2011/0256599 A1 | 10/2011 | Hu et al. |
| 2012/0064252 A1 | 3/2012 | Beatty |
| 2012/0101009 A1 | 4/2012 | Beatty |
| 2012/0301950 A1* | 11/2012 | Baynes .................. C12N 15/52 435/252.3 |
| 2013/0065279 A1 | 3/2013 | Burk et al. |
| 2013/0183728 A1 | 7/2013 | Botes |
| 2013/0210090 A1 | 8/2013 | Pearlman et al. |
| 2013/0217081 A1 | 8/2013 | Pearlman et al. |
| 2013/0224807 A1 | 8/2013 | Pearlman et al. |
| 2013/0267012 A1 | 10/2013 | Steen et al. |

(Continued)

FOREIGN PATENT DOCUMENTS

| EP | 2647718 | 10/2013 |
| WO | WO 2008/006037 | 1/2008 |

(Continued)

OTHER PUBLICATIONS

International Search Report and Written Opinion in International Application No. PCT/US2015/036074, dated Sep. 9, 2015, 14 pages.
Invitation to Pay Fees in International Application No. PCT/US2015/036086, dated Sep. 16, 2015, 7 pages.
"Enterococcus faecalis V583 bifuntional acetaldehyde-CoA/Alcohol Dehydrogenase," biocyc.org, retrieved on Jun. 19, 2014, http://biocyc.org/EFAE226185/N_EW-IMAGE?type=ENZYME&object=GH11-877-MONOMER, 9 pages.
"Information on EC 1.2.1.57—butanal dehydrogenase," brenda-enzymes.org retrieved on Jun. 19, 2014, http://www.brenda-enzymes.org/php/result_flat.php4?ecno=1.2.1.57, 6 pages.
"Brenda—The comprehensive Enzyme Information System," Jul. 2011, retrieved on Sep. 19, 2014, http://web.archive.org/web/20111009205602/http://www.brenda-enzymes.org/, 1 page.

(Continued)

*Primary Examiner* — Gregory Listvoyb
(74) *Attorney, Agent, or Firm* — William J. Simmons; Thomas H. Jenkins

(57) ABSTRACT

This document describes biochemical pathways for producing glutaric acid, 5-aminopentanoic acid, 5-hydroxypentanoic acid, cadaverine or 1,5-pentanediol by forming one or two terminal functional groups, comprised of carboxyl, amine or hydroxyl group, in a C5 backbone substrate such as 2-oxoglutarate.

21 Claims, 30 Drawing Sheets

(56) References Cited

U.S. PATENT DOCUMENTS

| | | | |
|---|---|---|---|
| 2014/0186902 A1 | 7/2014 | Botes et al. |
| 2014/0186904 A1 | 7/2014 | Botes et al. |
| 2014/0193861 A1 | 7/2014 | Botes et al. |
| 2014/0193862 A1 | 7/2014 | Botes et al. |
| 2014/0193863 A1 | 7/2014 | Botes et al. |
| 2014/0193864 A1 | 7/2014 | Botes et al. |
| 2014/0193865 A1 | 7/2014 | Botes et al. |
| 2014/0196904 A1 | 7/2014 | Fontenelle et al. |
| 2014/0199737 A1 | 7/2014 | Botes et al. |
| 2014/0248673 A1 | 9/2014 | Botes et al. |
| 2015/0111262 A1 | 4/2015 | Botes et al. |
| 2015/0267211 A1 | 9/2015 | Botes et al. |

FOREIGN PATENT DOCUMENTS

| | | |
|---|---|---|
| WO | WO 2008/145737 | 12/2008 |
| WO | WO 2009/121066 | 1/2009 |
| WO | WO 2009/113853 | 9/2009 |
| WO | WO 2009/113855 | 9/2009 |
| WO | WO 2009/140159 | 11/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/028519 | 2/2013 |
| WO | WO 2013/082542 | 6/2013 |
| WO | WO 2013/090837 | 6/2013 |
| WO | WO 2013/096898 | 6/2013 |
| WO | WO 2014/031724 | 2/2014 |
| WO | WO 2014/093865 | 6/2014 |
| WO | WO 2014/105788 | 7/2014 |
| WO | WO 2014/105793 | 7/2014 |

OTHER PUBLICATIONS

Aimin et al., "*Nocardia* sp. carboxylic acid reductase: cloning, expression, and characterization of a new aldehyde oxidoreductase family," Appl. Environ. Microbiol., 2004, 70:1874-1881.
Akita et al., "Highly stable meso-diaminopimelate dehydrogenase from an Ureibacillus thermosphaericus strain A1 isolated from a Japanese compost: purification, characterization and sequencing," AMB Express, 2011, 1:43, 8 pages.
Alber et al., "Malonyl-coenzyme A reductase in the modified 3-hydroxypropionate cycle for autotrophic carbon fixation in archaeal Metallosphaera and Sulfolobus spp," J. Bacteriology, 2006, 188:8551-8559.
Aloulou et al., "Purification and biochemical characterization of the LIP2 lipase from Yarrowia lipolytica," Biochim. Biophys. Acta, 2007, 1771:228-237.
Anton et al., Polyamides, Fibers, Encyclopedia of Polymer Science and Engineering, 2001, 11:409-445.
Atsumi et al., "Acetolactate synthase from *Bacillus subtilis* serves as a 2-ketoisovalerate decarboxylase from isobutanol synthesis in *Escherichi coli*," Applied and Environ. Microbiol., 2009, 75(19):6306-6311.
Aursnes et al., "Total Synthesis of the Lipid Mediator PD1(n-3 DPA): Configurational Assignments and Anti-Inflammatory and Pro-resolving Actions," Journal of Natural Products, Feb. 2014, 77:910-916.
Azuma et al., "Naphthalene—a constituent of Magnolia flowers," Phytochemistry, 1996, 42:999-1004.
Barker et al., "Enzymatic reactions in the degradation of 5-aminovalerate by Clostridium aminovalercum," J Biol Chem., 1987, 262(19):8994-9003.
Becker et al., "Metabolic flux engineering of L-lysine production in Corynebacterium glutamicum—over expression and modification of G6P dehydrogenase," J Biotechnol. 2007, 132(2):99-109.
Bellmann et al., "Expression control and specificity of the basic amino acid exporter LysE of Corynebacterium glutamicum," Microbiology 2001, 147:1765-1774.
Bennett et al., "Purification and properties of ε-caprolactone hydrolases from Acinetobacter NCIB 9871 and Nocardia globevula CL1," Journal of General Microbiology, 1988 134: 161-168.
Bergler et al., "Protein EnvM is the NADH-dependent enoyl-ACP reductase (FabI) of *Escherichia coli*," J. Bio Chem, 1993, 269(8):5493-5496.
Bernstein et al., "Transfer of the high-GC cyclohexane carboxylate degradation pathway from Rhodopseudomonas palustris to *Escherichia coli* for production of biotin," Metabolic Engineering, May 2008, 10(3-4):131-140.
Berthold et al., "Structure of the branched-chain keto acid decarboxylase (KdcA) from Lactococcus lactis provides insights into the structural basis for the chemoselective and enantioselective carboligation reaction," Acta Crystallographica Sec. D, 2007, D63:1217-1224.
Binieda et al., "Purification, characterization, DNA Sequence and cloning of a pimeloyl-CoA synthetase from Pseudomonas medocin 35," Biochem J., 1999, 340:793-801.
Bond-Watts et al., "Biochemical and Structural Characterization of the trans-Enoly-CoA Reductase from Treponema denticola," Biochemistry, 2012, 51:6827-6837.
Bordeaux et al., "Catalytic, Mild, and Selective Oxyfunctionalization of Linear Alkanes: Current challenges," Angew. Chem. Int. Ed., 2012, 51:10712-10723.
Bordes et al., "Isolation of a thermostable variant of Lip2 lipase from Yarrowia lipolytica by directed evolution and deeper insight into the denaturation mechanisms," Journal of Biotechnology, 2011, 156: 117-124.
Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.
Boylan et al., "Functional identification of the fatty acid reductase components encoded in the luminescence operon of Vibrio fischeri," Journal of Bacteriology, 1985, 163(3):1186-1190.
Boylan et al., "Lux C, D and E genes of the Vibrio fischeri luminescence operon code for the reductase, transferase, and synthetase enzymes involved in aldehyde biosynthesis," Photochemistry and photobiology, 1989, 49:681-688.
Bramer et al., "The methylcitric acid pathway in Ralstonia eutropha: new genes identified involved in propionate metabolism," Microbiology 2001, 147:2203-2214.
Breithaupt et al., "Crystal structure of 12-oxophytodienoate reductase 3 from tomato: self-inhibition by dimerization," Proc Natl. Acad Sci. USA, 2006, 103:14337-14342.
Brigham et al., "Engineering Ralstonia eutropha for Production of Isobutanol from CO2, H2, and O2," Advanced Biofuels and Bioproducts 2013, Chapter 39, pp. 1065-1090.
Brzostowicz et al., "mRNA differential display in a microbial enrichment culture: simultaneous identification of three cyclohexanonemonooxygenases from three species," Applied and Environmental Microbiology, 2003, 69: 334-342.
Brzostowicz et al., "Identification of two gene clusters involved in cyclohexanone oxidation in Brevibacterium epidermidis strain HCU," Applied and Microbiological Biotechnology, 2002, 58:781-789.
Buckel et al., "Glutaconate CoA-transferase from Acidaminococcus fermentans," Eur J. Biochem, 1981, 118:315-321.
Budde et al., "Roles of Multiple Acetoacetyl Coenzyme a Reductases in Polyhydroxybutyrate Biosynthesis in Ralstonis eutropha H16," J Bacteriol. 2010, 192(20):5319-5328.

(56) References Cited

OTHER PUBLICATIONS

Bugg et al., "The emerging role for bacteria in lignin degradation and bio-product formation," Curr Opin Biotechnol 2011, 22(3):394-400.

Buhler et al., "Occurrence and the possible physiological role of 2-enoate reductases," FEBS Letters, 1980, 109:244-246.

Bult et al., "Complete genome sequence of the methanogenicarchaeon, Methanococcus jannaschii," Science, 1996, 273: 1058-1073.

Bunik et al., "Kinetic properties of the 2-oxoglutarate dehydrogenase complex from Azotobacter vinelandii evidence for the formation of a precatalytic complex with 2-oxoglutarate," Eur J Biochem., 267(12):3583-3591, Jun. 2000.

Cantu et al., "Thioesterases: A new perspective based on their primary and tertiary structures," Protein Science 2010, 19:1281-1295.

Chayabutra and Ju, "Degradation of n-hexadecane and its metabolites by Pseudomonas aeruginosa under microaerobic and anaerobic denitrifying conditions," Appl Environ Microbiol., 66(2):493-498, Feb. 2000.

Cheesbrough and Kolattukudy, "Alkane biosynthesis by decarbonylation of aldehydes catalyzed by a particulate preparation from Pisum sativum," PNAS USA, 1984, 81(21):6613-7.

Chen et al., "Termites fumigate their nests with naphthalene," Nature, 1998, 392:558-559.

Cheng et al., "Genetic Analysis of a Gene Cluster for Cyclohexanol Oxidation in *Acinetobacter* sp. Strain SE19 by In Vitro Transposition," Journal of Bacteriology, 2000, 182(17):4744-4751.

Clomburg et al., "Integrated engineering of Beta-oxidation reversal and omega-oxidation pathways for the synthesis of medium chain omega-functionalized carboxylic acids," Metabolic Engineering, Jan. 2015, 28:202-212.

Coon, "Omega oxygenases: nonheme-iron enzymes and P450 cytochromes," Biochemical & Biophysical Research Communications, 2005,338:378-385.

Cronan and Lin, "Synthesis of the α,ω-dicarboxylic acid precursor of biotin by the canonical fatty acid biosynthetic pathway," Current Opinion in Chem Biol., 2011, 15:407-413.

Cryle and Schlichting, "Structural insights from a P450 Carrier Protein complex reveal how specificity is achieved in the P450BioI ACP complex," Proceedings of the National Academy of Sciences, Oct. 2008, 105(41):15696-15701.

Cryle et al., "Carbon-carbon bond cleavage by cytochrome P450BioI (CYP107H1) E1," Chemical Communications, Jan. 2004, 86-87.

Cryle, "Selectivity in a barren landscape: the P450BioI-ACP complex," Biochemical Society Transactions, Aug. 2010, 38(4):934-939.

Da Silva et al., "Glycerol: A promising and abundant carbon source for industrial microbiology," Biotechnology Advances, 2009, 27:30-39.

Daisy et al., "Naphthalene, an insect repellent, is produced by Muscodor vitigenus, a novel endophytic fungus," Microbiology, 2002, 148:3737-3741.

Dalby, "Optimizing enzyme function by directed evolution," Current Opinion in Structural Biology, 2003, 13, 500-505.

Davis et al., "Overproduction of acetyl-CoA carboxylase activity increases the rate of fatty acid biosynthesis in *Escherichia coli*," J. Biol. Chem., 2000, 275(37): 28593-28598.

Day et al., "Partial purification and properties of acyl-CoA reductase from *Clostridum butyricum*," Archives of Biochemistry and Biophysics, 1978, 190(1):322-331.

Deana et al., "Substrate specificity of a dicarboxyl-CoA: Dicarboxylic acid coenzyme. A transferase from rat liver mitochondria," Biochem Int., 1992, 26:767-773.

Dekishima et al., "Extending Carbon Chain Length of 1-Butanol Pathway for 1-Hexanol Synthesis from Glucose by Engineered *Escherichia coli*," J. Am. Chem. Soc., Aug. 2011, 133(30):11399-11401.

Dellomonaco et al., "Engineered reversal of the [beta]-oxidation cycle for the synthesis of fuels and chemicals," Nature, Jan. 2011, 476(7360):355-359.

Deshmukh and Mungre, "Purification and properties of 2-aminoadipate: 2-oxoglutarate aminotransferase from bovine kidney," Biochem J, 1989, 261(3):761-768.

Doan et al., "Functional expression of five *Arabidopsis* fatty acyl-CoA reductase genes in *Escherichia coli*," J. Plant Physiology, 2009, 166:787-796.

Dobritzsch et al., "High resolution crystal structure of pyruvate decarboxylase from Zymomonas mobilis. Implications for substrate activation in pyruvate decarboxylases," J. Biol. Chem., 1998, 273:20196-20204.

Donoghue and Trudgill, "The Metabolism of Cyclohexanol by Acinetobacter NCIB9871," Eur J Bochem., 1975, 60:1-7.

Drevland et al., "Enzymology and Evolution of the Pyruvate Pathway to 2-Oxobutyrate in Methanocaldococcus jannaschii," J. Bacteriol., Apr. 2007, 189(12):4391-4400.

Drevland et al., "Methanogen homoaconitase catalyzes both hydrolyase reactions in coenzyme B biosynthesis," J Biol Chem., Oct. 2008, 283: 28888-28896.

Egmond et al., "Fusarium solani pisi cutinase," Biochimie, Nov. 2000, 82(11):1015-1021.

Eikmanns and Buckel, "Properties of 5-hydroxyvalerate CoA-transferase from *Clostridium aminovalericum*," Biol. Chem, 1990, 371:1077-1082.

Elkins et al., "Substrate Specificity of the RND-Type Multidrug Efflux Pumps AcrB and AcrD of *Esherichia coli* Is Determined Predominately by Two Large Periplasmic Looops," J Bacteriol. 2002, 184(23):6490-6499.

Elshahed et al., "Benzoate Fermentation by the Anaerobic bacterium Syntrophus aciditrophicus in the Absence of Hydrogen-Using Microorganisms," Applied and Environ Microbiology, 2001, 67(12):5520-5525.

Elshahed et al., "Metabolism of Benzoate, Cyclohex-1-ene Carboxylate, and Cyclohexane Carboxylate by Syntrophus aciditrophicus Strain SB in Syntrophic Association with H2-Using Microorganisms," Applied and Environ. Microbiol., Apr. 2001, 67(4):1728-1738.

Eurich et al., "Cloning and characterization of three fatty alcohol oxidase genes from Candida tropicalis strain ATCC 20336," Applied & Environmental Microbiology, 2004, 70(8): 4872-4879.

Ferreira et al. "A member of the sugar transporter family, Stl1p is the glycerol/H=symporter in *Saccharomyces cerevisiae*," Molecular Biology of the Cell, American Society for Cell Biology, Apr. 1, 2005, 16(4):2068-2076.

Fickers et al., "Carbon and nitrogen sources modulate lipase production in the yeast Yarrowia lipolytica," Journal of Applied Microbiology , 2004, 96:742-9.

Fickers et al., "The lipases from Yarrowia lipolytica: Genetics, production, regulation, biochemical characterization and biotechnological applications," Biotechnology Advances, 2011, 29: 632-644.

Fonknechten et al., "Clostridium sticklandii, a specialist in amino acid degradation: revisiting its metabolism through its genome sequence," BMC Genomics, 2010, 11:1-12.

Fuchs et al., "Microbial degradation of aromatic compounds—from one strategy to four," Nat Rev Microbiol., Oct. 3, 2011;9(11):803-816, Oct. 2011.

Fukui et al., "Expression and Characterization of ®-Specific Enoly Coenzyme A Hydratase Involved in Polyhydroxyalkanoate Biosynthesis by Aeromonas caviae," J Bacteriol. 1998, 180(3):667-673.

Funhoff et al., "CYP153A6, a Soluble P450 Oxygenase Catalyzing Terminal-Alkane Hydroxylation," J Bacteriol. 2006, 188(14):5220-5227.

Funhoff et al., "Expression and Characterization of (R)-Specific Enoyl Coenzyme A Hydratase Involved in Polyhydroxyalkanoate Biosynthesis by Aeromonas caviae," J. Bacteriol., 2006, 188(14):5220-5227.

Gallus and Schink, "Anaerobic degradation of pimelate by newly isolated denitrifying bacteria," Microbiology, 1994, 140:409-416.

(56) References Cited

OTHER PUBLICATIONS

Gao et al: "A novel meso-diaminopimelate dehydrogenase from Symbiobacterium thermophilum: overexpression, characterization, and potential for D-amino acid synthesis," Applied and Environmental Microbiology, 2012, 78:8595-8600.
Gasmi et al., "A molecular approach to optimize hIFN α2b expression and secretion in Yarrowia lipolytica," Appl Microbiol Biotechnol, 2011, 89:109-119.
GenBank Accession No. AAA23536, Apr. 26, 1993, 1 page.
GenBank Accession No. AAA24664.1, Mar. 25, 1993, 1 page.
GenBank Accession No. AAA24665.1, Apr. 26, 1993, 1 page.
GenBank Accession No. AAA57874.1, Nov. 21, 2011, 2 pages.
GenBank Accession No. AAA69178.1, Jul. 1, 1995, 1 page.
GenBank Accession No. AAA92347.1, Mar. 15, 1996, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct 23, 2009, 2 pages.
GenBank Accession No. AAB99100, Aug. 27, 1996, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
GenBank Accession No. AAF02538.1, Oct. 20, 1999, 2 pages.
GenBank Accession No. AAG08191.1, Jan. 31, 2014, 2 pages.
GenBank Accession No. AAK73167.2, retrieved May 19, 2014, 1 page.
GenBank Accession No. AAN37290.1, retrieved May 19, 2014, 1 page.
GenBank Accession No. AAO77182, Mar. 28, 2003, 1 page.
GenBank Accession No. AAQ59697.1, Jan. 31, 2014, 2 pages.
GenBank Accession No. AAS11092.1, Mar. 5, 2010, 1 page.
GenBank Accession No. AAS43086.1, dated Nov. 2011, 1 page.
GenBank Accession No. AAT43726, retrieved May 19, 2014, 1 page.
GenBank Accession No. AAW66853.1, Feb. 12, 2005, 1 page.
GenBank Accession No. AAY39893.1, Jan. 31, 2014, 2 pages.
GenBank Accession No. AB005294, Feb. 2000, 2 pages.
GenBank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
GenBank Accession No. ABE47158.1, Jan. 26, 2014, 1 page.
GenBank Accession No. ABE47159.1, Jan. 28, 2014, 2 pages.
GenBank Accession No. ABE47160.1, Jan. 28, 2014, 1 page.
GenBank Accession No. ABI83656.1, Jan. 3, 2007, 1 page.
GenBank Accession No. ABJ63754.1, dated Mar. 2010, 1 page.
GenBank Accession No. ABK71854.1, Jan. 31, 2014, 2 pages.
GenBank Accession No. ABK75684.1, Jan. 31, 2014, 2 pages.
GenBank Accession No. ACC40567.1, Jan. 31, 2014, 2 pages.
GenBank Accession No. ACJ06772.1, Dec. 4, 2009, 1 page.
GenBank Accession No. ADG98140.1, Jan. 28, 2014, 2 pages.
GenBank Accession No. ADK19581.1, Sep. 20, 2010, 2 pages.
GenBank Accession No. AE000666.1, Jan. 5, 2006, 309 pages.
GenBank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
GenBank Accession No. BAB91331.1, retrieved May 19, 2014, 1 page.
GenBank Accession No. BAC06606, Aug. 1, 2002, 1 page.
GenBank Accession No. BAD69624, Sep. 2005, 1 page.
GenBank Accession No. BAF92773, Nov. 27, 2007, 1 page.
GenBank Accession No. BAF94304.1, retrieved May 19, 2014, 1 page.
GenBank Accession No. CAA44858.1, Apr. 28, 1992, 1 page.
GenBank Accession No. CAA81612.1, Apr. 18, 2005, 2 pages.
GenBank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 page.
GenBank Accession No. CAE26094.1, Apr. 17, 2005, 2 pages.
GenBank Accession No. CAE26097.1, Apr. 17, 2005, 2 pages.
GenBank Accession No. CAH04396.1, Apr. 7, 2005, 1 page.
GenBank Accession No. CAH04397.1, Apr. 7, 2005, 2 pages.
GenBank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. D87518, Jul. 31, 1997, 2 pages.
GenBank Accession No. EFV11917.1, Sep. 9, 2013, 2 pages.
GenBank Accession No. EIV11143.1, Jun. 19, 2012, 2 pages.
GenBank Accession No. HQ418483.1, Apr. 4, 2011, 2 pages.
GenBank Accession No. JA114119.1, Apr. 19, 2011, 1 page.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 Pages.
GenBank Accession No. NM_001246944, Dec. 2011, 2 pages.
GenBank Accession No. NM_001247852, Dec. 2011, 2 pages.
GenBank Accession No. NM_133240, Feb. 25, 2002, 2 pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus Sphaericus* genes controlling the bioconversion of pimlate into dethiobiotin," Gene, 1990, 87:63-70.
Gloerich et al., "Peroxisomal trans-2-enoyl-CoA reductase is involved in phytol degradation," FEBS Letters 2006, 580:2092-2096.
Gocke et al., "Comparative characterization of ThPP-dependent decarboxylases," J. Mol. Cat. B: Enzymatic, 2009, 61:30-35.
Gonzalez-Lopez, "Genetic control of extracellular protease synthesis in the yeast Yarrowia lipolytica," Genetics, 2002, 160: 417-427.
Graupner et al., "Identification of the gene encoding sulfopyruvate decarboxylase, an enzyme involved in biosynthesis of coenzyme M," J Bacterial., 2000, 182: 4862-4867.
Guerrillot et al., "Purification and Characterization of Two Aldehyde Dehydrogenases from Pseudomonas aeruginosa," Eur. J. Biochem. 1977, 81:185-192.

(56) References Cited

OTHER PUBLICATIONS

Hall, "The Contribution of Horizontal Gene Transfer to the Evolution of Fungi," Duke University Libraries, May 10, 2007, 163 pages.
Hall, "Asymmetric bioreduction of activated alkenes using cloned 12-oxophytodienoate reductase isoenzymes OPR-1 and OPR-3 from Lycopersicon esculentum (tomato): a striking change of stereoselectivity," Agnew Chem Int. Ed., 2007, 46:3934-3937.
Han et al., "Oxaloacetate hydrolase, the C—C bond lyase of oxalate secreting fungi," J. Biol. Chem. 2007, 282:9581-9590.
Harrison and Harwood, "The pimFABCDE operon from Phodopseudomonas palustris mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.
Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism Alcaligenes eutrophus," FEMS Microbiology Letters 1988, 52(1-2):91-96.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from Bacillus subtilis," J Biol Chem., 275(51):40128-40133, Dec. 22, 2000.
Hermann et al, "Industrial production of amino acids by coryneform bacteria," J Biotechnol. 2003, 104(1-3):155-172.
Hess et al., "Extremely thermostable esterases from the thermoacidophilic euryarchaeon Picrophilus torridus," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from Euglena gracilis defines a new family of enzymes involved in lipid synthesis," J Biol Chem., 280(6):4329-4338. Epub Nov. 29, 2004.
Hofvander et al., "A prokaryotic acyl-CoA reductase performing reduction of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of *Arabidopsis*," Plant J., 1999, 20:1-13.
Horning et al., "α-Ketoglutaric Acid," Organic Syntheses, 1955, 3:510-512.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenicArchaea," Biochemistry, 1989, 37: 10108-10117.
Howell et al., "Identification of enzymes homologous to isocitrate dehydrogenase that are involved in coenzyme Band leucine biosynthesis in methanoarchaea," J Bacteriol., Sep. 2000, 182: 5013-5016.
Hugler et al., "Malonyl-coenzyme A reductase from Chloroflexus aurantiacus, a key enzyme of the 3-hydroxypropionate cycle for autotrophic CO(2) fixation," J. Bacteriology, 2002, 184:2404-2410.
Huhn et al., "Identification of the membrane protein SucE and its role in succinate transport in Corynebacterium glutamicum," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.
International Preliminary Report on Patentability for International Application No. PCT/US 2012/069934, dated Jun. 17, 2014, 15 pages.
International Preliminary Report on Patentability in International Application No. PCT/US 2012/042777, dated Jan. 10, 2013, 22 pages.
International Preliminary Report on Patentability in International Application No. PCT/US 2012/044984, dated Jan. 28, 2014, 11 pages.
International Preliminary Report on Patentability for International Application No. PCT/US 2013/075058, dated Jun. 25, 2015, 11 pages.
International Preliminary Report on Patentability for International Application No. PCT/US 2013/075087, dated Jun. 25, 2015, 11 pages.
International Preliminary Report on Patentability for International Application No. PCT/US 2013/077445, dated Jul. 9, 2015, 11 pages.
International Preliminary Report on Patentability for International Application No. PCT/US 2013/077420, dated Jul. 9, 2015, 14 pages.
International Preliminary Report on Patentability for International Application No. PCT/US 2013/077419, dated Jul. 9, 2015, 13 pages.
International Preliminary Report on Patentability for International Application No. PCT/US 2013/077430, dated Jul. 9, 2015, 18 pages.
International Preliminary Report on Patentability for International Application No. PCT/US 2013/077413, dated Jul. 9, 2015, 13 pages.
International Preliminary Report on Patentability for International Application No. PCT/US 2013/077411, dated Jul. 9, 2015, 12 pages.
International Preliminary Report on Patentability for International Application No. PCT/US 2013/077423, dated Jul. 9, 2015, 14 pages.
International Search Report and Written Opinion in International Application No. PCT/US 2014/052950, dated Dec. 3, 2014, 15 pages.
International Search Report and Written Opinion for International Application No. PCT/US 2012/069934, dated Jan. 17, 2014, 21 pages.
International Search Report and Written Opinion in International Application No. PCT/US 2012/042747, dated Jan. 14, 2013, 19 pages.
International Search Report and Written Opinion in International Application No. PCT/US 2012/042777, dated Sep. 11, 2012, 9 pages.
International Search Report and Written Opinion in International Application No. PCT/US 2012/044984, dated Dec. 17, 2013, 17 pages.
International Search Report and Written Opinion in International Application No. PCT/US 2012/071472, dated Dec. 17, 2013, 17 pages.
International Search Report and Written Opinion in International Application No. PCT/US2013/075058, dated Sep. 15, 2014, 17 pages.
International Search Report and Written Opinion in International Application No. PCT/US2013/075087, dated Aug. 4, 2014, 18 pages.
International Search Report and Written Opinion in International Application No. PCT/US2013/077411, dated Sep. 24, 2014, 18 pages.
International Search Report and Written Opinion in International Application No. PCT/US2013/077413, dated Jul. 22, 2014, 20 pages.
International Search Report and Written Opinion in International Application No. PCT/US2013/077419, dated Jun. 16, 2014, 19 pages.

(56) References Cited

OTHER PUBLICATIONS

International Search Report and Written Opinion in International Application No. PCT/US2013/077420, dated Jul. 21, 2014, 21 pages.
International Search Report and Written Opinion in International Application No. PCT/US2013/077423, dated Jul. 21, 2014, 22 pages.
International Search Report and Written Opinion in International Application No. PCT/US2013/077430, dated Nov. 10, 2014, 23 pages.
International Search Report and Written Opinion in International Application No. PCT/US2013/077445, dated Sep. 15, 2014, 17 pages.
International Search Report and Written Opinion in International Application No. PCT/US2014/053222, dated Mar. 4, 2015, 18 pages.
International Search Report and Written Opinion in International Application No. PCT/US2015/031227, dated Jul. 31, 2015, 40 pages.
International Search Report and Written Opinion in International Application No. PCT/US2015/036050, dated Aug. 14, 2015, 38 pages.
International Search Report and Written Opinion in International Application No. PCT/US2015/036057, dated Aug. 14, 2015, 74 pages.
Invitation to Pay Additional Fees in International Application No. PCT/US2013/075058, dated Jul. 7, 2014, 7 pages.
Invitation to Pay Additional Fees in International Application No. PCT/US2013/07745, dated Jul. 7, 2014, 9 pages.
Invitation to Pay Additional Fees in International Application No. PCT/US2014/053222, dated Dec. 15, 2014, 8 pages.
Invitation to Pay Fees in International Application No. PCT/US2013/075087, dated May 16, 2014, 9 pages.
Invitation to Pay Fees in International Application No. PCT/US2013/077411, dated Jul. 16, 2014, 9 pages.
Invitation to Pay Fees in International Application No. PCT/US2013/077413, dated May 12, 2014, 9 pages.
Invitation to Pay Fees in International Application No. PCT/US2013/077419, dated Apr. 16, 2014, 9 pages.
Invitation to Pay Fees in International Application No. PCT/US2013/077420, dated May 13, 2014, 9 pages.
Invitation to Pay Fees in International Application No. PCT/US2013/077423, dated May 13, 2014, 10 pages.
Invitation to Pay Fees in International Application No. PCT/US2013/077430, dated Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbiology, 2002, 68:1192-1195.
Ishikawa et al., "The pathway via D-galacturonate/L-galactonate is significant for ascorbate biosynthesis in Euglena gracilis: identification and functional characterization of aldonolactonase," Journal of Biologiocal Chemistry, 2008, 283:31133-31141.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.
Izumi et al., "Structure and Mechanism of HpcG, a Hydratase in the Homoprotocatechuate Degradation Pathway of *Escherichia coli*," J. Mol. Biol., 2007, 370:899-911.
Izumi et al., "The pimeloyl-CoA synthetase responsible for the first step in biotin biosynthesis by microorganisms," Agr. Biol. Chem., 1974, 38:2257-2262.

Jacob et al., "Glutaconate CoA-transferase from *Acidamiococcus fermentans*: the crystal structure reveals homology with other CoA-transferases," Structure, 1997, 5:415-426.
Jang et al., "Bio-based production of C2-C6 platform chemicals," Biotechnol. & Bioengineering, 2012, 109(10):2437-2459.
Jarboe, "YqhD: a broad-substrate range aldehyde reductase with various applications in production of biorenewable fuels and chemicals," Appl Microbiol Biotechnol., 2011, 89(2):249-257.
Jaremko et al., "The initial metabolic conversion of levulinic acid in Cupriavidus nectar," J. Biotechnol., 2011, 155(3):293-298.
Jeyakanthan et al., "Substrate specificity determinants of the methanogen homoaconitase enzyme: structure and function of the small subunit," Biochemistry, 2010, 49:2687-2696.
Jing et al., "Phylogenetic and experimental characterization of an acyl-ACP thioesterase family reveals significant diversity in enzymatic specificity and activity," BMC Biochemistry, 2011, 12:44, 16 pages.
Joon-Young et al., "Production of 1,2-Propanediol from Glycerol in *Saccharomyces cerevisiae*," J. Microbiology and Biotechnology, May 19, 2011, 21(8):846-853.
Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.
Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.
Kaulmann et al., "Substrate spectrum of omega-transaminase from Chromobacterium violaceum DSM30191 and its potential for biocatalysis," Enzyme Microb Technol. 2007, 41:628-637.
KEGG Enzyme 1.2.99.6 (last viewed on Aug. 17, 2015).
KEGG Enzyme 3.1.2.14 (last viewed on Aug. 17, 2015).
Kikuchi et al., "Characterization of a second lysine decarboxylase isolated from *Escherichia coli*," J Bacteriol, 1997, 179(14): 4486-4489.
Kim et al., "Cloning and characterization of a cyclohexanone monooxygenase gene from *Arthrobacter* sp. L661," Biotechnology Bioprocess Engineering, 2008, 13:40-47.
Kim, "Purification and properties of a diamine alpha-ketoglutarate transaminase from *Escherichia coli*," J Biol Chem 1964, 239(3):783-786.
Kitzing et al., "The 1.3 a crystal structure of the flavoprotein YqjM reveals a novel class of Old Yellow Enzymes," J. Biol. Chem., 2005, 280:27904-27913.
Kizer, "Application of Functional Genomics to Pathway Optimization for Increased Isoprenoid Production," Applied and Environmental Microbiology, 2008, 74(10)3229-3241.
Klatte et al., "Redox self-sufficient whole cell biotransformation for amination of alcohols," Bioorg & Medicinal Chem, May 2014, 22: 5578-5585.
Koch et al., "Products of Enzymatic Reduction of Benzoyl-CoA, A Key Reaction in Anaerobic Aromatic Metabolism," Eur. J. Biochemistry, Jan. 1993, 211(3):649-661.
Koch et al., "In Vivo Evolution of Butane Oxidation by Terminal Alkane Hydroxylases AlkB and CYP153A6," Appl. Environ. Microbiol., 2009, 75(2):337-344.
Kockelkorn and Fuchs, "Malonic semialdehyde reductase, succinic semialdehyde reductase, and succinyl-coenzyme A reductase from Metallosphaera sedula: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.
Kulkarni and Kanekar, "Bioremediation of epsilon-caprolactam from nylon-6 waste water by use of Pseudomonas aeruginosa MCM B-407," Curr. Microbiol., 1998, 37:191-194.

(56) References Cited

OTHER PUBLICATIONS

Kung et al., "Cyclohexane carboxyl-coenzyme A (CoA) and cyclohex-1-ene-l-carboxyl-CoA dehydrogenases, two enzymes involved in the fermentation of benzoate and crotonate in Syntrophus aciditrophicus," J Bacteriol., 195(14):3193-3200, Epub May 10, 2013.
Lan et al., "Oxygen-tolerant coenzyme A—acylating aldehyde dehydrogenase facilitates efficient photosynthetic n-butanol biosynthesis in cyanobacteria," Energy Environ Sci, 2013, 6:2672-2681.
Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.
Le Dall et al., "Multiple-copy integration in the yeast Yarrowia lipolytica," Current Genetics, 1994 26:38-44.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Lee and Meighen, "Cysteine-286 as the site of acylation of the LUX-specific fatty acyl-CoA reductase," Biochim Biophys Acta, 1997, 1338:215-222.
Lee et al., "Metabolic Engineering of Pentose Phosphate Pathway in Ralstonia eutropha for Enhanced Biosynthesis of Poly-β-hydroxybutyrate," Biotechnology Progress, 2003, 19(5):1444-1449.
Lee et al., "Synthesis of pure meso-2,3-butanediol from crude glycerol using an engineered metabolic pathway in *Escherichia coli*," Appl Biochem Biotechnol., 2012, 166(7):1801-1813.
Li et al., "Cupriavidus necator JMP 134 rapidly reduces furfural through a Zn-dependent alcohol dehydrogenase," Biodegradation, 2011, 22:1215-1225.
Lim et al., "Amplification of the NADPH-related genes zwf and gnd for the oddball biosynthesis of PHB in an *E. coli* transformant harboring a cloned phbCAB operon," J Bioscience and Bioengineering, 2002, 93(6):543-549.
Lin and Cronan, "Closing in on complete pathways of biotin biosynthesis," Molecular Biosystems, 2011, 7:1811-1821.
Lin et al., "Biotin Sythesis Begins by Hijacking the Fatty Acid Synthetic Pathway," Nature Chem Biol., Sep. 2010, 6:682-688.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin, "Biotin Synthesis in *Escherichia coli*," PhD Dissertation, University of Illinois at Urbana-Champaign, 2012, 140 pages.
Liu and Chen, "Production and characterization of medium-chain-length polyhydroxyalkanoate with high 3-hydroxytetradecanoate monomer content by fadB and fadA knockout mutant of Pseudomonas putida KT2442," Appl. Microbiol. Biotechnol., 2007, 76(5):1153-1159.
Liu et al., "Two novel metal-independent long-chain alkyl alcohol dehydrogenases from Geobacillus thermodenitrificans NG80-2," Microbiology, 2009, 155:2078-2085.
Lopez-Sanchez et al., "Tetralin-Induced and ThnR-Regulated Aldehyde Dehydrogenase and β-Oxidation Genes in Sphingomonas macrogolitabida Strain TFA," Appl. Environ. Microbiol., 2010, 76(1):110-118.
Luo et al., "Production of 3-hydroxypropionic acid through propionaldehyde dehydrogenase PduP mediated biosynthetic pathway in Klebsiella pneumoniae," Bioresource Technology, 2012, 103:1-6.
Lütke-Eversloh & Steinbüchel, "Biochemical and molecular characterization of a succinate semialdehyde dehydrogenase involved in the catabolism of 4-hydroxybutyric acid in Ralstonia eutropha," FEMS Microbiology Letters, 1999, 181(1):63-71.
Mack and Buckel, "Conversion of glutaconate CoA-transferase from Acidaminococcus fermentans into an acyl-CoA hydrolase by site-directed mutagenesis," FEBS Letters, 1997, 405:209-212.
Maeda et al., "Purification and characterization of a biodegradable plastic-degrading enzyme from Aspergillus oryzae," Applied and Environmental Biotechnology, 2005, 67: 778-788.
Mahadik et al., "Production of acidic lipase by Aspergillus niger in solid state fermentation," Process Biochemistry, 2002, 38: 715-721.
Martin and Prather, "High-titer production of monomeric hydroxyvalerates from levulinic acide Pseudomonas putida," J. Biotechnol., 2009, 139: 61-67.
Martinez et al., "Fusarium solani cutinase is a lipolytic enzyme with a catalytic serine accessible to solvent," Nature, 1992, 356:615-618.
Matsumoto et al., "A new pathway for poly(3-hydroxybutyrate) production in *Escherichia coli* and Corynebacterium glutamicum by functional expression of a new acetoacetyl-coenzyme A synthase," Biosci. Biotechnol. Biochem., 2011, 75(2):364-366.
Mawal and Deshmukh, "Alpha-aminoadipate and kynurenine aminotransferase activities from rat kidney. Evidence for separate identity," J. Biol Chem, 1991, 266(4):2573-2575.
McAndrew et al., "Structural basis for substrate fatty acyl chain specificity: crystal structure of human very-long-chain acyl-CoA dehydrogenase," J. Biol. Chem., 2008, 283:9435-9443.
Meijnen et al., "Improved p-hydroxybenzoate production by engineered Pseudomonas putida S12 by using a mixed-substrate feeding strategy," Appl. Microbiol. Biotechnol., 2011, 90:885-893.
Mhetras et al., "Purification and characterization of acidic lipase from Aspergillus niger NCIM 1207," Bioresource Technology, 2009, 100: 1486-1490.
Millar et al., "CUT1, an *Arabidopsis* Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.
Miyazaki et al., "Alpha-Aminoadipate aminotransferase from an extremely thermophilic bacterium, Thermus thermophilus," Microbiology, 2004, 150(7): 2327-2334.
Mo et al., "Connecting extracellular metabolomic measurements to intracellular flux states in yeast," BMC Systems Biology, 2009, 3(37):1-17.
Mouttaki et al., "Cyclohexane Carboxylate and Benzoate Formation from Crotonate in Sytrophus aciditrophicus," Applied and Environ Microbiology, Feb. 2007, 73(3):930-938.
Murphy et al., "Fusarium polycaprolactone depolymerase is cutinase," Appl. Environm. Microbiol., 1996, 62:456-460.
Mutti et al., "Amination of ketones by employing two new (S)-selective w-transaminases and the His-tagged w-TA from Vibrio fluvialis," Eur. J. Org. Chem, 2012, 1003-1007 (Abstract).
Naggert et al., "Cloning, sequencing, and characterization of *Escherichia coli* thioesterase II," J. Biol. Chem., 1991, 266(17):11044-11050.
Neyfakh, "The Multidrug Efflux Transporter of Bacillus subtilis is a Structural and Functional Homolog of the *Staphylococcus* NorA Protein," Antimicrob Agents Chemother, 1992, 36(2):484-485.
Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.
Nicol et al., "Bioconversion of crude glycerol by fungi," Applied Microbiology and Biotechnology, Feb. 10, 2012, 93(5):1865-1875.
Nieder and Shapiro, "Physiological function of the Pseudomonas putida PpG6 (*Pseudomonas oleovorans*) alkane hydroxylase: monoterminal oxidation of alkanes and fatty acids," J. Bacteriol., 1975, 122(1):93-98.
Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.
Ohashi et al., "Continuous production of lactic acid from molasses by perfusion culture of Lactococcus lactis using a stirred ceramic membrane reactor," J. Bioscience and Bioengineering, 1999, 87(5):647-654.

(56) References Cited

OTHER PUBLICATIONS

Okuhara et al., "Formation of Glutaric and Adipic Acids from n-Alkanes with Odd and Even Numbers of Carbons by Candida tropicalis OH23," Agr. Biol. Chem., 1971, 35(9):1376-1380.
Onakunle et al., "The formation and substrate specificity of bacterial lactonases capable of enantioselective resolution of racemic lactones," Enzyme and Microbial Technology, 1997, 21: 245-251.
Oppenheim and Dickerson, "Adipic Acid," Kirk-Othmer Encyclopedia of Chemical Technology, 2003.
Ouchi et al., "Dual roles of a conserved pair, Arg23 and Ser20, in recognition of multiple substrates in alpha-aminoadipate aminotransferase from Thermus thermophilus," Biochem Biophys Res Commun, 2009, 388(1):21-27.
Palosaari and Rogers, "Purification and properties of the inducible coenzyme A-linked butyraldehyde dehydrogenase from Clostridium acetobutylicum," J. Bacteriol., 1988, 170(7):2971-2976.
Papanikolaou et al., "Citric acid production by Yarrowia lipolytica cultivated on olive-mill wastewater-based media," Bioresource Technol., 2008, 99(7):2419-2428.
Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.
Pelletier and Harwood et al., "2-Hydroxycyclohexanecarboxyl coenzyme A dehydrogenase, an enzyme characteristic of the anaerobic benzoate degradation pathway used by Rhodopseudomonas palustris," J Bacteriol., 182(10):2753-2760, May 2000.
Pérez-Pantoja et al., "Metabolic reconstruction of aromatic compounds degradation from the genome of the amazing pollutant-degrading bacterium Cupriavidus necator JMP134," FEMS Microbiol. Rev., 2008, 32:736-794.
Peterson et al., "The Thermal Stability of the Fusarium solani pisi Cutinase as a Function of pH," BioMed Research International, 2001, 1.2:62-69.
Pignede et al., "Autocloning and Amplification of LIP2 in Yarrowia lipolytica,"Appl. Environ. Microbiol, 2000 66:3283-3289.
Pignede et al., "Characterization of an extracellular lipase encoded by LIP2 in Yarrowia lipolytica," Journal of Bacteriology, 2000, 182: 2802-2810.
Ploux et al., "Investigation of the first step of biotin biosynthesis in Bacillus sphaericus: Purification and characterization of the pimloyl-CoA synthase, and uptake of pimelate," Biochem J., 1992, 287:685-690.
Prabhu et al., "Lactate and Acrylate Metabolism by Megasphaera elsdenii under Batch and Steady-State Conditions," Applied and Environ. Microbiology, Sep. 2012, 78(24): 8564-8570.
Prather et al., "De novo biosynthetic pathways: rational design of microbial chemical factories," Current Opinion in Biotechnology, 2008, 19:468-474.
Prybylski et al., "Third-generation feed stocks for the clean and sustainable biotechnological production of bulk chemicals: synthesis of 2-hydroxyisobutyric acid," Energy, Sustainability and Society, 2012, 2:11.
Qian et al., "Metabolic engineering of *Escherichia coli* for the production of cadaverine: a five carbon diamine," Biotechnol Bioeng, 2011, 108(1):93-103.
Qiu et al., "Crystal structure and substrate specificity of the β-ketoacyl-acyl carrier protein synthase III (FabH) from *Staphylococcus aureus*," Protein Sci, 2005, 14(8):2087-2094.
Rajashekhara et al., "Propionyl-coenzyme A synthetases of Ralstonia solanacearum and *Salmonella choleraesuis* display atypical kenetics," FEBS Letters, 2004, 556:143-147.
Ramsay et al., "Use of a Nylon Manufacturing Waste as an Industrial Feimentation Substrate," Applied and Environmental Microbiology, 1986, 52(1):152-156.
Ray et al., "Cocrystal structures of diaminopimelate decarboxylase: mechanism, evolution, and inhibition of an antibiotic resistance accessory factor," Structure, 2002, 10(11):1499-1508.
Rea et al., "Structure and Mechanism of HpcH: A Metal Ion Dependent Class II Aldolase from the Homoprotocatechuate Degradation Pathway of *Escherichia coli*," J. Mol. Biol., 2007, 373:866-876.
Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.
Rizzarelli et al., "Evidence for Selective Hydrolysis of Aliphatic Copolyesters Induced by Lipase Catalysis," Biomacromolecules, 2004, 5:433-444.
Rohdich et al., "Enoate reductases of Clostridia. Cloning, sequencing, and expression," J. Biol. Chem., 2001, 276:5779-5787.
Roje, "Vitamin B biosynthesis in plants," Phytochemistry, 2007, 68:1904-1921.
Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.
Ryu et al., "A novel synthesis of .beta.-trichlorostannyl ketones from siloxycyclopropanes and their facile dehydrostannation affording 2-methylene ketones," JOC, 1986, 51:2389-2391.
Salcher and Lingens, "Regulation of phospho-2-keto-3-deoxyheptonate aldolase (DAHP synthase) and anthranilate synthase of Pseudomonas aureofaciens," J Gen Microbiol., 121(2):473-476, Dec. 1980.
Sambrook et al., Molecular Cloning—a Laboratory Manual, Cold Spring Harbor Laboratory Press, 2001.
Samsonova et al., "Molecular cloning and characterization of *Escherichia coli* K12 ygjG gene," BMC Microbiology, 2003, 3:2.
Sanders et al., "Characterization of the human ω-oxidation pathway for ω-hydroxy-very-long-chain fatty acids," FASEB Journal, 2008, 22(6):2064-2071.
Sanders et al., "Evidence for two enzymatic pathways for ω-oxidation of docosanoic acid in rat liver microsomes," J. Lipid Research, 2005, 46(5):1001-1008.
Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.
Scheller et al., "Generation of the Soluble and Functional Cytosolic Domain of Microsomal Cytochrome P450 52A3," J Biol Chem., 1994, 269(17):12779-12783.
Scheps et al., "Synthesis of omega-hydroxy dodecanoic acid based on an engineered CYP153A fusion construct," Microbial Biotechnology, 2013, 6:694-707.
Schirmer et al., "Microbial Biosynthesis of Alkanes," Science, 2010, 329:559-562.
Schwartz et al., "A proteomic view of the facultatively chemolithoautotrophic lifestyle of Ralstonia eutropha H16," Proteomics, 2009, 9:5132-5142.
Seedorf et al., "The genome of Clostridium kluyveri, a strict anaerobe with unique metabolic features," Proc. Natl. Acad. Sci. USA, 2008, 105(6):2128-2133.
Shapiro et al., "Remarkable Diversity in the Enzymes Catalyzing the Last Step in Synthesis of the Pimelate Moiety of Biotin," PLoSOne, Nov. 2012, 7(11):e49440, 11 pages.
Shen et al., "Driving Forces Enable High-Titer Anaerobic 1-Butanol Synthesis in *Escherichia coli*," Appl. Environ. Microbiol., 2011, 77(9):2905-2915.
Shikata et al., "A novel ADP-forming succinyl-CoA synthetase in Thermococcus kodakaraensis structurally related to the archaeal nucleoside diphosphate-forming acetyl-CoA synthetases," J. Biol. Chem, 2007, 282(37):26963-26970.
Siegert et al., "Exchanging the substrate specificities of pyruvate decarboxylase from Zymomonas mobilis and benzoylformate decarboxylase from Pseudomonas putida," Port. Eng. Des. Sel., 2005, 18:345-357.
Simon et al., "Chiral Compounds Synthesized by Biocatalytic Reductions [New Synthetic Methods (51)]," Angew Chem Ed Engl., 1985, 24:539-553.
Simon, "Properties and mechanistic aspects of newly found redox enzymes from anaerobes suitable for bioconversions on preparatory scale," Pure and Appl. Chem, 1992, 64:1181-1186.

(56) References Cited

OTHER PUBLICATIONS

Slater et al., "Multiple β-Ketothiolases Mediate Poly(β-Hydroxyalkanoate) Copolymer Synthesis in Ralstonia eutropha," J Bacteriol., 1998, 180(8):1979-1987.
Smith et al., "Complete genome sequence of Methanobacterium thermoautotrophicum deltaH: functional analysis and comparative genomics," J Bacteriol., 1997, 179: 7135-7155.
Smith et al., "Structural analysis of ligand binding and catalysis in chorismate lyase," Archives of Biochemistry and Biophysics, Jan. 2006, 445(1):72-80.
Stok et al., "Expression, Purification, and Characterization of BioI: A Carbon-Carbon Bond Cleaving Cytochrome P450 Involved in Biotin Biosynthesis in Bacillus Subtilis," Archives of Biochemistry and Biophysics, Dec. 2000, 384(2):351-360.
Strassner et al., "A homolog of old yellow enzyme in tomato. Spectral properties and substrate specificity of the recombinant protein," J. Biol. Chem. 1999, 274:35067-35073.
Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.
Suzuki et al., "Acetylputrescine deacetylase from Micrococcus luteus K-11," BBA—General Subjects, 1986, 882(1):140-142.
Kobayashi et al., "Antimicrobial Activity of Meropenem Against Main Bacterial Species Isolated from Patient Blood in 2006," Jpn J. Antibiot., 2007, 60(6):378-86 (with English abstract).
Suzuki et al., "GriC and GriD Constitute a Carboxylic Acid Reductase Involved in Grixazone Biosynthesis in Streptomyces griseus," J. Antibiot., 2007, 60(6):380-387.
Tomita et al., "Mechanism for multiple-substrates recognition of alpha-aminoadipate aminotransferase from Thermus thermophilus," Proteins, 2009, 75(2):348-359.
Tseng et al., "Biosynthesis of chiral 3-hydroxyvalerate from single propionate-unrelated carbon sources in metabolically engineered E. coli," Microbial Cell Factories, 2010, 9:96.
Uniprot Accession No. I5YEB8, Sep. May 2012, 1 page.
U.S. Non-Final Office Action in U.S. Appl. No. 13/524,883, dated Nov. 29, 2013, 13 pages.
U.S. Non-Final Office Action in U.S. Appl. No. 13/715,981, dated Jun. 27, 2014, 23 pages.
U.S. Notice of Allowance in U.S. Appl. No. 13/524,883, dated May 29, 2014, 7 pages.
U.S. Notice of Allowance in U.S. Appl. No. 13/715,981, dated Dec. 16, 2014, 23 pages.
U.S. Notice of Allowance in U.S. Appl. No. 13/715,981, dated Apr. 6, 2015, 10 pages.
U.S. Non-Final Office Action in U.S. Appl. No. 13/715,826, dated Jan. 30, 2015, 24 pages.
U.S. Non-Final Office Action in U.S. Appl. No. 14/106,033, dated Apr. 6, 2015, 37 pages.
U.S. Non-Final Office Action in U.S. Appl. No. 14/138,827, dated Apr. 24, 2015, 35 pages.
U.S. Non-Final Office Action in U.S. Appl. No. 14/138,971, dated Jun. 9, 2015, 44 pages.
U.S. Non-Final Office Action in U.S. Appl. No. 14/138,904, dated Jun. 9, 2015, 50 pages.
U.S. Non-Final Office Action in U.S. Appl. No. 14/490,270, dated Jul. 17, 2015, 49 pages.
U.S. Non-Final Office Action in U.S. Appl. No. 14/130,117, dated Aug. 21, 2015, 49 pages.
U.S. Notice of Allowance in U.S. Appl. No. 14/106,124, dated Dec. 24, 2014, 31 pages.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.
Vioque et al., Resolution and purification of an aldehyde-generating and an alcohol-generating fatty-acyl-CoA reductase from Pea leaves (*Pisum sativum* L), Archives of Biochemistry and Biophysics, 1997, 340(1):64-72.
Vyazmensky et al., "Isolation and Characterization of Subunits of Acetohydroxy Acid Synthase Isozyme III and Reconstruction of the Holoenzyme," Biochemistry, 1996, 35:10339-10346.
Wahlen et al., "Purification, characterization and potential bacterial wax production role of an NADPH-dependent fatty aldehyde reductase from Marinobacter aquaeolei VT8," Appl. Environ Microbiol, 2009, 75:2758-2764.
Wang and Kolattukudy, "Solubilization and purification of aldehyde-generation fatty acyl-CoA reductase from green alga Botryococcus braunii," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferator-activated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White et al., "Carboxylic acid reductase: a new tungsten enzyme catalyses the reduction of non-activated carboxylic acids to aldehydes," Eur. J. Biochem., 1989, 184(1):89-96.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of Candida antarctica lipase A," BMC Genomics, 2010, 11:123-130.
Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.
Wischgoll et al., "Structural basis for promoting and preventing decarboxylation in glutaryl-coenzyme, A dehydrogenases," Biochemistry, 2010, 49:5350-5357.
Woolridge et al., "Efflux of the natural polyamine spermidine facilitated by the Bacillus subtilis multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of Streptomyces griseus: Purification and properties," Eur. J. Biochem., 1985, 146:101-106.
Zhang et al., "Expanding metabolism for biosynthesis of nonnatural alcohols," Proc Natl Acad Sci U S A., 105(52):20653-20658 Epub Dec. 8, 2008.
Zhao et al., "Prediction and characterization of enzymatic activities guided by sequence similarity and genome neighborhood networks," E-Life, Jun. 2014, 3: 1-32.
Zhuang et al., "Divergence of function in the hot dog fold enzyme superfamily: the bacterial thioesterase YciA," Biochemistry, 2008, 47(9):2789-2796.

(56) References Cited

OTHER PUBLICATIONS

Zomorrodi et al., "Improving the iMM904 S. Cerevisiae metabolic model using essentiality and synthetic lethality data," BMC Systems Biology, Dec. 2010, 4(1):1-15.
"Metabolic engineering," Wikipedia, Jun. 8, 2014 (Jun. 8, 2014), XP002744570, Retrieved from the Internet: URL:https://en.wikipedia.org/w/index.php?title=Metabolicengineering&oldid=612026466 [retrieved on Sep. 15, 2015] last paragraph.
Akatsuka et al., "The Serratia marcescens bioH gene encodes an esterase," GENE, Jan. 2003, 302:185-192.
Eriksen et al., "Protein Design for Pathway Engineering," Journal of Structural Biology, Apr. 2013, 185(2):234-242.
Invitation to Pay Fees in International Application No. PCT/US2015/036015, dated Oct. 2, 2015, 9 pages.
Invitation to Pay Fees in International Application No. PCT/US2015/036092, dated Sep. 21, 2015, 8 pages.
Invitation to Pay Fees in International Application No. PCT/US2015/036067, dated Sep. 18, 2015, 12 pages.
Klapa and Stephanopoulos, "Bioreaction Engineering: Modeling and Control," 2000, Springer Verlag, Heidelberg, pp. 106-124.
Moreno-Sanchez et al., "Experimental validation of metabolic pathway modeling—An illustration with glycolytic segments from Entamoeba histolytica," FEBS Journal, Jul. 2008, 275(13):3454-3469.
Palsson, "The challenges of in silico biology," Nature Biotechnology, Nature Publishing Group, US, Nov. 2000, 18(1):1147-1150.
Price et al., "Genome-scale models of microbial cells: evaluating the consequences of constraints," Nature Reviews. Microbiology, Nature Publishing Group, GB, Nov. 2004, 2(11):886-897.
Uniprot Accession No. 032472, Jun. 11, 2014, 2 pages.
Uniprot Accession No. P69909, Jan. 4, 2005, 1 page.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A953, Jun. 11, 2014, 4 pages.
Uniprot Accession No. P0A6Q6, Jun. 11, 2014, 3 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
Yadav et al., "The future of metabolic engineering and synthetic biology: Towards a systematic practice," Metabolic Engineering, Feb. 2012, 14(3):233-241.
Liang J et al., Coordinated induction of multi-gene pathways in *Saccharomyces cerevisiae*, Nucleic Acids Res., 2013;41(4):e54, Epub Dec. 22, 2012.
Bömke F et al., Tailoring plant metabolism for the production of novel polymers and platform chemicals, Curr Opin Plant Biol., 2010, 13(3):354-62.
Xu P et al., ePathBrick: a synthetic biology platform for engineering metabolic pathways in *E. coil*, ACS Synth Biol., 2012, 1(7):256-66.
Blombach B et al., Current knowledge on isobutanol production with *Escherichia coil*, *Bacillus subtilis* and *Corynebacterium glutamicum*, Bioeng Bugs., 2011, 2(6):346-50.
Adkins J et al., Engineering microbial chemical factories to produce renewable "biomonomers," Front Microbiol., 2012, 3:313.
Chan S et al., Production of succinic acid from sucrose and sugarcane molasses by metabolically engineered *Escherichia coli*, Bioresour Technol., 2012, 103(1):329-36.
Choi YJ et al., Metabolic engineering of *Escherichia coil* for the production of 1-propanol, Metab Eng., 2012, 14(5):477-86.
Lee S et al., Heterologous co-expression of accA, fabD, and thioesterase genes for improving long-chain fatty acid production in *Pseudomonas aeruginosa* and *Escherichia coli*, Appl Biochem Biotechnol., 2012, 167(1):24-38.
Rathnasingh C et al., Development and evaluation of efficient recombinant *Escherichia coli* strains for the production of 3-hydroxypropionic acid from glycerol, Biotechnol Bioeng., 2009, 104(4):729-39.

\* cited by examiner

FIGURE 10

| SEQ ID NO | Organism | GENBANK reference | Amino acid sequence |
|---|---|---|---|
| 1 | Salmonella typhimurium | CAC48239.1 | MQNPYTVADYLLDRLAGCGIGHLFGVPGDYNLQFLDHVIDHPTLRWVGCANELNAAYAADGYARMSGAGALLTTFGVGELSAINGIAGSYAEYVPVLHIVGAPCSAAQQRGELMHHTLGDGDFRHFYRMSQAISAASAHLDEQNACFEIDRVLGEMLAARRPGYIMLPADVAKKTAIPPTQALALPVHEAQSGVETAFRYHARQCLMNSRRIALLADFLAGRFGLRPLLQRWMAETPIAHATLLMGKGLFDEQHPNFVGTYSAGASSKEVRQAIEDADRVICVGTRFVDTLTAGFTQQLPAERTLEIQPYASRIGETWFNLPMAQAVSTLRELCLECAFAPPPTRSAGQPVRIDKGELTQESFWQTLQQYLKPGDIILVDQGTAAFGAAALSLPDGAEVVLQPLWGSIGYSLPAAFGAQTACPDRRVLIJGDGAAQLTIQEMGSMLRDGQAPVILLNNDGYTVERAIHGAAQRYNDIASWNWTQJPPALINAAQQAECWRVTQAIQLAEVLERLARPQRLSFIEVMLPKADLPELLRTVTRALEARNGG |

FIGURE 10 (Continued)

| SEQ ID NO | Organism | GENBANK reference | Amino acid sequence |
|---|---|---|---|
| 2 | *Mycobacterium marinum* | ACC40567.1 | MSPITREERLERRIQDLYANDPQFAAAKPATAITAAIERPGLPLPQIIETVMTGYADRPA LAQRSVEFVTDAGTGHTTLRLLPHEFTISYGFLWDRISALADVLSTEQTVKPGDRVCLLG FNSVDYATIDMTLARLGAVAVPLQTSAAITQLQPIVAETQPTMIAASVDALADATELALS GQTATRVLVFDHHRQVDAHRAAVESARERLAGSAVVETLAEAIARGDVPRGASAGSAPGT DVSDDSLALLIYTSGSTGAPKGAMYPRRNVATFWRKRTWFEGGYEPSITLNFMPMSHVMG RQJLYGTLCNGGTAYFVAKSDLSTLFEDLALVRPTELTFVPRVWDMVFDEFQSEVDRRLV DGADRVALEAQVKAEIRNDVLGGRYTSALTGSAPISDEMKAWVEELLDMHLVEGYGSTEA GMILIDGAIRRPAVLDYKLVDPDLGYFLTDRPHPRGELLVKTDSLFPGYYQRAEVTADV FDADGFYRTGDIMAEVGPEQFVYLDRRNNVLKLSQGEFVTVSKLEAVFGDSPLVRQIYIY GNSARAYLLAVIVPTQEALDAVPVEELKARLGDSLQEVAKAAGLQSYEIPRDFIIETTPW TLENGLLTGIRKLARPQLKKHYGELLEQIYTDLAHGQADELRSLRQSGADAPVLVTVCRA AAALLGGSASDVQPDAHFTDLGGDSLSALSFTNLLHEIFDIEVPVGVIVSPANDLQALAD YVEAARKPGSSRPTFASVHGASNGQVTEVHAGDLSLDKFIDAATLAEAPRLPAANTQVRT VLLTGATGFLGRYLALEWLERMDLLVDGKLICLVRAKSDTEARARLDKTFDSGDPELLAHY RALAGDHLEVLAGDKGEADLGLDRQTWQRLADTVDLIVDPAALVNHVLPYSQLFGPNALG TAELLRLALTSKIKPYSYTSTIGVADQIPPSAFTEDADIRVISATRAVDDSYANGYSNSK WAGEVLLREAHDLCGLPVAVFRCDMILADTTWAGQLNYPDMFTRMILSLAATGIAPGSFY ELAADGARQRAHYDGLPVEFIAEAISTLGAQSQDGFHTYHVMNPYDDGIGLDEFVDWLNE SGCPIQRIADYGDWLQRFETALRALPDRQRHSSLLPLLHNYRQPERPVRGSIAPTDRFRA AVQEAKIGPDKDIPHVGAPIIVKYVSDLRLLGLL |

FIGURE 10 (Continued)

| SEQ ID NO | Organism | GENBANK reference | Amino acid sequence |
|---|---|---|---|
| 3 | Mycobacterium smegmatis | ABK71854.1 | MTSDVHDATDGVTETALDDEQSTRRIAELYATDPEFAAAAPLPAVVDAAHKPGLRLAEIL QTLFTGYGDRPALGYRARELATDEGGRTVTRLLPRFDTLTYAQVVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDDHRDALAREQLAGKGIAVTTLDAIADEG AGLPAEPIYTADHDQRLAMILYTSGSTGAPKGAMYTEAMVARLWTMSFITGDPTPVINVN FMPLNHLGGRIPISTAVQNGGTSYFVPESDMSTLFEDLALVRPTELGLVPRVADMLYQHH LATVDRLVTQGADELTAEKQAGAELREQVLGGRVITGFVSTAPLAAEMRAFLDITLGAHI VDGYGLTETGAVTRDGVIVRPPVIDYKLIDVPELGYFSTDKPYPRGELLVRSQTLTPGYY KRPEVTASVFDRDGYYHTGDVMAETAPDHLVVDRRNNVLKLAQGEFVAVANLEAVFSGA AIVRQIFVYGNSERSFLLAVVVPTPEALEQYDPAALKAALADSLQRTARDAELQSYEVPA DFIVETEPFSAANGLLSGVGKLLRPNLKDRYGQRLEQMYADIAATQANQLRELRRAAATQ PVIDTLTQAAATILGTGSEVASDAHFTDLGGDSLSALTLSNLLSDFFGFEVPGTIVNPA TNLAQLAQHIEAQRTAGDRRPSFTTVHGADATEIRASELTLDKFIDAETLRAAPGLPKVT TEPRTVLLSGANGWLGRFLTLQWLERLAPVGGTLTIVRGRDDAAARARLTQAYDTDPEL SRRFAELADRHLRVVAGDIGDPNLGLTPEIWHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVPDMFTRLLLSLLITGVAPRS FYIGDGERPRAHYPGLTVDFVAEAVTTLGAQQREGYVSYDVMNPHDDGISLDVFVDWLIR AGHPIDRVDDYDDDWVRRFETALTALPEKRRAQTVLPLLHAFRAPQAPLRGAPEPTEVFHA AVRTAKVGPGDIPHLDEALIDKYIRDLREFGLI |

FIGURE 10 (Continued)

| SEQ ID NO | Organism | GENBANK reference | Amino acid sequence |
|---|---|---|---|
| 4 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYVAVDLAAARS GLVSVPLQAGASLAQLVGILEETEPKVLAASASSLEGAVACALAAPSVQRLVVFDLRGPD ASESAADERRGALADAEEQLARAGRAVVVETLADLAARGEALPEAPLFEPAEGEDPLALL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGFPLLDGYGSTEALGVMRNGIIQRPPVIDYKLVDVPELGYR TTDKPYPRGELCIRSTSLISGYYKRPEITAEVFDAQGYYKTGDVMAEIAPDHLVYVDRSK NVLKLSQGEFVAVAKLEAAYGTSPYVKQIFVYGNSERSFLLAVVVPNAEVLGARDQEEAK PLIAASLQKIAKEAGLQSYEVPRDFLJETEPFTQNGLLSEVGKLLRPKLKARYGEALEA RYDEIAHGQADELRALRDGAGQRPVVETVVRAAVAISGSEGAEVGPEANFADLGGDSLSA LSLANLLHDVFEVEVPVRIIIGPTASLAGIAKHIEAERAGASAPTAASVHGAGATRIRAS ELTLEKFLPEDLLAAAKGLPAADQVRTVLLTGANGWLGRFLALEQLERLARSGQDGGKLJ CLVRGKDAAAARRRIEETLGTDPALAARFAELAEGRLEVVPGDVGEPKFGLDDAAWDRLA EEVDVIVHPAALVNHVLPYHQLFGPNVVGTAEIIRLAITAKRKPVTYLSTVAVAAGVEPS SFEEDGDIRAVVPERPLGDGYANGYGNSKWAGEVLLREAHELVGLPVAVFRSDMILAHTR YTGQLNVPDQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSLLPLLRAYSFPHPPVDGSVYPTGKFQGAVKAAQVGSDHDVPHLGKALIVKYAD DLKALGLL |

FIGURE 10 (Continued)

| SEQ ID NO | Organism | GENBANK reference | Amino acid sequence |
|---|---|---|---|
| 5 | *Mycobacterium smegmatis* | ABK75684.1 | MTIETREDRFNRRIDHLFETDPQFAAARPDEAISAAAADPELRLPAAVKQILAGYADRPA LGKRAVEFVTDEEGRTTAKLLPRFDTITYRQLAGRIQAVTNAWHNHPVNAGDRVAILGFT SVDYTTIDIALLELGAVSVPLQTSAPVAQLQPIVAETEPKVIASSVDFLADAVALVESGP APSRLVVFDYSHEVDDQREAFEAAKGKLAGTGVVVETITDALDRGRSLADAPLYVPDEAD PLTLLIYTSGSTGTPKGAMYPESKTATMWQAGSKARWDETLGVMPSITLNFMPMSHVMGR GILCSTLASGGTAYFAARSDLSTFLEDLALVRPTQLNFVPRIWDMLFQEYQSRLDNRRAE GSEDRAEAAVLEEVRTQLLGGRFVSALTGSAPISAEMKSWVEDLLDMIHLLEGYGSTEAGA VFIDGQIQRPPVIDYKLVDVPDLGYFATDRPYPRGELLVKSEQMFPGYYKRPEITAEMFD EDGYYRTGDIVAELGPDHLEYLDRRNNVLKLSQGEFVTVSKLEAVFGDSPLVRQIYVYGN SARSYLLAVVVPTEEALSRWDGDELKSRISDSLQDAARAAGLQSYEIPRDFLVETTPFTL ENGLLTGIRKLARPKLKAHYGERLEQLYTDLAEGQANELRELRRNGADRPVVETVSRAAV ALLGASVTDLRSDAHFTDLGGDSLSALSFSNLLHEIFDVDVPVGVIVSPATDLAGVAAYI EGELRGSKRPTYASVHGRDATEVRARDLALGKFIDAKTLSAAPGLPRSGTEIRTVLLTGA TGFLGRYLALEWLERMDLVDGKVICLVRARSDDEARARLDATFDTGDATLLEHYRALAAD HLEVIAGDKGEADLGLDHDTWQRLADTVDLIVDPAALVNHVLPYSQMFGPNALGTAELIR IALTTTIKPYVVYSTIGVGQGISPEAFVEDADIREISATRRVDDSYANGYGNSKWAGEVL LREAHDWCGLPVSVFRCDMILADTTYSGQLNLPDMFTRLMLSLVATGIAPGSFYELDADG NRQRAHYDGLPVEFIAEAISTIGSQVTDGFETFHVMNPYDDGIGLDEYVDWLIEAGYPVH RVDDYATWLSRFETALRALPERQRQASLLPLLHNYQQPSPPVCGAMAPTDRFRAAVQDAK IGPDKDIPHVTADVIVKYISNLQMLGLL |

FIGURE 10 (Continued)

| SEQ ID NO | Organism | GENBANK reference | Amino acid sequence |
|---|---|---|---|
| 6 | Mycobacterium massiliense | EIV11143.1 | MTNETNPQQEQLSRRIESLRESDPQFRAAQPDPAVAEQVLRPGLHLSEAIAALMTGYAER PALGERARELVIDQDGRTTLRLLPRFDTTYGELWSRTSVAAAWHHDATHPVKAGDLVA TLGFTSIDYTVLDLAIMILGGVAVPLQTSAPASQWTTILAEAEPNTLAVSIELIGAAMES VRATPSIKQVVVFDYTPEVDDQREAFEAASTQLAGTGIALETLDAVIARGAALPAAPLYA PSAGDDPLALLIYTSGSTGAPKGAMHSENIVRRWWIREDVMAGTENLPMIGLNFMPMSHI MGRGTLTSTLSTGGTGYFAASSDMSTLFEDMELIRPTALALVPRVCDMVFQRFEQTEVDRR LASGDTASAEAVAAEVKADIRDNLFGGRVSAVMVGSAPLSEELGEFIESCFELNLTDGYG STEAGMVFRDGIVQRPPVIDYKLVDVPELGYFSTDKPHPRGELLLKTDGMFLGYYKRPEV TASVFDADGFYMTGDIVAELAHDNIEIIDRRNNVLKLSCQGEFVAVATLEAEYANSPVVHQ IYVYGSSERSYLLAVVVPTPEAVAAAKGDAAALKTTIADSLQDIAKEIQLQSYEVPRDFI IEPQPPTQGNGLLTGIAKLARPNLKAHYGPRLEQMYAEIAEQQAAELRALHGVDPDKPAL ETVLKAAQALLGVSSAELAADAHFTDLGGDSLSALSFSDLLRDIFAVEVPVGVIVSAAND LGGVAKFVDEQRHSGGTRPTAETVHGAGHTEIRAADLTLDKFIDEATLHAAPSLPKAAGI PHTVLLTGSNGYLGHYLALEWLERLDKTDGKLIVIVRGKNAEAAYGRLEEAFDTGDTELL AHFRSLADKHLEVLAGDIGOPNLGLDADTWQRLADTVDVIVHPAALVNHVLPYNQLFGPN VVGTAEIIKLAITTKIKPVTYLSTVAVAAYVDPTTFDEESDIRLISAVRPIDDGYANGYG NAKWAGEVLLREAHDLCGLPVAVFRSDMILAHSRYTGQLNVPDQFTRLILSLIATGIAPG SFYQAQTTGERPLAHYDGLPGDFTAEAITTLGTQVPEGSEGFVTYDCVNPHADGISLDNF VDWLIEAGYPIARIDNYTEWFTRFDTAIRGLSEKQKQHSLLPLLHAFEQPSAAENHGVVP AKRFQHAVQAAGIGPVGQDGTTDIPHLSRRLIVKYAKDLEQLGLL |

FIGURE 10 (Continued)

| SEQ ID NO | Organism | GENBANK reference | Amino acid sequence |
|---|---|---|---|
| 7 | Segniliparus rotundus | ADG98140.1 | MTQSHTQGPQASAAHSRLARRAAELLATDPQAAATLPDPEVVRQATRPGLRLAERVDAIL SGYADRPALGQRSFQTVKDPITGRSSVELLPTFDTITYRELRERATAIASDLAHHPQAPA KPGDFLASIGFISVDVVAIDIAGVFAGLTAVPLQTGATLATLTAITAETAPTLFAASIEH LPTAVDAVLATPSVRRLLVFDYRAGSDEDREAVEAAKRKIADAGSSVLVDVLDEVIARGK SAPKAPLPPATDAGDDSLSLLIYTSGSTGTPKGAMYPERNVAHFWGGVWAAAPDEDAAPP VPAINITFLPLSHVASRLSLMPTLARGGLMHFVAKSDLSTLFEDLKLARPTNLFLVPRVV EMLYQHYQSELDRRGVQDGTREAEAVKDDLRTGLLGGRILTAGFGSAPLSAELAGRIESL LQIHLVDGYGSTEAGPVWRDGYLVKPPVTDYKLIDVPELGYFSTDSPHPRGELAIKTQTI LPGYYKRPETTAEVFDEDGPYLTGDVVAQIGPEQFAYVDRRKNVLKLSQGEFVTLAKLEA AVSSPLVRQLFVYGSSERSYLLAVIVPTPDALKKFGVGEAAKAALGESLQKIARDEGLQ SYEVPRDFHETDPFTVENGLLSDARKSLRPKLKEHYGERLEAMYKELADGQANELRDIR RGVQQRPTLETVRRAAAAMLGASAAEIKPDAHFTDLGGDSLSALTFSNFLHDLFEVDVPV GVIVSAANTLGSVAEHIDAQLAGGRARPTFATVHGKGSTTIKASDLTLDKFIDEQTLEAA KHLPKPADPPRTVLLTGANGWLGRFLALEWLERLAPAGGKLITIVRGKDAAQAKARLDAA YESGDPKLAGHYQDLAATTLEVLAGDFSEPRLGLDEATWNRLADEVDFISHPGALVNHVL PYNQLFGPNVAGVAEIIKLAITTRIKPVTYLSTVAVAAGVEPSALDEDGDIRTVSAERSV DEGYANGYGNSKWGGEVLREAHDRTGLPVRVFRSDMILAHQKYTGQVNATDQFTRLVQS LLATGLAPKSFYELDAQGNRQRAHYDGIPVDFTAESITTLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDIKQLGLL |
| 8 | Chromobacterium violaceum | AAQ59697.1 | MQKQRTTSQWRELDAAHHLHPFTDTASLNQAGARVMTRGEGVYLWDSEGNKIIDGMAGLW CVNVGYGRKDFAEAARRQMEELPFYNTFFKTTHPAVVELSSLLAEVTPAGFDRVFYTNSG SESVDTMIRMVRRYWDVQGKPEKKTLIGRWNGYHGSTIGGASLGGMKYMHEQGDLPIPGM AHIEQPWWYKHGKDMTPDEFGVVAARWLEEKILEIGADKVAAFVGEPIQGAGGVIVPPAT YWPEIERICRKYDVLLVADEVICGFGRTGEWFGHQHFGFQPDLFTAAKGLSSGYLPIGAV FVGKRVAEGLIAGGDFNHGFTYSGHPVCAAVAHANVAALRDEGIVQRVKDDIGPYMQKRW RETFSRFEHVDDVRGVGMVQAFTLVKNKAKRELFPDFGEIGTLCRDIFFRNNLIMRACGD HIVSAPPLVMTRAEVDEMLAVAERCLEEFEQTLKARGLA |

FIGURE 10 (Continued)

| SEQ ID NO | Organism | GENBANK reference | Amino acid sequence |
|---|---|---|---|
| 9 | Pseudomonas aeruginosa | AAG08191.1 | MNARLHATSPLGDADLVRADQAHYMHGYHVFDDHRVNGSLNIAAGDGAYIYDTAGNRYLD AVGGMWCTNIGLGREEMARTVAEQTRLLAYSNPFCDMANPRAIELCRKLAELAPGDLDHV FLTTGGSTAVDTAIRLMHYYQNCRGKRAKKHVITRINAYHGSTPLGMSLGGKSADRPAEF DFLDERIHHLACPYYYRAPEGLGEAEFLDGLVDEFERKLELGADRVGAFISEPVFGSGG VIVPPAGYHRRMWELCQRYDVLYISDEVVTSFGRLGHFFASQAVFGVQPDIILTAKGLTS GYQPLGACIFSRRIWEVIAEPDKGRCFSHGFTYSGHPVACAAALKNEIIEREGLLAHAD EVGRYFEERLQSLRDLPIVGDVRGMRFPMACVEFVADKASKALFPESLNIGEWVHLRACQKR GLLVRPIVHLNVMSPPLLITREQVDTVVRVLRESIEETVEDLVRAGHR |
| 10 | Pseudomonas syringae | AAY39893.1 | MSANNPQTLEWQALSSEHHLAPFSDYKQLKEKGPRIITRAEGVYLWDSEGNKILDGMSGL WCVAIGYGREELADAASKQMRELPYYNLFFQTAHPPVLELAKAISDIAPEGMNHVFFTGS GSEGNDTMLRMVRHYWALKGQPNKKTIISRVNGYHGSTVAGASLGGMTYMHEQGDLPIPG VVHPQPYWFGEGGDMTPDEFGIWAAEQLEKKILFLGVENVGAFIAEPIQGAGGVIVPPD SYWPKIKEILSRYDILFAADEVICGFGRTSEWFGSDFYGLRPDMMTIAKGLTSGYVPMGG LIVRDEIVAVLNEGGDFNHGFTYSGHPVAAAVALENIRILREEKIVERVRSETAPYLQKR LRELSDHPLVGEVRGVGLLGAIELVKDKTTRERYTDKGAGMICRTFCFDNGLIMRAVGDT MIIAPPLVISFAQIDELVEKARTCLDLTLAVLQG |
| 11 | Rhodobacter sphaeroides | ABA81135.1 | MTRNDATNAAGAVGAAMRDHILLPACQEMAKLGKSAQPVLTHAEGIYVHTEDGRRLIDGPA GMWCAQVGYGRREIVDAMAHQAMVLPYASPWYMATSPAARLAEKIATLTPGDLNRIFFTT GGSTAVDSALRFSEFYNNVLGRPQKKRIHVRYDGYHGSTALTAACTGRTGNWPNFDIAQD RISFLSSPNPRHAGNRSQEAFLDDLVQEFEDRIESLGPDTIAAFLAEPILASGGVIIPPA GYHARFKAICEKHDILYISDEVVTGFGRCGEWFASEKVFGVVPDIITFAKGVTSGYVPLG GLAISEAVLARISGENAKGSWFTNGYTYSNQPVACAAALANIELMEREGIVDQAREMADY FAAALASLRDLPGVAETRSVGLVGCVQCLLDPTRADGTAEDKAFTLKIDERCFELGLIVR PLGDLCVISPPLIISRAQIDEMVAIMRQAITEVSAAHGLTAKEPAAV |
| 12 | Escherichia coli | AAA57874.1 | MNRLPSSASALACSAHALNLIEKRTLDHEEMKALNREVIEYFKEHVNPGFLEYRKSVTAG GDYGAVEWQAGSLNTLVDTQGQEFIDCLGGFGIFNVGHRNPVVVSAVQNQLAKQPLHSQE LLDPLRAMLAKTLAALTPGKLKYSFFCNSGTESVEAALKLAKAYQSPRGKFTFIATSGAF HGKSLGALSATAKSTFRKPFMPLLPGFRHVPFGNIEAMRTALNECKKTGDDVAAVILEPI QGEGGVILPPPGYLTAVRKLCDEFGALMILDEVQTGMGRTGKMFACEHENVQPDILCLAK ALGGGVMPIGATIATEEVFSVLFDNPFLHTTTFGGNPLACAAALATINVLLEQNLPAQAE QKGDMLLDGFRQLAREYPDLVQEARGKGMLMAIEFVDNEIGYNFASEMFRQRVLAGTLN NAKTIREPPLTLTIEQCELVIKAARKALAAMRVSVEEA |

FIGURE 10 (Continued)

| SEQ ID NO | Organism | GENBANK reference | Amino acid sequence |
|---|---|---|---|
| 13 | Vibrio Fluvialis | AEA39183.1 | MNKPQSWEARAETYSLYGFTDMPSLHQRGTVVTHGEGPYIVDVNGRRYLDANSGLWNMV AGFDHKGLIDAAKAQYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETEEQFVARLARELEETIQREGADTIAGFFAEPVMGAGGVIPPAKGYFQ AILPILRKYDIPVISDEVICGFGRTGNTWGCVTYDFTPDAIISSKNLTAGFFPMGAVILG PELSKRLETAIEAIEEFPHGFTASGHPVGCAIALKAIDVVMNEGLAENVRRLAPRFEERL KHIAERPNIGEYRGIGFMWALEAVKDKASKTPFDGNLSVSERIANTCTDLGLICRPLGQS VVLCPPFILTEAQMDEMFDKLEKALDKVFAEVA |
| 14 | Bacillus subtilis | CAA44858.1 | MKIYGIYMDRPLSQEENERFMSFISPEKREKCRRFYHKEDAHRTLLGDVLVRSVISRQYQ LDKSDIRFSTQEYGKPCIPDLPDAHFNISHSGRWVICAFDSQPIGIDIEKTKPISLEIAK RFFSKTEYSDLLAKDKDEQTDYFYHLWSMKESFIKQEGKGLSLPLDSFSVRLHQDGQVSI ELPDSHSPCYIKTYEVDPGYKMAVCAAHPDFPEDITMVSYEELL |
| 15 | Nocardia sp. NRRL 5646 | ABI83656.1 | MIETILPAGVESAEILEYPEDLKAHPAEEHLIAKSVEKRRRDFIGARHCARLALAELGEP PVAIGKGERGAPIWPRGVVGSLTHCDGYRAAAVAHKMRFRSIGIDAEPHATLPEGVLDSV SLPPEREWLKTTDSALHLDRLLFCAKEATYKAWWPLTARWLGFEEAHITFEIEDGSADSG NGTFHSELLVPGQTNDGGTPLLSFDGRWLIADGFILTAIAYA |

FIGURE 10 (Continued)

| SEQ ID NO | Organism | GENBANK reference | Amino acid sequence |
|---|---|---|---|
| 16 | Azotobacter vinelandii | CAA36680.1 & CAA36678.1 & CAA36679.1 | MQDSVMQRMWNSAHLSGGNAAYVEELYELYLHDPNAVPEEWRTYFEKLPAEAGTSTDVPH APVRDQFVLLAKNQRRAQPVATSSVSTEHEKKQVEVLRLIQAYRTRGHQASQLDPLGLWQ RTAPSDLSITHYGLTNADLDTPFRTGELYIGKEEATLREILQALQETYCRTIGAEFTHIV DSEQRNWFAQRLESVRGRPVYSKEAKSHLLERLSAAEGLEKYLGTKYPGTKRFGLEGGES LVPVVDEIIQRSGSYGTKEVIGMAHRGRLNLLVNALGKNPRDLFDEFFGKHLVELGSGD VKYHQGFSSNWMTSGGEVHLAMAFNPSHLEIVSPVVEGSVRARQDRRVDATGEKVVPISI HGDSAFAGQGVVMETFQMSQIRGYKTGGTIHVVNNQVGFTTSNPVDTRSTEYCTDPAKM IQAPVLHVNGDDPEAVLFVTQLAVDYRMQFKRDVVIDLVCYRRRGHNEADEPSGTQPLMY QKIAKQPTTRELYADALVKEGSLSQEEVQAKVDEYRTALDNGQHVLKSLVKEPNTELFVD WTPYLGHAWTARHDTSFELKTLQELNAKLLQIPEGFVVQRQVAKILEDRGRMGVGAMPIN WGCAETLAYATLLKEGHPVRITGQDVGRGTFSHRHAALHNQKDASRYIPLQNLYEGQPKF ELYDSFLSEEAVLAFEYGYATTTPNALVIIWEASSGDFANGAQVVIDQFISSGETKWGALC GLTMLLPHGYEGQGPEHSSARLERYLQLCAEQNIQVCVPTTPAQVYHMLRRQVIRPLRKP LVALTPKSLLRHKSAISTLEDLALGSFHPVLPEVDSLDPKKVERLVLCSGKVYYDLLDKR HAEGREDIAIVRIEQLYPPEEELAEVMAPYTNLKHVVWCQEEPMNQGAWYCSQHHMRRV ASAHKKELFLQYAGREASAAPACGYASMHAEQQEKLLQDAFTV MAIDIKAPTFPESIADGTVATWHKKPGEPVKRDELIVDIETDKVVMEVLAEADGVIAEIV KNEGDTVLSGELLGKLTEGGAATAAPAAAPAPAAAAPAAAEAPILSPAARKIAEENAIAA DSITGTGKGGRVTKEDAVAAAEAKKSAPAGQPAPAATAAPLFAAGDRVEKRVPMTRLRAK VAERLVEAQSSMAMLTTFNEVNMKPVMELRAKYKDLFEKTHNGVRLGFMSFFVKAAVEAL KRQPGVNASIDGNDIVYHGYQDIGVAVSSDRGLVVPVLRNAEFMSLAEIEGGINEFGKKA KAGKLTIEEMTGGTFTISNGGVFGSLLSTPIVNPPQTAILGMHKIQERPMAVNGQVVILP MMVYLALSYDHRLIDGKEAVTFLVTMKDLLEDPARLLLDV MSQKFDVIVIGAGPGGYVAAIKSAQLGLKTALIEKYKGKEGKTALGGTCLNVGCIPSKAL LDSSYKFHEAHESFKLHGISTGEVAIDVPTMIARKDQIVRNLTGGVASLIKANGVTLFEG HGKLLAGKKVEVTAADGSSQVLDTENVILASGSKPVEIPPAPVDQDVIVDSTGALDFQNV PGKLGVIGAGVIGLELGSVWARLGAEVTVLEAMDKFLPAVDEQVAKEAQKILTKQGLKIL LGARVTGTEVKNKQVTVKFVDAEGEKSQAFDKLIVAVGRRPVTTDLLAADSGVTLDERGF IVVDDYCATSVPGVYAIGDVVRGAMLAHKASEEGVVVAERIAGHKAQMNYDLIPAVIYTH PEIAGVGKTEQALKAEGVAINVGVFPFAASGRAMAANDTAGFVKVIADAKTDRVLGVHVI GPSAAELVQQGAIAMEFGTSAEDLGMMVFAHPALSEALHEAALAVSGHAIHVANRKK |

FIGURE 10 (Continued)

| SEQ ID NO | Organism | GENBANK reference | Amino acid sequence |
|---|---|---|---|
| 17 | Lactobacillus brevis | ABJ63754.1 | MAANEFSETHRVVYYEADDTGQLTLAMLINLFVLVSEDQNDALGLSTAFVQSHGVGWVVT QYHLHIDELPRTGAQVTIKTRATAYNRYFAYREYWLLDDAGQVLAYGEGIWVTMSYATRK ITTIPAEVMAPYHSEEQTRLPRLPRPDHFDEAVNQTLKPYTVRYFDIDGNGHVNNAHYFD WMLIDVLPATFLRAHHPTDVKIRFENEVQYGHQVTSELSQAAALTTQHMIKVGDLTAVKAT IQWDNR |
| 18 | Lactobacillus plantarum | CCC78182.1 | MATLGANASLYSEQHRITYYECDRTGRATLTTLJDIAVLASEDQSDALGLTTEMVQSHGV GWVVTQYAIDITRMPRQDEVVTIAVRGSAYNPYFAYREFWIRDADGQQLAYITSIWVMMS QTTRRIVKILPELVAPYQSEVVKRIPRLPRPISFEATDTTITKPYHVRFFDIDPNRHVNN AHYFDWLVDTLPATFLLQHDLVHVDVRYENEVKYGQTVTAHANILPSEVADQVTTSHLIE VDDEKCCEVTIQWRTLPEPIQ |
| 19 | Escherichia coli | AAA23833.1 | MDQKLLTDFRSELLDSRFGAKAISTIAESKRFPLHEMRDDVAFQJINDELYLDGNARQNL ATFCQTWDDENVHKLMDLSINKNWIDKEEYPQSAAIDLRCVNMVADLWHAPAPKNGQAVG TNTIGSSEACMLGGMAMKWRWRKRMEAAGKPTDKPNLVCGPVQICWHKFARYWDVELREI PMRPGQLFMDPKRMIEACDENTIGVVPTFGVTYTGNYEFPQPLHDALDKFQADTGIDIDM HIDAASGGFLAPFVAPDIVWDFRLPRVKSISASGHKFGLAPLGCGWVIWRDEEALPQELV FNVDYLGGQJGTFAINFSRPAGOVIAQYYEFLRLGREGYTKVQNASYQVAAYLADEIAKL GPYEFICTGRPDEGIPAVCFKLKDGEDPGYTLYDLSERLRLRGWQVPAFTLGGEATDIVV MRIMCRRGFEMDFAELLLEDYKASLKYLSDHPKLQGIAQQNSFKHT |
| 20 | Escherichia coli | AAA23536.1 | MNVIAILNHMGVYFKEEPIRELHRALERLNFQJVYPNDRDDLLKLJENNARLCGVIFDWD KYNLELCEEISKMNENLPLYAFANTYSTLDVSLNDLRLQJSFFEYALGAAEDIANKIKQT TDEYINTILPPLTKALFKYVREGKYTFCTPGHMGGTAFQKSPVGSLFYDFFGPNTMKSDI SISVSELGSLLDHSGPHKEAEQYIARVFNADRSYMVTNGTSTANKIVGMYSAPAGSTILI DRNCHKSLTHLMMMSDVTPIYFRPTRNAYGILGGIPQSEFQHATIAKRVKETPNATWPVH AVITNSTYDGLLYNTDFIKKTLDVKSIHFDSAWVPYTNFSPIYEGKCGMSSGRVEGKVIY ETQSTHKLLAAFSQASMIHVKGDVNEETFNEAYMMHTTTSPHYGIVASTETAAAMMKGNA GKRRLINGSIERAIKFRKEIKRLRTESDGWFFDVWQPDHIDTTECWPLRSDSTWHGFKNID NEHMYLDPIKVTLLTPGMEKDGTMSDFGIPASIVAKYLDEHGIVVEKTGPYNLLFLSIG IDKTKALSLLRALTDFKRAFDLNLRVKNMLPSLYREDPEFYENMRIQELAQNIHKLIVHH NLPDLMYRAFEVLPTMVMTPYAAFQKELHGMTEEVYLDEMVGRINANMILPYPPGVPLVM PGEMITEESRPVLEFLQMLCEIGAHYPGFETDIHGAYRQADGRYTVKVLKEESKK |

FIGURE 10 (Continued)

| SEQ ID NO | Organism | GENBANK reference | Amino acid sequence |
|---|---|---|---|
| 21 | Escherichia coli | AAA62785.1 | MSKLKIAVSDSCPDCFTTQRECYINESRNIDVAAIVLSLNDVTCGKLDEIDATGYGIPV FIATENQERVPAEYLPRISGVFENCESRREFYGRQLETAASHYETQLRPPFFRALVDYVN QGNSAFDCPGHQGGEFFRRHPAGNQFVEYFGEALFRADLCNADVAMGDLLIHEGAPCIAQ QHAAKVFNADKTYFVLNGTSSSNKVVLNALLTPGDLVLFDRNNHKSNHHGALLQAGATPV YLETARNPYGFIGGIDAHCFEESYLRELIAEVAPQRAKEARPFRLAVIQLGTYDGTIYNA RQVVDKIGHLCDYILFDSAWVGYEQFPMMADCSPLLLDLNENDPGILVTQSVHKQQAGF SQTSQIHKKDSHKGQQRYVPHKRMNNAFMMHASTSPFYPLFAALNINAKMHEGVSGRNM WMDCVVNGINARKLILDNCQHIRPFVPELVDGKPWOSYETAQJAVDLRFFQFVPGEHWHS FEGYAENQYFVDPCKLLLTPGIDARNGEYEAFGVPATILANFLRENGVVPEKCDLNSIL FLLTPAEDMAKLQQLVALLVRFEKLLESDAPLAEVLPSIYKQHEERYAGYTLRQLCQEMH DLYARHNVKQLQKEMFRKEHFPRVSMNPQEANYAYLRGEVELVRLPDAEGRIAAEGALPY PPGVLCVVPGEIWGGAVLRYFSALEEGINILPGFAPELQGVYIEEHDGRKQVWCYVIKPR DAQSTLLKGEKL |
| 22 | Escherichia coli | BAA21656.1 | MNIIAIMGPHGVFYKDEPIKELESALVAQGFQIIWPQNSVDLLKFIEHNPRICGVIFDWD EYSLDLCSDINQLNEYLPLYAFINTHSTMDVSVQDMRMALWFFEYALGQAEDIAIRMRQY TDEYLDNITPPFTKALFTYVKERKYTFCTPGHMGGTAYQKSPVGCLFYDFFGGNTLKADV SISVTELGSLLDHTGPHLEAEEYIARTFGAEQSYIVTNGTSTSNKIVGMYAAPSGSTLLI DRNCHKSLAHLLMMNDVVPVWLKPTRNALGILGGIPRREFTRDSIEEKVAATTQAQWPVH AVITNSTYDGLLYNTDWIKQTLDVPSIHFDSAWVPYTHFHPIYQGKSGMSGERVAGKVIF ETQSTHKMLAALSQASLIHKGEYDEEAFNEAFMMHTTTSPSYPIVASVETAAAMLRGNP GKRLINRSVERALHFRKEVQRLREESDGWFFDIWQPPQVDEAECWPVAPGEQWHGFNDAD ADHMFLDPVKVTILTPGMDEQGNMSEEGIPAALVAKFLDERGIVVEKTGPYNLLFLFSIG IDKTKAMGLLRGLTEFKRSYDLNLRIKNMLPDLYAEDPFYRNMRIQDLAQGIHKLIRKH DLPGLMLRAFDTLPEMIMTPHQAWQRQIKGEVETIALEQLVGRVSANMILPYPPGVPLLM PGEMLTKESRTVLDFLLMLCSVGQHYPGFETDIHGAKQDEDGVYRVRVLKMAG |

```
                        SEQUENCE LISTING

<160> NUMBER OF SEQ ID NOS: 22

<210> SEQ ID NO 1
<211> LENGTH: 550
<212> TYPE: PRT
<213> ORGANISM: Salmonella typhimurium

<400> SEQUENCE: 1

Met Gln Asn Pro Tyr Thr Val Ala Asp Tyr Leu Leu Asp Arg Leu Ala
 1               5                  10                  15

Gly Cys Gly Ile Gly His Leu Phe Gly Val Pro Gly Asp Tyr Asn Leu
                20                  25                  30

Gln Phe Leu Asp His Val Ile Asp His Pro Thr Leu Arg Trp Val Gly
            35                  40                  45

Cys Ala Asn Glu Leu Asn Ala Ala Tyr Ala Ala Asp Gly Tyr Ala Arg
        50                  55                  60

Met Ser Gly Ala Gly Ala Leu Leu Thr Thr Phe Gly Val Gly Glu Leu
65                  70                  75                  80

Ser Ala Ile Asn Gly Ile Ala Gly Ser Tyr Ala Glu Tyr Val Pro Val
                85                  90                  95

Leu His Ile Val Gly Ala Pro Cys Ser Ala Ala Gln Gln Arg Gly Glu
            100                 105                 110

Leu Met His His Thr Leu Gly Asp Gly Asp Phe Arg His Phe Tyr Arg
        115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
            180                 185                 190

Gly Val Glu Thr Ala Phe Arg Tyr His Ala Arg Gln Cys Leu Met Asn
        195                 200                 205

Ser Arg Arg Ile Ala Leu Leu Ala Asp Phe Leu Ala Gly Arg Phe Gly
    210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
            260                 265                 270

Ala Ile Glu Asp Ala Asp Arg Val Ile Cys Val Gly Thr Arg Phe Val
        275                 280                 285

Asp Thr Leu Thr Ala Gly Phe Thr Gln Gln Leu Pro Ala Glu Arg Thr
    290                 295                 300
```

```
Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
            325                 330                 335

Cys Ala Phe Ala Pro Pro Thr Arg Ser Ala Gly Gln Pro Val Arg
                340                 345                 350

Ile Asp Lys Gly Glu Leu Thr Gln Glu Ser Phe Trp Gln Thr Leu Gln
            355                 360                 365

Gln Tyr Leu Lys Pro Gly Asp Ile Ile Leu Val Asp Gln Gly Thr Ala
            370                 375                 380

Ala Phe Gly Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Ile Gly
            420                 425                 430

Asp Gly Ala Ala Gln Leu Thr Ile Gln Glu Met Gly Ser Met Leu Arg
            435                 440                 445

Asp Gly Gln Ala Pro Val Ile Leu Leu Leu Asn Asn Asp Gly Tyr Thr
450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
            500                 505                 510

Glu Arg Leu Ala Arg Pro Gln Arg Leu Ser Phe Ile Glu Val Met Leu
515                 520                 525

Pro Lys Ala Asp Leu Pro Glu Leu Leu Arg Thr Val Thr Arg Ala Leu
530                 535                 540

Glu Ala Arg Asn Gly Gly
545                 550

<210> SEQ ID NO 2
<211> LENGTH: 1174
<212> TYPE: PRT
<213> ORGANISM: Mycobacterium marinum

<400> SEQUENCE: 2

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125
```

```
Ile Asp Met Thr Leu Ala Arg Leu Gly Ala Val Ala Val Pro Leu Gln
130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
        195                 200                 205

Arg Leu Ala Gly Ser Ala Val Val Glu Thr Leu Ala Glu Ala Ile Ala
210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
        275                 280                 285

Thr Leu Asn Phe Met Pro Met Ser His Val Met Gly Arg Gln Ile Leu
290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
        355                 360                 365

Glu Ala Gln Val Lys Ala Glu Ile Arg Asn Asp Val Leu Gly Gly Arg
370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
        435                 440                 445

Leu Thr Asp Arg Pro His Pro Arg Gly Glu Leu Leu Val Lys Thr Asp
450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
530                 535                 540
```

-continued

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
            565                 570                 575

Glu Val Ala Lys Ala Ala Gly Leu Gln Ser Tyr Glu Ile Pro Arg Asp
                580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
        610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
        675                 680                 685

Leu Ser Phe Thr Asn Leu Leu His Glu Ile Phe Asp Ile Glu Val Pro
690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
        755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
        835                 840                 845

Glu Val Leu Ala Gly Asp Lys Gly Glu Ala Asp Leu Gly Leu Asp Arg
850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
        915                 920                 925

Pro Pro Ser Ala Phe Thr Glu Asp Ala Asp Ile Arg Val Ile Ser Ala
            930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu

```
                        965                 970                 975
Pro Val Ala Val Phe Arg Cys Asp Met Ile Leu Ala Asp Thr Thr Trp
                980                 985                 990

Ala Gly Gln Leu Asn Val Pro Asp Met Phe Thr Arg Met Ile Leu Ser
                995                 1000                1005

Leu Ala Ala Thr Gly Ile Ala Pro Gly Ser Phe Tyr Glu Leu Ala Ala
                1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Asp Gly Ile Gly Leu Asp
                1060                1065                1070

Glu Phe Val Asp Trp Leu Asn Glu Ser Gly Cys Pro Ile Gln Arg Ile
                1075                1080                1085

Ala Asp Tyr Gly Asp Trp Leu Gln Arg Phe Glu Thr Ala Leu Arg Ala
                1090                1095                1100

Leu Pro Asp Arg Gln Arg His Ser Ser Leu Leu Pro Leu Leu His Asn
1105                1110                1115                1120

Tyr Arg Gln Pro Glu Arg Pro Val Arg Gly Ser Ile Ala Pro Thr Asp
                1125                1130                1135

Arg Phe Arg Ala Ala Val Gln Glu Ala Lys Ile Gly Pro Asp Lys Asp
                1140                1145                1150

Ile Pro His Val Gly Ala Pro Ile Ile Val Lys Tyr Val Ser Asp Leu
                1155                1160                1165

Arg Leu Leu Gly Leu Leu
                1170

<210> SEQ ID NO 3
<211> LENGTH: 1173
<212> TYPE: PRT
<213> ORGANISM: Mycobacterium smegmatis

<400> SEQUENCE: 3

Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
                20                  25                  30

Asp Pro Glu Phe Ala Ala Ala Pro Leu Pro Ala Val Val Asp Ala
            35                  40                  45

Ala His Lys Pro Gly Leu Arg Leu Ala Glu Ile Leu Gln Thr Leu Phe
        50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
                100                 105                 110

Ala Ala Leu Arg His Asn Phe Ala Gln Pro Ile Tyr Pro Gly Asp Ala
            115                 120                 125

Val Ala Thr Ile Gly Phe Ala Ser Pro Asp Tyr Leu Thr Leu Asp Leu
        130                 135                 140

Val Cys Ala Tyr Leu Gly Leu Val Ser Val Pro Leu Gln His Asn Ala
145                 150                 155                 160
```

```
Pro Val Ser Arg Leu Ala Pro Ile Leu Ala Glu Val Glu Pro Arg Ile
            165                 170                 175

Leu Thr Val Ser Ala Glu Tyr Leu Asp Leu Ala Val Glu Ser Val Arg
        180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
            245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
        290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
    435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
```

-continued

```
            580                 585                 590
Leu Gln Ser Tyr Glu Val Pro Ala Asp Phe Ile Val Glu Thr Glu Pro
            595                 600                 605
Phe Ser Ala Ala Asn Gly Leu Leu Ser Gly Val Gly Lys Leu Leu Arg
            610                 615                 620
Pro Asn Leu Lys Asp Arg Tyr Gly Gln Arg Leu Glu Gln Met Tyr Ala
625                 630                 635                 640
Asp Ile Ala Ala Thr Gln Ala Asn Gln Leu Arg Glu Leu Arg Arg Ala
                    645                 650                 655
Ala Ala Thr Gln Pro Val Ile Asp Thr Leu Thr Gln Ala Ala Ala Thr
                    660                 665                 670
Ile Leu Gly Thr Gly Ser Glu Val Ala Ser Asp Ala His Phe Thr Asp
                    675                 680                 685
Leu Gly Gly Asp Ser Leu Ser Ala Leu Thr Leu Ser Asn Leu Leu Ser
            690                 695                 700
Asp Phe Phe Gly Phe Glu Val Pro Val Gly Thr Ile Val Asn Pro Ala
705                 710                 715                 720
Thr Asn Leu Ala Gln Leu Ala Gln His Ile Glu Ala Gln Arg Thr Ala
                    725                 730                 735
Gly Asp Arg Arg Pro Ser Phe Thr Thr Val His Gly Ala Asp Ala Thr
                    740                 745                 750
Glu Ile Arg Ala Ser Glu Leu Thr Leu Asp Lys Phe Ile Asp Ala Glu
            755                 760                 765
Thr Leu Arg Ala Ala Pro Gly Leu Pro Lys Val Thr Thr Glu Pro Arg
770                 775                 780
Thr Val Leu Leu Ser Gly Ala Asn Gly Trp Leu Gly Arg Phe Leu Thr
785                 790                 795                 800
Leu Gln Trp Leu Glu Arg Leu Ala Pro Val Gly Gly Thr Leu Ile Thr
                    805                 810                 815
Ile Val Arg Gly Arg Asp Asp Ala Ala Ala Arg Ala Arg Leu Thr Gln
                    820                 825                 830
Ala Tyr Asp Thr Asp Pro Glu Leu Ser Arg Arg Phe Ala Glu Leu Ala
            835                 840                 845
Asp Arg His Leu Arg Val Val Ala Gly Asp Ile Gly Asp Pro Asn Leu
            850                 855                 860
Gly Leu Thr Pro Glu Ile Trp His Arg Leu Ala Ala Glu Val Asp Leu
865                 870                 875                 880
Val Val His Pro Ala Ala Leu Val Asn His Val Leu Pro Tyr Arg Gln
                    885                 890                 895
Leu Phe Gly Pro Asn Val Val Gly Thr Ala Glu Val Ile Lys Leu Ala
                    900                 905                 910
Leu Thr Glu Arg Ile Lys Pro Val Thr Tyr Leu Ser Thr Val Ser Val
            915                 920                 925
Ala Met Gly Ile Pro Asp Phe Glu Glu Asp Gly Asp Ile Arg Thr Val
            930                 935                 940
Ser Pro Val Arg Pro Leu Asp Gly Gly Tyr Ala Asn Gly Tyr Gly Asn
945                 950                 955                 960
Ser Lys Trp Ala Gly Glu Val Leu Leu Arg Glu Ala His Asp Leu Cys
                    965                 970                 975
Gly Leu Pro Val Ala Thr Phe Arg Ser Asp Met Ile Leu Ala His Pro
                    980                 985                 990
Arg Tyr Arg Gly Gln Val Asn Val Pro Asp Met Phe Thr Arg Leu Leu
            995                 1000                1005
```

-continued

Leu Ser Leu Leu Ile Thr Gly Val Ala Pro Arg Ser Phe Tyr Ile Gly
         1010                1015                1020

Asp Gly Glu Arg Pro Arg Ala His Tyr Pro Gly Leu Thr Val Asp Phe
1025                1030                1035                1040

Val Ala Glu Ala Val Thr Thr Leu Gly Ala Gln Gln Arg Glu Gly Tyr
             1045                1050                1055

Val Ser Tyr Asp Val Met Asn Pro His Asp Asp Gly Ile Ser Leu Asp
             1060                1065                1070

Val Phe Val Asp Trp Leu Ile Arg Ala Gly His Pro Ile Asp Arg Val
             1075                1080                1085

Asp Asp Tyr Asp Asp Trp Val Arg Arg Phe Glu Thr Ala Leu Thr Ala
         1090                1095                1100

Leu Pro Glu Lys Arg Arg Ala Gln Thr Val Leu Pro Leu Leu His Ala
1105                1110                1115                1120

Phe Arg Ala Pro Gln Ala Pro Leu Arg Gly Ala Pro Glu Pro Thr Glu
                 1125                1130                1135

Val Phe His Ala Ala Val Arg Thr Ala Lys Val Gly Pro Gly Asp Ile
             1140                1145                1150

Pro His Leu Asp Glu Ala Leu Ile Asp Lys Tyr Ile Arg Asp Leu Arg
         1155                1160                1165

Glu Phe Gly Leu Ile
    1170

<210> SEQ ID NO 4
<211> LENGTH: 1148
<212> TYPE: PRT
<213> ORGANISM: Segniliparus rugosus

<400> SEQUENCE: 4

Met Gly Asp Gly Glu Glu Arg Ala Lys Arg Phe Phe Gln Arg Ile Gly
 1               5                  10                  15

Glu Leu Ser Ala Thr Asp Pro Gln Phe Ala Ala Ala Pro Asp Pro
             20                  25                  30

Ala Val Val Glu Ala Val Ser Asp Pro Ser Leu Ser Phe Thr Arg Tyr
             35                  40                  45

Leu Asp Thr Leu Met Arg Gly Tyr Ala Glu Arg Pro Ala Leu Ala His
     50                  55                  60

Arg Val Gly Ala Gly Tyr Glu Thr Ile Ser Tyr Gly Glu Leu Trp Ala
 65                  70                  75                  80

Arg Val Gly Ala Ile Ala Ala Trp Gln Ala Asp Gly Leu Ala Pro
                 85                  90                  95

Gly Asp Phe Val Ala Thr Val Gly Phe Thr Ser Pro Asp Tyr Val Ala
                 100                 105                 110

Val Asp Leu Ala Ala Ala Arg Ser Gly Leu Val Ser Val Pro Leu Gln
             115                 120                 125

Ala Gly Ala Ser Leu Ala Gln Leu Val Gly Ile Leu Glu Glu Thr Glu
         130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                 165                 170                 175

Arg Gly Pro Asp Ala Ser Glu Ser Ala Ala Asp Glu Arg Arg Gly Ala
             180                 185                 190

Leu Ala Asp Ala Glu Glu Gln Leu Ala Arg Ala Gly Arg Ala Val Val

```
              195                 200                 205
Val Glu Thr Leu Ala Asp Leu Ala Ala Arg Gly Glu Ala Leu Pro Glu
210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                    245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
            275                 280                 285

Arg Ala Val Leu Ala Gly Ala Leu Ser Ala Gly Gly Thr Ala His Phe
        290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
            355                 360                 365

Pro Glu Met Arg Ala Phe Met Glu Val Leu Gly Phe Pro Leu Leu
370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
                420                 425                 430

Ile Arg Ser Thr Ser Leu Ile Ser Gly Tyr Tyr Lys Arg Pro Glu Ile
            435                 440                 445

Thr Ala Glu Val Phe Asp Ala Gln Gly Tyr Tyr Lys Thr Gly Asp Val
450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
                500                 505                 510

Gly Asn Ser Glu Arg Ser Phe Leu Leu Ala Val Val Val Pro Asn Ala
            515                 520                 525

Glu Val Leu Gly Ala Arg Asp Gln Glu Glu Ala Lys Pro Leu Ile Ala
530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
            580                 585                 590

Arg Tyr Gly Glu Ala Leu Glu Ala Arg Tyr Asp Glu Ile Ala His Gly
        595                 600                 605

Gln Ala Asp Glu Leu Arg Ala Leu Arg Asp Gly Ala Gly Gln Arg Pro
        610                 615                 620
```

```
Val Val Glu Thr Val Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
            645                 650                 655

Ser Leu Ser Ala Leu Ser Leu Ala Asn Leu Leu His Asp Val Phe Glu
        660                 665                 670

Val Glu Val Pro Val Arg Ile Ile Ile Gly Pro Thr Ala Ser Leu Ala
    675                 680                 685

Gly Ile Ala Lys His Ile Glu Ala Glu Arg Ala Gly Ala Ser Ala Pro
690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
            725                 730                 735

Lys Gly Leu Pro Ala Ala Asp Gln Val Arg Thr Val Leu Leu Thr Gly
        740                 745                 750

Ala Asn Gly Trp Leu Gly Arg Phe Leu Ala Leu Glu Gln Leu Glu Arg
    755                 760                 765

Leu Ala Arg Ser Gly Gln Asp Gly Gly Lys Leu Ile Cys Leu Val Arg
770                 775                 780

Gly Lys Asp Ala Ala Ala Ala Arg Arg Arg Ile Glu Glu Thr Leu Gly
785                 790                 795                 800

Thr Asp Pro Ala Leu Ala Ala Arg Phe Ala Glu Leu Ala Glu Gly Arg
            805                 810                 815

Leu Glu Val Val Pro Gly Asp Val Gly Glu Pro Lys Phe Gly Leu Asp
        820                 825                 830

Asp Ala Ala Trp Asp Arg Leu Ala Glu Glu Val Asp Val Ile Val His
    835                 840                 845

Pro Ala Ala Leu Val Asn His Val Leu Pro Tyr His Gln Leu Phe Gly
850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
            885                 890                 895

Val Glu Pro Ser Ser Phe Glu Glu Asp Gly Asp Ile Arg Ala Val Val
        900                 905                 910

Pro Glu Arg Pro Leu Gly Asp Gly Tyr Ala Asn Gly Tyr Gly Asn Ser
    915                 920                 925

Lys Trp Ala Gly Glu Val Leu Leu Arg Glu Ala His Glu Leu Val Gly
930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
            965                 970                 975

Ser Leu Leu Ala Thr Gly Ile Ala Pro Lys Ser Phe Tyr Gln Gln Gly
        980                 985                 990

Ala Ala Gly Glu Arg Gln Arg Ala His Tyr Asp Gly Ile Pro Val Asp
    995                 1000                1005

Phe Thr Ala Glu Ala Ile Thr Thr Leu Gly Ala Glu Pro Ser Trp Phe
    1010                1015                1020

Asp Gly Gly Ala Gly Phe Arg Ser Phe Asp Val Phe Asn Pro His His
1025                1030                1035                1040
```

```
Asp Gly Val Gly Leu Asp Glu Phe Val Asp Trp Leu Ile Glu Ala Gly
                    1045                1050                1055

His Pro Ile Ser Arg Ile Asp Asp His Lys Glu Trp Phe Ala Arg Phe
        1060                1065                1070

Glu Thr Ala Val Arg Gly Leu Pro Glu Ala Gln Arg Gln His Ser Leu
        1075                1080                1085

Leu Pro Leu Leu Arg Ala Tyr Ser Phe Pro His Pro Pro Val Asp Gly
        1090                1095                1100

Ser Val Tyr Pro Thr Gly Lys Phe Gln Gly Ala Val Lys Ala Ala Gln
1105                1110                1115                1120

Val Gly Ser Asp His Asp Val Pro His Leu Gly Lys Ala Leu Ile Val
                    1125                1130                1135

Lys Tyr Ala Asp Asp Leu Lys Ala Leu Gly Leu Leu
        1140                1145

<210> SEQ ID NO 5
<211> LENGTH: 1168
<212> TYPE: PRT
<213> ORGANISM: Mycobacterium smegmatis

<400> SEQUENCE: 5

Met Thr Ile Glu Thr Arg Glu Asp Arg Phe Asn Arg Arg Ile Asp His
1               5                   10                  15

Leu Phe Glu Thr Asp Pro Gln Phe Ala Ala Ala Arg Pro Asp Glu Ala
            20                  25                  30

Ile Ser Ala Ala Ala Ala Asp Pro Glu Leu Arg Leu Pro Ala Ala Val
        35                  40                  45

Lys Gln Ile Leu Ala Gly Tyr Ala Asp Arg Pro Ala Leu Gly Lys Arg
    50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125

Ile Ala Leu Leu Glu Leu Gly Ala Val Ser Val Pro Leu Gln Thr Ser
    130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
        195                 200                 205

Ala Gly Thr Gly Val Val Val Glu Thr Ile Thr Asp Ala Leu Asp Arg
    210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270
```

-continued

```
Ser Lys Ala Arg Trp Asp Glu Thr Leu Gly Val Met Pro Ser Ile Thr
    275                 280                 285

Leu Asn Phe Met Pro Met Ser His Val Met Gly Arg Gly Ile Leu Cys
290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
                325                 330                 335

Asn Phe Val Pro Arg Ile Trp Asp Met Leu Phe Gln Glu Tyr Gln Ser
                340                 345                 350

Arg Leu Asp Asn Arg Arg Ala Glu Gly Ser Glu Asp Arg Ala Glu Ala
                355                 360                 365

Ala Val Leu Glu Glu Val Arg Thr Gln Leu Leu Gly Gly Arg Phe Val
    370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
                405                 410                 415

Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
            435                 440                 445

Asp Arg Pro Tyr Pro Arg Gly Glu Leu Leu Val Lys Ser Glu Gln Met
    450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
                500                 505                 510

Gln Gly Glu Phe Val Thr Val Ser Lys Leu Glu Ala Val Phe Gly Asp
            515                 520                 525

Ser Pro Leu Val Arg Gln Ile Tyr Val Tyr Gly Asn Ser Ala Arg Ser
    530                 535                 540

Tyr Leu Leu Ala Val Val Pro Thr Glu Glu Ala Leu Ser Arg Trp
545                 550                 555                 560

Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
    595                 600                 605

Arg Lys Leu Ala Arg Pro Lys Leu Lys Ala His Tyr Gly Glu Arg Leu
610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
    675                 680                 685
```

```
Phe Ser Asn Leu Leu His Glu Ile Phe Asp Val Asp Val Pro Val Gly
            690                 695                 700
Val Ile Val Ser Pro Ala Thr Asp Leu Ala Gly Val Ala Ala Tyr Ile
705                 710                 715                 720
Glu Gly Glu Leu Arg Gly Ser Lys Arg Pro Thr Tyr Ala Ser Val His
                725                 730                 735
Gly Arg Asp Ala Thr Glu Val Arg Ala Arg Asp Leu Ala Leu Gly Lys
            740                 745                 750
Phe Ile Asp Ala Lys Thr Leu Ser Ala Ala Pro Gly Leu Pro Arg Ser
            755                 760                 765
Gly Thr Glu Ile Arg Thr Val Leu Leu Thr Gly Ala Thr Gly Phe Leu
770                 775                 780
Gly Arg Tyr Leu Ala Leu Glu Trp Leu Glu Arg Met Asp Leu Val Asp
785                 790                 795                 800
Gly Lys Val Ile Cys Leu Val Arg Ala Arg Ser Asp Glu Ala Arg
                805                 810                 815
Ala Arg Leu Asp Ala Thr Phe Asp Thr Gly Asp Ala Thr Leu Leu Glu
            820                 825                 830
His Tyr Arg Ala Leu Ala Ala Asp His Leu Glu Val Ile Ala Gly Asp
            835                 840                 845
Lys Gly Glu Ala Asp Leu Gly Leu Asp His Asp Thr Trp Gln Arg Leu
850                 855                 860
Ala Asp Thr Val Asp Leu Ile Val Asp Pro Ala Ala Leu Val Asn His
865                 870                 875                 880
Val Leu Pro Tyr Ser Gln Met Phe Gly Pro Asn Ala Leu Gly Thr Ala
                885                 890                 895
Glu Leu Ile Arg Ile Ala Leu Thr Thr Thr Ile Lys Pro Tyr Val Tyr
            900                 905                 910
Val Ser Thr Ile Gly Val Gly Gln Gly Ile Ser Pro Glu Ala Phe Val
            915                 920                 925
Glu Asp Ala Asp Ile Arg Glu Ile Ser Ala Thr Arg Arg Val Asp Asp
            930                 935                 940
Ser Tyr Ala Asn Gly Tyr Gly Asn Ser Lys Trp Ala Gly Glu Val Leu
945                 950                 955                 960
Leu Arg Glu Ala His Asp Trp Cys Gly Leu Pro Val Ser Val Phe Arg
                965                 970                 975
Cys Asp Met Ile Leu Ala Asp Thr Thr Tyr Ser Gly Gln Leu Asn Leu
            980                 985                 990
Pro Asp Met Phe Thr Arg Leu Met Leu Ser Leu Val Ala Thr Gly Ile
            995                 1000                1005
Ala Pro Gly Ser Phe Tyr Glu Leu Asp Ala Asp Gly Asn Arg Gln Arg
1010                1015                1020
Ala His Tyr Asp Gly Leu Pro Val Glu Phe Ile Ala Glu Ala Ile Ser
1025                1030                1035                1040
Thr Ile Gly Ser Gln Val Thr Asp Gly Phe Glu Thr Phe His Val Met
                1045                1050                1055
Asn Pro Tyr Asp Asp Gly Ile Gly Leu Asp Glu Tyr Val Asp Trp Leu
            1060                1065                1070
Ile Glu Ala Gly Tyr Pro Val His Arg Val Asp Asp Tyr Ala Thr Trp
            1075                1080                1085
Leu Ser Arg Phe Glu Thr Ala Leu Arg Ala Leu Pro Glu Arg Gln Arg
            1090                1095                1100
Gln Ala Ser Leu Leu Pro Leu Leu His Asn Tyr Gln Gln Pro Ser Pro
```

```
                1105                1110                1115                1120
Pro Val Cys Gly Ala Met Ala Pro Thr Asp Arg Phe Arg Ala Ala Val
                    1125                1130                1135

Gln Asp Ala Lys Ile Gly Pro Asp Lys Asp Ile Pro His Val Thr Ala
                    1140                1145                1150

Asp Val Ile Val Lys Tyr Ile Ser Asn Leu Gln Met Leu Gly Leu Leu
                    1155                1160                1165

<210> SEQ ID NO 6
<211> LENGTH: 1185
<212> TYPE: PRT
<213> ORGANISM: Mycobacterium massiliense

<400> SEQUENCE: 6

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
                20                  25                  30

Pro Ala Val Ala Glu Gln Val Leu Arg Pro Gly Leu His Leu Ser Glu
            35                  40                  45

Ala Ile Ala Ala Leu Met Thr Gly Tyr Ala Glu Arg Pro Ala Leu Gly
        50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
                100                 105                 110

Val Lys Ala Gly Asp Leu Val Ala Thr Leu Gly Phe Thr Ser Ile Asp
            115                 120                 125

Tyr Thr Val Leu Asp Leu Ala Ile Met Ile Leu Gly Gly Val Ala Val
        130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
                180                 185                 190

Phe Asp Tyr Thr Pro Glu Val Asp Asp Gln Arg Glu Ala Phe Glu Ala
            195                 200                 205

Ala Ser Thr Gln Leu Ala Gly Thr Gly Ile Ala Leu Glu Thr Leu Asp
        210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
                260                 265                 270

Arg Trp Trp Ile Arg Glu Asp Val Met Ala Gly Thr Glu Asn Leu Pro
            275                 280                 285

Met Ile Gly Leu Asn Phe Met Pro Met Ser His Ile Met Gly Arg Gly
        290                 295                 300

Thr Leu Thr Ser Thr Leu Ser Thr Gly Gly Thr Gly Tyr Phe Ala Ala
305                 310                 315                 320
```

-continued

```
Ser Ser Asp Met Ser Thr Leu Phe Glu Asp Met Glu Leu Ile Arg Pro
                325                 330                 335

Thr Ala Leu Ala Leu Val Pro Arg Val Cys Asp Met Val Phe Gln Arg
            340                 345                 350

Phe Gln Thr Glu Val Asp Arg Arg Leu Ala Ser Gly Asp Thr Ala Ser
        355                 360                 365

Ala Glu Ala Val Ala Ala Glu Val Lys Ala Asp Ile Arg Asp Asn Leu
    370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
            420                 425                 430

Val Gln Arg Pro Pro Val Ile Asp Tyr Lys Leu Val Asp Val Pro Glu
        435                 440                 445

Leu Gly Tyr Phe Ser Thr Asp Lys Pro His Pro Arg Gly Glu Leu Leu
    450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Asp Arg Arg Asn
            500                 505                 510

Asn Val Leu Lys Leu Ser Gln Gly Glu Phe Val Ala Val Ala Thr Leu
        515                 520                 525

Glu Ala Glu Tyr Ala Asn Ser Pro Val Val His Gln Ile Tyr Val Tyr
    530                 535                 540

Gly Ser Ser Glu Arg Ser Tyr Leu Leu Ala Val Val Pro Thr Pro
545                 550                 555                 560

Glu Ala Val Ala Ala Lys Gly Asp Ala Ala Leu Lys Thr Thr
                565                 570                 575

Ile Ala Asp Ser Leu Gln Asp Ile Ala Lys Glu Ile Gln Leu Gln Ser
            580                 585                 590

Tyr Glu Val Pro Arg Asp Phe Ile Ile Glu Pro Gln Pro Phe Thr Gln
        595                 600                 605

Gly Asn Gly Leu Leu Thr Gly Ile Ala Lys Leu Ala Arg Pro Asn Leu
    610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
            660                 665                 670

Val Ser Ser Ala Glu Leu Ala Ala Asp Ala His Phe Thr Asp Leu Gly
        675                 680                 685

Gly Asp Ser Leu Ser Ala Leu Ser Phe Ser Asp Leu Leu Arg Asp Ile
    690                 695                 700

Phe Ala Val Glu Val Pro Val Gly Val Ile Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
```

```
                740                 745                 750
Arg Ala Ala Asp Leu Thr Leu Asp Lys Phe Ile Asp Glu Ala Thr Leu
        755                 760                 765
His Ala Ala Pro Ser Leu Pro Lys Ala Ala Gly Ile Pro His Thr Val
        770                 775                 780
Leu Leu Thr Gly Ser Asn Gly Tyr Leu Gly His Tyr Leu Ala Leu Glu
785                 790                 795                 800
Trp Leu Glu Arg Leu Asp Lys Thr Asp Gly Lys Leu Ile Val Ile Val
                805                 810                 815
Arg Gly Lys Asn Ala Glu Ala Ala Tyr Gly Arg Leu Glu Glu Ala Phe
        820                 825                 830
Asp Thr Gly Asp Thr Glu Leu Leu Ala His Phe Arg Ser Leu Ala Asp
        835                 840                 845
Lys His Leu Glu Val Leu Ala Gly Asp Ile Gly Asp Pro Asn Leu Gly
        850                 855                 860
Leu Asp Ala Asp Thr Trp Gln Arg Leu Ala Asp Thr Val Asp Val Ile
865                 870                 875                 880
Val His Pro Ala Ala Leu Val Asn His Val Leu Pro Tyr Asn Gln Leu
                885                 890                 895
Phe Gly Pro Asn Val Val Gly Thr Ala Glu Ile Ile Lys Leu Ala Ile
        900                 905                 910
Thr Thr Lys Ile Lys Pro Val Thr Tyr Leu Ser Thr Val Ala Val Ala
        915                 920                 925
Ala Tyr Val Asp Pro Thr Thr Phe Asp Glu Glu Ser Asp Ile Arg Leu
        930                 935                 940
Ile Ser Ala Val Arg Pro Ile Asp Asp Gly Tyr Ala Asn Gly Tyr Gly
945                 950                 955                 960
Asn Ala Lys Trp Ala Gly Glu Val Leu Leu Arg Glu Ala His Asp Leu
                965                 970                 975
Cys Gly Leu Pro Val Ala Val Phe Arg Ser Asp Met Ile Leu Ala His
        980                 985                 990
Ser Arg Tyr Thr Gly Gln Leu Asn Val Pro Asp Gln Phe Thr Arg Leu
        995                 1000                1005
Ile Leu Ser Leu Ile Ala Thr Gly Ile Ala Pro Gly Ser Phe Tyr Gln
        1010                1015                1020
Ala Gln Thr Thr Gly Glu Arg Pro Leu Ala His Tyr Asp Gly Leu Pro
1025                1030                1035                1040
Gly Asp Phe Thr Ala Glu Ala Ile Thr Thr Leu Gly Thr Gln Val Pro
                1045                1050                1055
Glu Gly Ser Glu Gly Phe Val Thr Tyr Asp Cys Val Asn Pro His Ala
        1060                1065                1070
Asp Gly Ile Ser Leu Asp Asn Phe Val Asp Trp Leu Ile Glu Ala Gly
        1075                1080                1085
Tyr Pro Ile Ala Arg Ile Asp Asn Tyr Thr Glu Trp Phe Thr Arg Phe
        1090                1095                1100
Asp Thr Ala Ile Arg Gly Leu Ser Glu Lys Gln Lys Gln His Ser Leu
1105                1110                1115                1120
Leu Pro Leu Leu His Ala Phe Glu Gln Pro Ser Ala Ala Glu Asn His
                1125                1130                1135
Gly Val Val Pro Ala Lys Arg Phe Gln His Ala Val Gln Ala Ala Gly
        1140                1145                1150
Ile Gly Pro Val Gly Gln Asp Gly Thr Thr Asp Ile Pro His Leu Ser
        1155                1160                1165
```

-continued

Arg Arg Leu Ile Val Lys Tyr Ala Lys Asp Leu Glu Gln Leu Gly Leu
            1170                1175                1180

Leu
1185

<210> SEQ ID NO 7
<211> LENGTH: 1186
<212> TYPE: PRT
<213> ORGANISM: Segniliparus rotundus

<400> SEQUENCE: 7

Met Thr Gln Ser His Thr Gln Gly Pro Gln Ala Ser Ala Ala His Ser
 1                5                 10                 15

Arg Leu Ala Arg Arg Ala Ala Glu Leu Leu Ala Thr Asp Pro Gln Ala
             20                 25                 30

Ala Ala Thr Leu Pro Asp Pro Glu Val Val Arg Gln Ala Thr Arg Pro
         35                 40                 45

Gly Leu Arg Leu Ala Glu Arg Val Asp Ala Ile Leu Ser Gly Tyr Ala
     50                 55                 60

Asp Arg Pro Ala Leu Gly Gln Arg Ser Phe Gln Thr Val Lys Asp Pro
65                 70                 75                 80

Ile Thr Gly Arg Ser Ser Val Glu Leu Leu Pro Thr Phe Asp Thr Ile
                 85                 90                 95

Thr Tyr Arg Glu Leu Arg Glu Arg Ala Thr Ala Ile Ala Ser Asp Leu
            100                105                110

Ala His His Pro Gln Ala Pro Ala Lys Pro Gly Asp Phe Leu Ala Ser
         115                120                125

Ile Gly Phe Ile Ser Val Asp Tyr Val Ala Ile Asp Ile Ala Gly Val
    130                135                140

Phe Ala Gly Leu Thr Ala Val Pro Leu Gln Thr Gly Ala Thr Leu Ala
145                150                155                160

Thr Leu Thr Ala Ile Thr Ala Glu Thr Ala Pro Thr Leu Phe Ala Ala
                165                170                175

Ser Ile Glu His Leu Pro Thr Ala Val Asp Ala Val Leu Ala Thr Pro
            180                185                190

Ser Val Arg Arg Leu Leu Val Phe Asp Tyr Arg Ala Gly Ser Asp Glu
         195                200                205

Asp Arg Glu Ala Val Glu Ala Ala Lys Arg Lys Ile Ala Asp Ala Gly
    210                215                220

Ser Ser Val Leu Val Asp Val Leu Asp Glu Val Ile Ala Arg Gly Lys
225                230                235                240

Ser Ala Pro Lys Ala Pro Leu Pro Ala Thr Asp Ala Gly Asp Asp
                245                250                255

Ser Leu Ser Leu Leu Ile Tyr Thr Ser Gly Ser Thr Gly Thr Pro Lys
            260                265                270

Gly Ala Met Tyr Pro Glu Arg Asn Val Ala His Phe Trp Gly Gly Val
         275                280                285

Trp Ala Ala Ala Phe Asp Glu Asp Ala Ala Pro Pro Val Pro Ala Ile
    290                295                300

Asn Ile Thr Phe Leu Pro Leu Ser His Val Ala Ser Arg Leu Ser Leu
305                310                315                320

Met Pro Thr Leu Ala Arg Gly Gly Leu Met His Phe Val Ala Lys Ser
                325                330                335

Asp Leu Ser Thr Leu Phe Glu Asp Leu Lys Leu Ala Arg Pro Thr Asn

```
              340             345             350
Leu Phe Leu Val Pro Arg Val Glu Met Leu Tyr Gln His Tyr Gln
            355                 360             365
Ser Glu Leu Asp Arg Arg Gly Val Gln Asp Gly Thr Arg Glu Ala Glu
    370                 375             380
Ala Val Lys Asp Asp Leu Arg Thr Gly Leu Leu Gly Gly Arg Ile Leu
385                 390             395                 400
Thr Ala Gly Phe Gly Ser Ala Pro Leu Ser Ala Glu Leu Ala Gly Phe
                405             410             415
Ile Glu Ser Leu Leu Gln Ile His Leu Val Asp Gly Tyr Gly Ser Thr
            420             425             430
Glu Ala Gly Pro Val Trp Arg Asp Gly Tyr Leu Val Lys Pro Pro Val
        435             440             445
Thr Asp Tyr Lys Leu Ile Asp Val Pro Glu Leu Gly Tyr Phe Ser Thr
    450             455             460
Asp Ser Pro His Pro Arg Gly Glu Leu Ala Ile Lys Thr Gln Thr Ile
465             470             475             480
Leu Pro Gly Tyr Tyr Lys Arg Pro Glu Thr Thr Ala Glu Val Phe Asp
            485             490             495
Glu Asp Gly Phe Tyr Leu Thr Gly Asp Val Val Ala Gln Ile Gly Pro
            500             505             510
Glu Gln Phe Ala Tyr Val Asp Arg Arg Lys Asn Val Leu Lys Leu Ser
            515             520             525
Gln Gly Glu Phe Val Thr Leu Ala Lys Leu Glu Ala Ala Tyr Ser Ser
    530             535             540
Ser Pro Leu Val Arg Gln Leu Phe Val Tyr Gly Ser Ser Glu Arg Ser
545             550             555             560
Tyr Leu Leu Ala Val Ile Val Pro Thr Pro Asp Ala Leu Lys Lys Phe
                565             570             575
Gly Val Gly Glu Ala Ala Lys Ala Ala Leu Gly Glu Ser Leu Gln Lys
            580             585             590
Ile Ala Arg Asp Glu Gly Leu Gln Ser Tyr Glu Val Pro Arg Asp Phe
            595             600             605
Ile Ile Glu Thr Asp Pro Phe Thr Val Glu Asn Gly Leu Leu Ser Asp
    610             615             620
Ala Arg Lys Ser Leu Arg Pro Lys Leu Lys Glu His Tyr Gly Glu Arg
625             630             635             640
Leu Glu Ala Met Tyr Lys Glu Leu Ala Asp Gly Gln Ala Asn Glu Leu
                645             650             655
Arg Asp Ile Arg Arg Gly Val Gln Gln Arg Pro Thr Leu Glu Thr Val
            660             665             670
Arg Arg Ala Ala Ala Met Leu Gly Ala Ser Ala Ala Glu Ile Lys
            675             680             685
Pro Asp Ala His Phe Thr Asp Leu Gly Gly Asp Ser Leu Ser Ala Leu
    690             695             700
Thr Phe Ser Asn Phe Leu His Asp Leu Phe Glu Val Asp Val Pro Val
705             710             715             720
Gly Val Ile Val Ser Ala Ala Asn Thr Leu Gly Ser Val Ala Glu His
                725             730             735
Ile Asp Ala Gln Leu Ala Gly Gly Arg Ala Arg Pro Thr Phe Ala Thr
            740             745             750
Val His Gly Lys Gly Ser Thr Thr Ile Lys Ala Ser Asp Leu Thr Leu
            755             760             765
```

-continued

```
Asp Lys Phe Ile Asp Glu Gln Thr Leu Glu Ala Ala Lys His Leu Pro
770                 775                 780
Lys Pro Ala Asp Pro Pro Arg Thr Val Leu Leu Thr Gly Ala Asn Gly
785                 790                 795                 800
Trp Leu Gly Arg Phe Leu Ala Leu Glu Trp Leu Glu Arg Leu Ala Pro
                805                 810                 815
Ala Gly Gly Lys Leu Ile Thr Ile Val Arg Gly Lys Asp Ala Ala Gln
                820                 825                 830
Ala Lys Ala Arg Leu Asp Ala Ala Tyr Glu Ser Gly Asp Pro Lys Leu
            835                 840                 845
Ala Gly His Tyr Gln Asp Leu Ala Ala Thr Thr Leu Glu Val Leu Ala
            850                 855                 860
Gly Asp Phe Ser Glu Pro Arg Leu Gly Leu Asp Glu Ala Thr Trp Asn
865                 870                 875                 880
Arg Leu Ala Asp Glu Val Asp Phe Ile Ser His Pro Gly Ala Leu Val
                885                 890                 895
Asn His Val Leu Pro Tyr Asn Gln Leu Phe Gly Pro Asn Val Ala Gly
                900                 905                 910
Val Ala Glu Ile Ile Lys Leu Ala Ile Thr Thr Arg Ile Lys Pro Val
                915                 920                 925
Thr Tyr Leu Ser Thr Val Ala Val Ala Ala Gly Val Glu Pro Ser Ala
930                 935                 940
Leu Asp Glu Asp Gly Asp Ile Arg Thr Val Ser Ala Glu Arg Ser Val
945                 950                 955                 960
Asp Glu Gly Tyr Ala Asn Gly Tyr Gly Asn Ser Lys Trp Gly Gly Glu
                965                 970                 975
Val Leu Leu Arg Glu Ala His Asp Arg Thr Gly Leu Pro Val Arg Val
                980                 985                 990
Phe Arg Ser Asp Met Ile Leu Ala His Gln Lys Tyr Thr Gly Gln Val
                995                 1000                1005
Asn Ala Thr Asp Gln Phe Thr Arg Leu Val Gln Ser Leu Leu Ala Thr
            1010                1015                1020
Gly Leu Ala Pro Lys Ser Phe Tyr Glu Leu Asp Ala Gln Gly Asn Arg
1025                1030                1035                1040
Gln Arg Ala His Tyr Asp Gly Ile Pro Val Asp Phe Thr Ala Glu Ser
            1045                1050                1055
Ile Thr Thr Leu Gly Gly Asp Gly Leu Glu Gly Tyr Arg Ser Tyr Asn
            1060                1065                1070
Val Phe Asn Pro His Arg Asp Gly Val Gly Leu Asp Glu Phe Val Asp
                1075                1080                1085
Trp Leu Ile Glu Ala Gly His Pro Ile Thr Arg Ile Asp Asp Tyr Asp
            1090                1095                1100
Gln Trp Leu Ser Arg Phe Glu Thr Ser Leu Arg Gly Leu Pro Glu Ser
1105                1110                1115                1120
Lys Arg Gln Ala Ser Val Leu Pro Leu Leu His Ala Phe Ala Arg Pro
            1125                1130                1135
Gly Pro Ala Val Asp Gly Ser Pro Phe Arg Asn Thr Val Phe Arg Thr
            1140                1145                1150
Asp Val Gln Lys Ala Lys Ile Gly Ala Glu His Asp Ile Pro His Leu
            1155                1160                1165
Gly Lys Ala Leu Val Leu Lys Tyr Ala Asp Asp Ile Lys Gln Leu Gly
            1170                1175                1180
```

Leu Leu
1185

<210> SEQ ID NO 8
<211> LENGTH: 459
<212> TYPE: PRT
<213> ORGANISM: Chromobacterium violaceum

<400> SEQUENCE: 8

Met Gln Lys Gln Arg Thr Thr Ser Gln Trp Arg Glu Leu Asp Ala Ala
 1               5                  10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
 50                  55                  60

Gly Tyr Gly Arg Lys Asp Phe Ala Glu Ala Ala Arg Arg Gln Met Glu
 65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

```
His Val Asp Asp Val Arg Gly Val Gly Met Val Gln Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
    450                 455

<210> SEQ ID NO 9
<211> LENGTH: 468
<212> TYPE: PRT
<213> ORGANISM: Pseudomonas aeruginosa

<400> SEQUENCE: 9

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
                20                  25                  30

Asp His Arg Val Asn Gly Ser Leu Asn Ile Ala Ala Gly Asp Gly Ala
            35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
    115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
    195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
```

```
                    275                 280                 285
Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
                340                 345                 350

Glu Gly Leu Leu Ala His Ala Asp Glu Val Gly Arg Tyr Phe Glu Glu
            355                 360                 365

Arg Leu Gln Ser Leu Arg Asp Leu Pro Ile Val Gly Asp Val Arg Gly
        370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
450                 455                 460

Ala Gly His Arg
465

<210> SEQ ID NO 10
<211> LENGTH: 454
<212> TYPE: PRT
<213> ORGANISM: Pseudomonas syringae

<400> SEQUENCE: 10

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
            20                  25                  30

Gly Pro Arg Ile Ile Thr Arg Ala Glu Gly Val Tyr Leu Trp Asp Ser
        35                  40                  45

Glu Gly Asn Lys Ile Leu Asp Gly Met Ser Gly Leu Trp Cys Val Ala
    50                  55                  60

Ile Gly Tyr Gly Arg Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
                85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
        115                 120                 125

Leu Arg Met Val Arg His Tyr Trp Ala Leu Lys Gly Gln Pro Asn Lys
    130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175
```

```
Pro Ile Pro Gly Val His Ile Pro Gln Pro Tyr Trp Phe Gly Glu
            180                 185                 190
Gly Gly Asp Met Thr Pro Asp Glu Phe Gly Ile Trp Ala Ala Glu Gln
        195                 200                 205
Leu Glu Lys Lys Ile Leu Glu Leu Gly Val Glu Asn Val Gly Ala Phe
    210                 215                 220
Ile Ala Glu Pro Ile Gln Gly Ala Gly Gly Val Ile Val Pro Pro Asp
225                 230                 235                 240
Ser Tyr Trp Pro Lys Ile Lys Glu Ile Leu Ser Arg Tyr Asp Ile Leu
                245                 250                 255
Phe Ala Ala Asp Glu Val Ile Cys Gly Phe Gly Arg Thr Ser Glu Trp
            260                 265                 270
Phe Gly Ser Asp Phe Tyr Gly Leu Arg Pro Asp Met Met Thr Ile Ala
        275                 280                 285
Lys Gly Leu Thr Ser Gly Tyr Val Pro Met Gly Gly Leu Ile Val Arg
    290                 295                 300
Asp Glu Ile Val Ala Val Leu Asn Glu Gly Gly Asp Phe Asn His Gly
305                 310                 315                 320
Phe Thr Tyr Ser Gly His Pro Val Ala Ala Ala Val Ala Leu Glu Asn
                325                 330                 335
Ile Arg Ile Leu Arg Glu Glu Lys Ile Val Glu Arg Val Arg Ser Glu
            340                 345                 350
Thr Ala Pro Tyr Leu Gln Lys Arg Leu Arg Glu Leu Ser Asp His Pro
        355                 360                 365
Leu Val Gly Glu Val Arg Gly Val Gly Leu Leu Gly Ala Ile Glu Leu
    370                 375                 380
Val Lys Asp Lys Thr Thr Arg Glu Arg Tyr Thr Asp Lys Gly Ala Gly
385                 390                 395                 400
Met Ile Cys Arg Thr Phe Cys Phe Asp Asn Gly Leu Ile Met Arg Ala
                405                 410                 415
Val Gly Asp Thr Met Ile Ile Ala Pro Pro Leu Val Ile Ser Phe Ala
            420                 425                 430
Gln Ile Asp Glu Leu Val Glu Lys Ala Arg Thr Cys Leu Asp Leu Thr
        435                 440                 445
Leu Ala Val Leu Gln Gly
    450

<210> SEQ ID NO 11
<211> LENGTH: 467
<212> TYPE: PRT
<213> ORGANISM: Rhodobacter sphaeroides

<400> SEQUENCE: 11

Met Thr Arg Asn Asp Ala Thr Asn Ala Ala Gly Ala Val Gly Ala Ala
  1               5                  10                  15
Met Arg Asp His Ile Leu Leu Pro Ala Gln Glu Met Ala Lys Leu Gly
             20                  25                  30
Lys Ser Ala Gln Pro Val Leu Thr His Ala Glu Gly Ile Tyr Val His
         35                  40                  45
Thr Glu Asp Gly Arg Arg Leu Ile Asp Gly Pro Ala Gly Met Trp Cys
     50                  55                  60
Ala Gln Val Gly Tyr Gly Arg Arg Glu Ile Val Asp Ala Met Ala His
 65                  70                  75                  80
Gln Ala Met Val Leu Pro Tyr Ala Ser Pro Trp Tyr Met Ala Thr Ser
                 85                  90                  95
```

```
Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
                180                 185                 190

Ala Gly Asn Arg Ser Gln Glu Ala Phe Leu Asp Asp Leu Val Gln Glu
            195                 200                 205

Phe Glu Asp Arg Ile Glu Ser Leu Gly Pro Asp Thr Ile Ala Ala Phe
210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
                260                 265                 270

Phe Ala Ser Glu Lys Val Phe Gly Val Val Pro Asp Ile Ile Thr Phe
            275                 280                 285

Ala Lys Gly Val Thr Ser Gly Tyr Val Pro Leu Gly Gly Leu Ala Ile
        290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
                340                 345                 350

Gln Ala Arg Glu Met Ala Asp Tyr Phe Ala Ala Ala Leu Ala Ser Leu
            355                 360                 365

Arg Asp Leu Pro Gly Val Ala Glu Thr Arg Ser Val Gly Leu Val Gly
        370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
                420                 425                 430

Ile Ile Ser Arg Ala Gln Ile Asp Glu Met Val Ala Ile Met Arg Gln
            435                 440                 445

Ala Ile Thr Glu Val Ser Ala Ala His Gly Leu Thr Lys Glu Pro
        450                 455                 460

Ala Ala Val
465

<210> SEQ ID NO 12
<211> LENGTH: 459
<212> TYPE: PRT
<213> ORGANISM: Escherichia coli
```

<400> SEQUENCE: 12

```
Met Asn Arg Leu Pro Ser Ser Ala Ser Ala Leu Ala Cys Ser Ala His
  1               5                  10                  15

Ala Leu Asn Leu Ile Glu Lys Arg Thr Leu Asp His Glu Glu Met Lys
             20                  25                  30

Ala Leu Asn Arg Glu Val Ile Glu Tyr Phe Lys Glu His Val Asn Pro
         35                  40                  45

Gly Phe Leu Glu Tyr Arg Lys Ser Val Thr Ala Gly Gly Asp Tyr Gly
     50                  55                  60

Ala Val Glu Trp Gln Ala Gly Ser Leu Asn Thr Leu Val Asp Thr Gln
 65                  70                  75                  80

Gly Gln Glu Phe Ile Asp Cys Leu Gly Gly Phe Gly Ile Phe Asn Val
                 85                  90                  95

Gly His Arg Asn Pro Val Val Ser Ala Val Gln Asn Gln Leu Ala
             100                 105                 110

Lys Gln Pro Leu His Ser Gln Glu Leu Leu Asp Pro Leu Arg Ala Met
         115                 120                 125

Leu Ala Lys Thr Leu Ala Ala Leu Thr Pro Gly Lys Leu Lys Tyr Ser
130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415
```

-continued

```
Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455

<210> SEQ ID NO 13
<211> LENGTH: 453
<212> TYPE: PRT
<213> ORGANISM: Vibrio Fluvialis

<400> SEQUENCE: 13

Met Asn Lys Pro Gln Ser Trp Glu Ala Arg Ala Glu Thr Tyr Ser Leu
 1               5                  10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
```

```
                    325                 330                 335
Ile Asp Val Val Met Asn Glu Gly Leu Ala Glu Asn Val Arg Arg Leu
                340                 345                 350

Ala Pro Arg Phe Glu Arg Leu Lys His Ile Ala Glu Arg Pro Asn
            355                 360                 365

Ile Gly Glu Tyr Arg Gly Ile Gly Phe Met Trp Ala Leu Glu Ala Val
        370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
                420                 425                 430

Gln Met Asp Glu Met Phe Asp Lys Leu Glu Lys Ala Leu Asp Lys Val
            435                 440                 445

Phe Ala Glu Val Ala
        450

<210> SEQ ID NO 14
<211> LENGTH: 224
<212> TYPE: PRT
<213> ORGANISM: Bacillus subtilis

<400> SEQUENCE: 14

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220

<210> SEQ ID NO 15
<211> LENGTH: 222
```

```
<212> TYPE: PRT
<213> ORGANISM: Nocardia sp. NRRL 5646

<400> SEQUENCE: 15

Met Ile Glu Thr Ile Leu Pro Ala Gly Val Glu Ser Ala Glu Leu Leu
 1               5                  10                  15

Glu Tyr Pro Glu Asp Leu Lys Ala His Pro Ala Glu Glu His Leu Ile
            20                  25                  30

Ala Lys Ser Val Glu Lys Arg Arg Asp Phe Ile Gly Ala Arg His
        35                  40                  45

Cys Ala Arg Leu Ala Leu Ala Glu Leu Gly Glu Pro Pro Val Ala Ile
    50                  55                  60

Gly Lys Gly Glu Arg Gly Ala Pro Ile Trp Pro Arg Gly Val Val Gly
 65                  70                  75                  80

Ser Leu Thr His Cys Asp Gly Tyr Arg Ala Ala Val Ala His Lys
                85                  90                  95

Met Arg Phe Arg Ser Ile Gly Ile Asp Ala Glu Pro His Ala Thr Leu
                100                 105                 110

Pro Glu Gly Val Leu Asp Ser Val Ser Leu Pro Pro Glu Arg Glu Trp
            115                 120                 125

Leu Lys Thr Thr Asp Ser Ala Leu His Leu Asp Arg Leu Leu Phe Cys
    130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220

<210> SEQ ID NO 16
<211> LENGTH: 1819
<212> TYPE: PRT
<213> ORGANISM: Azotobacter vinelandii

<400> SEQUENCE: 16

Met Gln Asp Ser Val Met Gln Arg Met Trp Asn Ser Ala His Leu Ser
 1               5                  10                  15

Gly Gly Asn Ala Ala Tyr Val Glu Glu Leu Tyr Glu Leu Tyr Leu His
            20                  25                  30

Asp Pro Asn Ala Val Pro Glu Glu Trp Arg Thr Tyr Phe Glu Lys Leu
        35                  40                  45

Pro Ala Glu Ala Gly Thr Ser Thr Asp Val Pro His Ala Pro Val Arg
    50                  55                  60

Asp Gln Phe Val Leu Leu Ala Lys Asn Gln Arg Ala Gln Pro Val
 65                  70                  75                  80

Ala Thr Ser Ser Val Ser Thr Glu His Glu Lys Lys Gln Val Glu Val
                85                  90                  95

Leu Arg Leu Ile Gln Ala Tyr Arg Thr Arg Gly His Gln Ala Ser Gln
                100                 105                 110

Leu Asp Pro Leu Gly Leu Trp Gln Arg Thr Ala Pro Ser Asp Leu Ser
            115                 120                 125
```

```
Ile Thr His Tyr Gly Leu Thr Asn Ala Asp Leu Asp Thr Pro Phe Arg
130                 135                 140

Thr Gly Glu Leu Tyr Ile Gly Lys Glu Ala Thr Leu Arg Glu Ile
145                 150                 155                 160

Leu Gln Ala Leu Gln Glu Thr Tyr Cys Arg Thr Ile Gly Ala Glu Phe
                165                 170                 175

Thr His Ile Val Asp Ser Glu Gln Arg Asn Trp Phe Ala Gln Arg Leu
                180                 185                 190

Glu Ser Val Arg Gly Arg Pro Val Tyr Ser Lys Glu Ala Lys Ser His
                195                 200                 205

Leu Leu Glu Arg Leu Ser Ala Ala Glu Gly Leu Glu Lys Tyr Leu Gly
210                 215                 220

Thr Lys Tyr Pro Gly Thr Lys Arg Phe Gly Leu Glu Gly Gly Glu Ser
225                 230                 235                 240

Leu Val Pro Val Val Asp Glu Ile Ile Gln Arg Ser Gly Ser Tyr Gly
                245                 250                 255

Thr Lys Glu Val Val Ile Gly Met Ala His Arg Gly Arg Leu Asn Leu
                260                 265                 270

Leu Val Asn Ala Leu Gly Lys Asn Pro Arg Asp Leu Phe Asp Glu Phe
            275                 280                 285

Glu Gly Lys His Leu Val Glu Leu Gly Ser Gly Asp Val Lys Tyr His
290                 295                 300

Gln Gly Phe Ser Ser Asn Val Met Thr Ser Gly Gly Glu Val His Leu
305                 310                 315                 320

Ala Met Ala Phe Asn Pro Ser His Leu Glu Ile Val Ser Pro Val Val
                325                 330                 335

Glu Gly Ser Val Arg Ala Arg Gln Asp Arg Arg Val Asp Ala Thr Gly
                340                 345                 350

Glu Lys Val Val Pro Ile Ser Ile His Gly Asp Ser Ala Phe Ala Gly
            355                 360                 365

Gln Gly Val Val Met Glu Thr Phe Gln Met Ser Gln Ile Arg Gly Tyr
            370                 375                 380

Lys Thr Gly Gly Thr Ile His Ile Val Val Asn Asn Gln Val Gly Phe
385                 390                 395                 400

Thr Thr Ser Asn Pro Val Asp Thr Arg Ser Thr Glu Tyr Cys Thr Asp
                405                 410                 415

Pro Ala Lys Met Ile Gln Ala Pro Val Leu His Val Asn Gly Asp Asp
                420                 425                 430

Pro Glu Ala Val Leu Phe Val Thr Gln Leu Ala Val Asp Tyr Arg Met
            435                 440                 445

Gln Phe Lys Arg Asp Val Val Ile Asp Leu Val Cys Tyr Arg Arg Arg
450                 455                 460

Gly His Asn Glu Ala Asp Glu Pro Ser Gly Thr Gln Pro Leu Met Tyr
465                 470                 475                 480

Gln Lys Ile Ala Lys Gln Pro Thr Thr Arg Glu Leu Tyr Ala Asp Ala
                485                 490                 495

Leu Val Lys Glu Gly Ser Leu Ser Gln Glu Val Gln Ala Lys Val
            500                 505                 510

Asp Glu Tyr Arg Thr Ala Leu Asp Asn Gly Gln His Val Leu Lys Ser
            515                 520                 525

Leu Val Lys Glu Pro Asn Thr Glu Leu Phe Val Asp Trp Thr Pro Tyr
530                 535                 540

Leu Gly His Ala Trp Thr Ala Arg His Asp Thr Ser Phe Glu Leu Lys
```

```
               545                 550                 555                 560
Thr Leu Gln Glu Leu Asn Ala Lys Leu Leu Gln Ile Pro Glu Gly Phe
                565                 570                 575

Val Val Gln Arg Gln Val Ala Lys Ile Leu Glu Asp Arg Gly Arg Met
                580                 585                 590

Gly Val Gly Ala Met Pro Ile Asn Trp Gly Cys Ala Glu Thr Leu Ala
                595                 600                 605

Tyr Ala Thr Leu Leu Lys Glu Gly His Pro Val Arg Ile Thr Gly Gln
610                 615                 620

Asp Val Gly Arg Gly Thr Phe Ser His Arg His Ala Ala Leu His Asn
625                 630                 635                 640

Gln Lys Asp Ala Ser Arg Tyr Ile Pro Leu Gln Asn Leu Tyr Glu Gly
                645                 650                 655

Gln Pro Lys Phe Glu Leu Tyr Asp Ser Phe Leu Ser Glu Glu Ala Val
                660                 665                 670

Leu Ala Phe Glu Tyr Gly Tyr Ala Thr Thr Thr Pro Asn Ala Leu Val
                675                 680                 685

Ile Trp Glu Ala Ser Ser Gly Asp Phe Ala Asn Gly Ala Gln Val Val
                690                 695                 700

Ile Asp Gln Phe Ile Ser Ser Gly Glu Thr Lys Trp Gly Ala Leu Cys
705                 710                 715                 720

Gly Leu Thr Met Leu Leu Pro His Gly Tyr Glu Gly Gln Gly Pro Glu
                725                 730                 735

His Ser Ser Ala Arg Leu Glu Arg Tyr Leu Gln Leu Cys Ala Glu Gln
                740                 745                 750

Asn Ile Gln Val Cys Val Pro Thr Thr Pro Ala Gln Val Tyr His Met
                755                 760                 765

Leu Arg Arg Gln Val Ile Arg Pro Leu Arg Lys Pro Leu Val Ala Leu
                770                 775                 780

Thr Pro Lys Ser Leu Leu Arg His Lys Ser Ala Ile Ser Thr Leu Glu
785                 790                 795                 800

Asp Leu Ala Leu Gly Ser Phe His Pro Val Leu Pro Glu Val Asp Ser
                805                 810                 815

Leu Asp Pro Lys Lys Val Glu Arg Leu Val Leu Cys Ser Gly Lys Val
                820                 825                 830

Tyr Tyr Asp Leu Leu Asp Lys Arg His Ala Glu Gly Arg Glu Asp Ile
                835                 840                 845

Ala Ile Val Arg Ile Glu Gln Leu Tyr Pro Phe Pro Glu Gly Glu Leu
850                 855                 860

Ala Glu Val Met Ala Pro Tyr Thr Asn Leu Lys His Val Val Trp Cys
865                 870                 875                 880

Gln Glu Glu Pro Met Asn Gln Gly Ala Trp Tyr Cys Ser Gln His His
                885                 890                 895

Met Arg Arg Val Ala Ser Ala His Lys Lys Glu Leu Phe Leu Gln Tyr
                900                 905                 910

Ala Gly Arg Glu Ala Ser Ala Ala Pro Ala Cys Gly Tyr Ala Ser Met
                915                 920                 925

His Ala Glu Gln Gln Glu Lys Leu Leu Gln Asp Ala Phe Thr Val Met
                930                 935                 940

Ala Ile Asp Ile Lys Ala Pro Thr Phe Pro Glu Ser Ile Ala Asp Gly
945                 950                 955                 960

Thr Val Ala Thr Trp His Lys Lys Pro Gly Glu Pro Val Lys Arg Asp
                965                 970                 975
```

```
Glu Leu Ile Val Asp Ile Glu Thr Asp Lys Val Val Met Glu Val Leu
                980                 985                 990

Ala Glu Ala Asp Gly Val Ile Ala Glu Ile Val Lys Asn Glu Gly Asp
            995                 1000                1005

Thr Val Leu Ser Gly Glu Leu Leu Gly Lys Leu Thr Glu Gly Gly Ala
        1010                1015                1020

Ala Thr Ala Ala Pro Ala Ala Ala Pro Ala Pro Ala Ala Ala Pro
1025                1030                1035                1040

Ala Ala Ala Glu Ala Pro Ile Leu Ser Pro Ala Ala Arg Lys Ile Ala
                1045                1050                1055

Glu Glu Asn Ala Ile Ala Ala Asp Ser Ile Thr Gly Thr Gly Lys Gly
                1060                1065                1070

Gly Arg Val Thr Lys Glu Asp Ala Val Ala Ala Glu Ala Lys Lys
            1075                1080                1085

Ser Ala Pro Ala Gly Gln Pro Ala Pro Ala Ala Thr Ala Ala Pro Leu
            1090                1095                1100

Phe Ala Ala Gly Asp Arg Val Glu Lys Arg Val Pro Met Thr Arg Leu
1105                1110                1115                1120

Arg Ala Lys Val Ala Glu Arg Leu Val Glu Ala Gln Ser Ser Met Ala
                1125                1130                1135

Met Leu Thr Thr Phe Asn Glu Val Asn Met Lys Pro Val Met Glu Leu
                1140                1145                1150

Arg Ala Lys Tyr Lys Asp Leu Phe Glu Lys Thr His Asn Gly Val Arg
                1155                1160                1165

Leu Gly Phe Met Ser Phe Phe Val Lys Ala Ala Val Glu Ala Leu Lys
            1170                1175                1180

Arg Gln Pro Gly Val Asn Ala Ser Ile Asp Gly Asn Asp Ile Val Tyr
1185                1190                1195                1200

His Gly Tyr Gln Asp Ile Gly Val Ala Val Ser Ser Asp Arg Gly Leu
                1205                1210                1215

Val Val Pro Val Leu Arg Asn Ala Glu Phe Met Ser Leu Ala Glu Ile
            1220                1225                1230

Glu Gly Gly Ile Asn Glu Phe Gly Lys Lys Ala Lys Ala Gly Lys Leu
            1235                1240                1245

Thr Ile Glu Glu Met Thr Gly Gly Thr Phe Thr Ile Ser Asn Gly Gly
        1250                1255                1260

Val Phe Gly Ser Leu Leu Ser Thr Pro Ile Val Asn Pro Pro Gln Thr
1265                1270                1275                1280

Ala Ile Leu Gly Met His Lys Ile Gln Glu Arg Pro Met Ala Val Asn
                1285                1290                1295

Gly Gln Val Val Ile Leu Pro Met Met Tyr Leu Ala Leu Ser Tyr Asp
            1300                1305                1310

His Arg Leu Ile Asp Gly Lys Glu Ala Val Thr Phe Leu Val Thr Met
            1315                1320                1325

Lys Asp Leu Leu Glu Asp Pro Ala Arg Leu Leu Asp Val Met Ser
            1330                1335                1340

Gln Lys Phe Asp Val Ile Val Ile Gly Ala Gly Pro Gly Gly Tyr Val
1345                1350                1355                1360

Ala Ala Ile Lys Ser Ala Gln Leu Gly Leu Lys Thr Ala Leu Ile Glu
                1365                1370                1375

Lys Tyr Lys Gly Lys Glu Gly Lys Thr Ala Leu Gly Gly Thr Cys Leu
            1380                1385                1390
```

```
Asn Val Gly Cys Ile Pro Ser Lys Ala Leu Leu Asp Ser Ser Tyr Lys
            1395                1400                1405

Phe His Glu Ala His Glu Ser Phe Lys Leu His Gly Ile Ser Thr Gly
    1410                1415                1420

Glu Val Ala Ile Asp Val Pro Thr Met Ile Ala Arg Lys Asp Gln Ile
1425                1430                1435                1440

Val Arg Asn Leu Thr Gly Gly Val Ala Ser Leu Ile Lys Ala Asn Gly
                1445                1450                1455

Val Thr Leu Phe Glu Gly His Gly Lys Leu Leu Ala Gly Lys Lys Val
            1460                1465                1470

Glu Val Thr Ala Ala Asp Gly Ser Ser Gln Val Leu Asp Thr Glu Asn
        1475                1480                1485

Val Ile Leu Ala Ser Gly Ser Lys Pro Val Glu Ile Pro Pro Ala Pro
    1490                1495                1500

Val Asp Gln Asp Val Ile Val Asp Ser Thr Gly Ala Leu Asp Phe Gln
1505                1510                1515                1520

Asn Val Pro Gly Lys Leu Gly Val Ile Gly Ala Gly Val Ile Gly Leu
                1525                1530                1535

Glu Leu Gly Ser Val Trp Ala Arg Leu Gly Ala Glu Val Thr Val Leu
            1540                1545                1550

Glu Ala Met Asp Lys Phe Leu Pro Ala Val Asp Glu Gln Val Ala Lys
        1555                1560                1565

Glu Ala Gln Lys Ile Leu Thr Lys Gln Gly Leu Lys Ile Leu Leu Gly
    1570                1575                1580

Ala Arg Val Thr Gly Thr Glu Val Lys Asn Lys Gln Val Thr Val Lys
1585                1590                1595                1600

Phe Val Asp Ala Glu Gly Glu Lys Ser Gln Ala Phe Asp Lys Leu Ile
                1605                1610                1615

Val Ala Val Gly Arg Arg Pro Val Thr Thr Asp Leu Leu Ala Ala Asp
            1620                1625                1630

Ser Gly Val Thr Leu Asp Glu Arg Gly Phe Ile Tyr Val Asp Asp Tyr
        1635                1640                1645

Cys Ala Thr Ser Val Pro Gly Val Tyr Ala Ile Gly Asp Val Val Arg
    1650                1655                1660

Gly Ala Met Leu Ala His Lys Ala Ser Glu Glu Gly Val Val Val Ala
1665                1670                1675                1680

Glu Arg Ile Ala Gly His Lys Ala Gln Met Asn Tyr Asp Leu Ile Pro
                1685                1690                1695

Ala Val Ile Tyr Thr His Pro Glu Ile Ala Gly Val Gly Lys Thr Glu
            1700                1705                1710

Gln Ala Leu Lys Ala Glu Gly Val Ala Ile Asn Val Gly Val Phe Pro
        1715                1720                1725

Phe Ala Ala Ser Gly Arg Ala Met Ala Ala Asn Asp Thr Ala Gly Phe
    1730                1735                1740

Val Lys Val Ile Ala Asp Ala Lys Thr Asp Arg Val Leu Gly Val His
1745                1750                1755                1760

Val Ile Gly Pro Ser Ala Ala Glu Leu Val Gln Gln Gly Ala Ile Ala
                1765                1770                1775

Met Glu Phe Gly Thr Ser Ala Glu Asp Leu Gly Met Met Val Phe Ala
            1780                1785                1790

His Pro Ala Leu Ser Glu Ala Leu His Glu Ala Leu Ala Val Ser
        1795                1800                1805

Gly His Ala Ile His Val Ala Asn Arg Lys Lys
```

```
                         1810                1815
```

<210> SEQ ID NO 17
<211> LENGTH: 246
<212> TYPE: PRT
<213> ORGANISM: Lactobacillus brevis

<400> SEQUENCE: 17

```
Met Ala Ala Asn Glu Phe Ser Glu Thr His Arg Val Val Tyr Tyr Glu
  1               5                  10                  15

Ala Asp Asp Thr Gly Gln Leu Thr Leu Ala Met Leu Ile Asn Leu Phe
             20                  25                  30

Val Leu Val Ser Glu Asp Gln Asn Asp Ala Leu Gly Leu Ser Thr Ala
         35                  40                  45

Phe Val Gln Ser His Gly Val Gly Trp Val Val Thr Gln Tyr His Leu
     50                  55                  60

His Ile Asp Glu Leu Pro Arg Thr Gly Ala Gln Val Thr Ile Lys Thr
 65                  70                  75                  80

Arg Ala Thr Ala Tyr Asn Arg Tyr Phe Ala Tyr Arg Glu Tyr Trp Leu
                 85                  90                  95

Leu Asp Asp Ala Gly Gln Val Leu Ala Tyr Gly Glu Gly Ile Trp Val
            100                 105                 110

Thr Met Ser Tyr Ala Thr Arg Lys Ile Thr Thr Ile Pro Ala Glu Val
        115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160

Thr Val Arg Tyr Phe Asp Ile Asp Gly Asn Gly His Val Asn Asn Ala
                165                 170                 175

His Tyr Phe Asp Trp Met Leu Asp Val Leu Pro Ala Thr Phe Leu Arg
            180                 185                 190

Ala His His Pro Thr Asp Val Lys Ile Arg Phe Glu Asn Glu Val Gln
        195                 200                 205

Tyr Gly His Gln Val Thr Ser Glu Leu Ser Gln Ala Ala Ala Leu Thr
    210                 215                 220

Thr Gln His Met Ile Lys Val Gly Asp Leu Thr Ala Val Lys Ala Thr
225                 230                 235                 240

Ile Gln Trp Asp Asn Arg
                245
```

<210> SEQ ID NO 18
<211> LENGTH: 261
<212> TYPE: PRT
<213> ORGANISM: Lactobacillus plantarum

<400> SEQUENCE: 18

```
Met Ala Thr Leu Gly Ala Asn Ala Ser Leu Tyr Ser Glu Gln His Arg
  1               5                  10                  15

Ile Thr Tyr Tyr Glu Cys Asp Arg Thr Gly Arg Ala Thr Leu Thr Thr
             20                  25                  30

Leu Ile Asp Ile Ala Val Leu Ala Ser Glu Asp Gln Ser Asp Ala Leu
         35                  40                  45

Gly Leu Thr Thr Glu Met Val Gln Ser His Gly Val Gly Trp Val Val
     50                  55                  60

Thr Gln Tyr Ala Ile Asp Ile Thr Arg Met Pro Arg Gln Asp Glu Val
```

```
              65                  70                  75                  80
Val Thr Ile Ala Val Arg Gly Ser Ala Tyr Asn Pro Tyr Phe Ala Tyr
                     85                  90                  95

Arg Glu Phe Trp Ile Arg Asp Ala Asp Gly Gln Gln Leu Ala Tyr Ile
                100                 105                 110

Thr Ser Ile Trp Val Met Met Ser Gln Thr Thr Arg Arg Ile Val Lys
                115                 120                 125

Ile Leu Pro Glu Leu Val Ala Pro Tyr Gln Ser Glu Val Val Lys Arg
130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
                180                 185                 190

Ala Thr Phe Leu Leu Gln His Asp Leu Val His Val Asp Val Arg Tyr
                195                 200                 205

Glu Asn Glu Val Lys Tyr Gly Gln Thr Val Thr Ala His Ala Asn Ile
210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
                260

<210> SEQ ID NO 19
<211> LENGTH: 466
<212> TYPE: PRT
<213> ORGANISM: Escherichia coli

<400> SEQUENCE: 19

Met Asp Gln Lys Leu Leu Thr Asp Phe Arg Ser Glu Leu Leu Asp Ser
1                5                  10                  15

Arg Phe Gly Ala Lys Ala Ile Ser Thr Ile Ala Glu Ser Lys Arg Phe
                20                  25                  30

Pro Leu His Glu Met Arg Asp Asp Val Ala Phe Gln Ile Ile Asn Asp
            35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
                100                 105                 110

Pro Lys Asn Gly Gln Ala Val Gly Thr Asn Thr Ile Gly Ser Ser Glu
            115                 120                 125

Ala Cys Met Leu Gly Gly Met Ala Met Lys Trp Arg Trp Arg Lys Arg
130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175
```

Leu Arg Glu Ile Pro Met Arg Pro Gly Gln Leu Phe Met Asp Pro Lys
                180                 185                 190

Arg Met Ile Glu Ala Cys Asp Glu Asn Thr Ile Gly Val Val Pro Thr
            195                 200                 205

Phe Gly Val Thr Tyr Thr Gly Asn Tyr Glu Phe Pro Gln Pro Leu His
        210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465

<210> SEQ ID NO 20
<211> LENGTH: 715
<212> TYPE: PRT
<213> ORGANISM: Escherichia coli

<400> SEQUENCE: 20

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

```
Ala Phe Ala Asn Thr Tyr Ser Thr Leu Asp Val Ser Leu Asn Asp Leu
                 85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
            115                 120                 125

Leu Pro Pro Leu Thr Lys Ala Leu Phe Lys Tyr Val Arg Glu Gly Lys
        130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495
```

```
Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
        610                 615                 620

Gln Lys Glu Leu His Gly Met Thr Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
        690                 695                 700

Thr Val Lys Val Leu Lys Glu Glu Ser Lys Lys
705                 710                 715

<210> SEQ ID NO 21
<211> LENGTH: 732
<212> TYPE: PRT
<213> ORGANISM: Escherichia coli

<400> SEQUENCE: 21

Met Ser Lys Leu Lys Ile Ala Val Ser Asp Ser Cys Pro Asp Cys Phe
1               5                   10                  15

Thr Thr Gln Arg Glu Cys Ile Tyr Ile Asn Glu Ser Arg Asn Ile Asp
            20                  25                  30

Val Ala Ala Ile Val Leu Ser Leu Asn Asp Val Thr Cys Gly Lys Leu
        35                  40                  45

Asp Glu Ile Asp Ala Thr Gly Tyr Gly Ile Pro Val Phe Ile Ala Thr
    50                  55                  60

Glu Asn Gln Glu Arg Val Pro Ala Glu Tyr Leu Pro Arg Ile Ser Gly
65                  70                  75                  80

Val Phe Glu Asn Cys Glu Ser Arg Arg Glu Phe Tyr Gly Arg Gln Leu
                85                  90                  95

Glu Thr Ala Ala Ser His Tyr Glu Thr Gln Leu Arg Pro Pro Phe Phe
            100                 105                 110

Arg Ala Leu Val Asp Tyr Val Asn Gln Gly Asn Ser Ala Phe Asp Cys
        115                 120                 125

Pro Gly His Gln Gly Gly Glu Phe Phe Arg Arg His Pro Ala Gly Asn
    130                 135                 140

Gln Phe Val Glu Tyr Phe Gly Glu Ala Leu Phe Arg Ala Asp Leu Cys
145                 150                 155                 160
```

```
Asn Ala Asp Val Ala Met Gly Asp Leu Leu Ile His Glu Gly Ala Pro
                165                 170                 175
Cys Ile Ala Gln Gln His Ala Ala Lys Val Phe Asn Ala Asp Lys Thr
            180                 185                 190
Tyr Phe Val Leu Asn Gly Thr Ser Ser Asn Lys Val Val Leu Asn
        195                 200                 205
Ala Leu Leu Thr Pro Gly Asp Leu Val Leu Phe Asp Arg Asn Asn His
    210                 215                 220
Lys Ser Asn His His Gly Ala Leu Leu Gln Ala Gly Ala Thr Pro Val
225                 230                 235                 240
Tyr Leu Glu Thr Ala Arg Asn Pro Tyr Gly Phe Ile Gly Gly Ile Asp
                245                 250                 255
Ala His Cys Phe Glu Glu Ser Tyr Leu Arg Glu Leu Ile Ala Glu Val
            260                 265                 270
Ala Pro Gln Arg Ala Lys Glu Ala Arg Pro Phe Arg Leu Ala Val Ile
        275                 280                 285
Gln Leu Gly Thr Tyr Asp Gly Thr Ile Tyr Asn Ala Arg Gln Val Val
    290                 295                 300
Asp Lys Ile Gly His Leu Cys Asp Tyr Ile Leu Phe Asp Ser Ala Trp
305                 310                 315                 320
Val Gly Tyr Glu Gln Phe Ile Pro Met Met Ala Asp Cys Ser Pro Leu
                325                 330                 335
Leu Leu Asp Leu Asn Glu Asn Asp Pro Gly Ile Leu Val Thr Gln Ser
            340                 345                 350
Val His Lys Gln Gln Ala Gly Phe Ser Gln Thr Ser Gln Ile His Lys
        355                 360                 365
Lys Asp Ser His Ile Lys Gly Gln Gln Arg Tyr Val Pro His Lys Arg
    370                 375                 380
Met Asn Asn Ala Phe Met Met His Ala Ser Thr Ser Pro Phe Tyr Pro
385                 390                 395                 400
Leu Phe Ala Ala Leu Asn Ile Asn Ala Lys Met His Glu Gly Val Ser
                405                 410                 415
Gly Arg Asn Met Trp Met Asp Cys Val Val Asn Gly Ile Asn Ala Arg
            420                 425                 430
Lys Leu Ile Leu Asp Asn Cys Gln His Ile Arg Pro Phe Val Pro Glu
        435                 440                 445
Leu Val Asp Gly Lys Pro Trp Gln Ser Tyr Glu Thr Ala Gln Ile Ala
    450                 455                 460
Val Asp Leu Arg Phe Phe Gln Phe Val Pro Gly Glu His Trp His Ser
465                 470                 475                 480
Phe Glu Gly Tyr Ala Glu Asn Gln Tyr Phe Val Asp Pro Cys Lys Leu
                485                 490                 495
Leu Leu Thr Thr Pro Gly Ile Asp Ala Arg Asn Gly Glu Tyr Glu Ala
            500                 505                 510
Phe Gly Val Pro Ala Thr Ile Leu Ala Asn Phe Leu Arg Glu Asn Gly
        515                 520                 525
Val Val Pro Glu Lys Cys Asp Leu Asn Ser Ile Leu Phe Leu Leu Thr
    530                 535                 540
Pro Ala Glu Asp Met Ala Lys Leu Gln Gln Leu Val Ala Leu Leu Val
545                 550                 555                 560
Arg Phe Glu Lys Leu Leu Glu Ser Asp Ala Pro Leu Ala Glu Val Leu
                565                 570                 575
```

-continued

Pro Ser Ile Tyr Lys Gln His Glu Glu Arg Tyr Ala Gly Tyr Thr Leu
            580                 585                 590

Arg Gln Leu Cys Gln Glu Met His Asp Leu Tyr Ala Arg His Asn Val
        595                 600                 605

Lys Gln Leu Gln Lys Glu Met Phe Arg Lys Glu His Phe Pro Arg Val
    610                 615                 620

Ser Met Asn Pro Gln Glu Ala Asn Tyr Ala Tyr Leu Arg Gly Glu Val
625                 630                 635                 640

Glu Leu Val Arg Leu Pro Asp Ala Glu Gly Arg Ile Ala Ala Glu Gly
                645                 650                 655

Ala Leu Pro Tyr Pro Pro Gly Val Leu Cys Val Val Pro Gly Glu Ile
            660                 665                 670

Trp Gly Gly Ala Val Leu Arg Tyr Phe Ser Ala Leu Glu Glu Gly Ile
        675                 680                 685

Asn Leu Leu Pro Gly Phe Ala Pro Glu Leu Gln Gly Val Tyr Ile Glu
    690                 695                 700

Glu His Asp Gly Arg Lys Gln Val Trp Cys Tyr Val Ile Lys Pro Arg
705                 710                 715                 720

Asp Ala Gln Ser Thr Leu Leu Lys Gly Glu Lys Leu
                725                 730

<210> SEQ ID NO 22
<211> LENGTH: 713
<212> TYPE: PRT
<213> ORGANISM: Escherichia coli

<400> SEQUENCE: 22

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

```
Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
            245                 250                 255

Val Val Pro Val Trp Leu Lys Pro Thr Arg Asn Ala Leu Gly Ile Leu
        260                 265                 270

Gly Gly Ile Pro Arg Arg Glu Phe Thr Arg Asp Ser Ile Glu Glu Lys
            275                 280                 285

Val Ala Ala Thr Thr Gln Ala Gln Trp Pro Val His Ala Val Ile Thr
290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
            355                 360                 365

Leu Ala Ala Leu Ser Gln Ala Ser Leu Ile His Ile Lys Gly Glu Tyr
370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
            435                 440                 445

Trp Phe Phe Asp Ile Trp Gln Pro Pro Gln Val Asp Glu Ala Glu Cys
            450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
                485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
            595                 600                 605

Ala Phe Asp Thr Leu Pro Glu Met Ile Met Thr Pro His Gln Ala Trp
            610                 615                 620

Gln Arg Gln Ile Lys Gly Glu Val Glu Thr Ile Ala Leu Glu Gln Leu
625                 630                 635                 640
```

-continued

```
Val Gly Arg Val Ser Ala Asn Met Ile Leu Pro Tyr Pro Pro Gly Val
                645                 650             655

Pro Leu Leu Met Pro Gly Glu Met Leu Thr Lys Glu Ser Arg Thr Val
            660             665                 670

Leu Asp Phe Leu Leu Met Leu Cys Ser Val Gly Gln His Tyr Pro Gly
        675             680                 685

Phe Glu Thr Asp Ile His Gly Ala Lys Gln Asp Glu Asp Gly Val Tyr
    690             695                 700

Arg Val Arg Val Leu Lys Met Ala Gly
705             710
```

METHODS, REAGENTS AND CELLS FOR BIOSYNTHESIZING COMPOUNDS

CROSS REFERENCE TO RELATED APPLICATIONS

This application claims the benefit of U.S. Provisional Application Ser. No. 62/012,592, filed Jun. 16, 2014, the disclosure of which is incorporated herein by reference in its entirety.

TECHNICAL FIELD

This invention relates to methods for biosynthesizing glutaric acid, 5-aminopentanoic acid, cadaverine, 5-hydroxypentanoic acid, or 1,5-pentanediol (hereafter "C5 building blocks") using one or more isolated enzymes such as synthases, dehydratases, hydratases, dehydrogenases, decarboxylases, thioesterases, reversible CoA-ligases, CoA-transferases, carboxylate reductases, or ω-transaminases, and recombinant hosts that produce such C5 building blocks.

BACKGROUND

Nylons are polyamides which are generally synthesized by the condensation polymerization of a diamine with a dicarboxylic acid. Similarly, Nylons may be produced by the condensation polymerization of lactams. A ubiquitous nylon is Nylon 6,6, which is produced by condensation polymerization of hexamethylenediamine (HMD) and adipic acid. Nylon 6 can be produced by a ring opening polymerization of caprolactam (Anton & Baird, Polyamides Fibers, Encyclopedia of Polymer Science and Technology, 2001).

Nylon 5, Nylon 5,5 and other variants including C5 monomers represent novel polyamides with value-added characteristics compared to Nylon 6 and Nylon 6,6 in a number of applications. Nylon 5 is produced by polymerisation of 5-aminopentanoic acid, whereas Nylon 5,5 is produced by condensation polymerisation of glutaric acid and cadaverine. No economically viable petrochemical routes exist to producing the monomers for Nylon 5 and Nylon 5,5.

Given no economically viable petrochemical monomer feedstocks, biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

Accordingly, against this background, it is clear that there is a need for sustainable methods for producing one or more of glutaric acid, 5-hydroxypentanoate, 5-aminopentanoate, cadaverine and 1,5-pentanediol (hereafter "C5 building blocks") wherein the methods are biocatalyst based.

However, wild-type prokaryotes or eukaryotes do not overproduce such C5 building blocks to the extracellular environment. Nevertheless, the metabolism of glutaric acid, 5-aminopentanoate and cadaverine has been reported.

The dicarboxylic acid glutaric acid is converted efficiently as a carbon source by a number of bacteria and yeasts via β-oxidation into central metabolites. Decarboxylation of Coenzyme A (CoA) activated glutarate to crotonyl-CoA facilitates further catabolism via β-oxidation.

The metabolism of 5-aminopentanoate has been reported for anaerobic bacteria such as *Clostridium viride* (Buckel et al., 2004, *Arch. Microbiol.*, 162, 387-394). Similarly, cadaverine may be degraded to acetate and butyrate (Roeder and Schink, 2009, *Appl. Environ. Microbiol.*, 75(14), 4821-4828)

The optimality principle states that microorganisms regulate their biochemical networks to support maximum biomass growth. Beyond the need for expressing heterologous pathways in a host organism, directing carbon flux towards C5 building blocks that serve as carbon sources rather than as biomass growth constituents, contradicts the optimality principle. For example, transferring the 1-butanol pathway from *Clostridium* species into other production strains has often fallen short by an order of magnitude compared to the production performance of native producers (Shen et al., *Appl. Environ. Microbiol.*, 2011, 77(9):2905-2915).

The efficient synthesis of the five carbon aliphatic backbone precursor is a key consideration in synthesizing one or more C5 building blocks prior to forming terminal functional groups, such as carboxyl, amine or hydroxyl groups, on the C5 aliphatic backbone.

SUMMARY

This document is based at least in part on the discovery that it is possible to construct biochemical pathways for producing a five carbon chain backbone precursor such as glutaryl-CoA or 5-oxopentanoate (also known as glutarate semialdehyde), in which one or two functional groups, i.e., carboxyl, amine or hydroxyl, can be formed, leading to the synthesis of one or more of glutaric acid, 5-hydroxypentanoate, 5-aminopentanoate, cadaverine (also known as 1,5 pentanediamine), and 1,5-pentanediol (hereafter "C5 building blocks). Glutarate semialdehyde (also known as 5-oxopentanoic acid) can be produced as an intermediate to other products. Glutaric acid and glutarate, 5-hydroxypentanoic acid and 5-hydroxypentanoate, 5-oxopentanoic acid and 5-oxopentanoate, and 5-aminopentanoic and 5-aminopentanoate are used interchangeably herein to refer to the compound in any of its neutral or ionized forms, including any salt forms thereof. It is understood by those skilled in the art that the specific form will depend on pH.

In some embodiments, the C5 aliphatic backbone for conversion to a C5 building block can be formed from 2-oxoglutarate via conversion to 2-oxoadipate, followed by (i) decarboxylation of 2-oxoadipate to 5-oxopentanoate, (ii) dehydrogenation of the 2-oxoadipate to glutaryl-CoA or (iii) α-transamination of 2-oxoadipate to 2-amino-adipate and decarboxylation of 2-amino-adipate to 5-aminopentanoate. See FIG. 1, 2.

In some embodiments, an enzyme in the pathway generating the C5 aliphatic backbone purposefully contains irreversible enzymatic steps.

In some embodiments, the terminal carboxyl groups can be enzymatically formed using a thioesterase, a reversible CoA-ligase, a CoA-transferase, an aldehyde dehydrogenase, a 7-oxoheptanoate dehydrogenase, a 6-oxohexanoate dehydrogenase or a 5-oxopentanoate dehydrogenase. See FIG. 2.

In some embodiments, the terminal amine groups can be enzymatically formed using a decarboxylase, ω-transaminase or a deacetylase. See FIGS. 3-7.

In some embodiments, the terminal hydroxyl group can be enzymatically formed using an alcohol dehydrogenase, a 4-hydroxybutyrate dehydrogenase, a 5-hydroxypentanoate dehydrogenase and a 6-hydroxyhexanoate dehydrogenase. See FIG. 8 and FIG. 9.

The thioesterase can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO. 1, SEQ ID NO: 16-17.

The ω-transaminase can have at least 70% sequence identity (homology) (e.g., at least 75%, 80%, 85%, 90%, 91%, 92%, 93%, 94%, 95%, 96%, 97%, 98%, 99%, or 100%) to any one of the amino acid sequences set forth in SEQ ID NOs. 8-13.

A carboxylate reductase (e.g., in combination with a phosphopantetheinyl transferase) can form a terminal aldehyde group as an intermediate in forming the product. The carboxylate reductase can have at least 70% sequence identity (homology) (e.g., at least 75%, 80%, 85%, 90%, 91%, 92%, 93%, 94%, 95%, 96%, 97%, 98%, 99%, or 100%) to any one of the amino acid sequences set forth in SEQ ID NOs: 2-7.

The decarboxylase can have at least 70% sequence identity (homology) (e.g., at least 75%, 80%, 85%, 90%, 91%, 92%, 93%, 94%, 95%, 96%, 97%, 98%, 99%, or 100%) to any one of the amino acid sequences set forth in SEQ ID NOs. 1, 19-22.

Any of the methods can be performed in a recombinant host by fermentation. The host can be subjected to a cultivation strategy under aerobic, anaerobic, or micro-aerobic cultivation conditions. The host can be cultured under conditions of nutrient limitation such as phosphate, oxygen or nitrogen limitation. The host can be retained using a ceramic membrane to maintain a high cell density during fermentation.

In one aspect, this document features a method of biosynthesizing a C5 building block in a recombinant host. The method includes (i) enzymatically converting 2-oxo-adipate to an intermediate in the recombinant host using at least one polypeptide having an activity selected from the group consisting of alpha-aminotransferase activity, 2-oxoacid decarboxylase activity and activity of a 2-oxoglutarate dehydrogenase complex, wherein the intermediate is selected from the group consisting of 2-amino-adipate, 5-oxopentanoic acid, and glutaryl-CoA; and enzymatically converting the intermediate to the C5 building block in the recombinant host using at least one polypeptide having an activity selected from the group consisting of thioesterase activity, CoA-ligase activity, CoA-transferase activity, acylating dehydrogenase activity, aldehyde dehydrogenase activity, 5-hydroxypentanoate dehydrogenase activity, 6-hydroxyhexanoate dehydrogenase activity, alcohol dehydrogenase activity, carboxylate reductase activity, ω-transaminase activity, alpha-amino decarboxylase activity, N-acetyltransferase activity, and acetylputrescine deacetylase activity. The C5 building block is selected from the group consisting of glutaric acid, 5-hydroxypentanoic acid, 5-aminopentanoic acid, cadaverine, and 1,5-pentanediol.

The polypeptide having 2-oxoacid decarboxylase activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 1.

The polypeptide having the activity of a 2-oxoglutarate dehydrogenase complex can include activities classified under EC 1.2.4.2, EC 1.8.1.4 and EC 2.3.1.61.

The polypeptide having the activity of a 2-oxoglutarate dehydrogenase complex can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 16.

In some embodiments, the 2-oxo-adipate is obtained by enzymatically converting 2-oxo-glutarate to 2-oxo-adipate using at least one polypeptide having an activity selected from the group consisting of 2-isopropylmalate synthase activity, homocitrate synthase activity, homoaconitate hydratase activity, 3-isopropylmalate dehydratase activity, homoisocitrate dehydrogenase activity, and 3-isopropylmalate dehydrogenase activity.

In some embodiments, the polypeptide having carboxylate reductase activity is used in combination with a polypeptide having phosphopantetheine transferase enhancer activity.

In some embodiments, the intermediate is glutaryl-CoA and is enzymatically converted to glutaric acid using at least one polypeptide having an activity selected from the group consisting of thioesterase activity, CoA-ligase activity, acylating dehydrogenase activity, and aldehyde dehydrogenase activity.

The polypeptide having thioesterase activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 17 or 18.

In some embodiments, the intermediate is 5-oxopentanoic acid and is enzymatically converted to the C5 building block 5-aminopentanoic acid using a polypeptide having ω-transaminase activity.

In some embodiments, the intermediate is 2-amino-adipate and is enzymatically converted to the C5 building block 5-aminopentanoic acid using a polypeptide having alpha-amino decarboxylase activity.

The polypeptide having alpha-amino decarboxylase activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in any one of SEQ ID NOs: 19-22.

In some embodiments, the C5 building block is glutaric acid and the method further includes enzymatically converting glutaric acid to the C5 building block 5-aminopentanoic acid using at least one polypeptide having an activity selected from the group consisting of carboxylate reductase activity and ω-transaminase activity. The polypeptide having carboxylate reductase activity can be used in combination with a polypeptide having phosphopantetheine transferase enhancer activity.

In some embodiments, the intermediate is 5-oxopentanoic acid and is enzymatically converted to the C5 building block 5-hydroxypentanoic acid using at least one polypeptide having an activity selected from the group consisting of 5-hydroxypentanoate dehydrogenase activity, 6-hydroxyhexanoate dehydrogenase activity, and alcohol dehydrogenase activity.

In some embodiments, the C5 building block is glutaric acid and the method further includes enzymatically converting the glutaric acid to the C5 building block 5-hydroxypentainoic acid using at least one polypeptide having an activity selected from the group consisting of carboxylate reductase activity and alcohol dehydrogenase activity. The polypeptide having carboxylate reductase activity can be used in combination with a polypeptide having phosphopantetheine transferase enhancer activity.

In some embodiments, C5 building block is 5-aminopentanoic acid and the method further includes enzymatically converting 5-aminopentanoic acid to the C5 building block cadaverine using at least one polypeptide having an activity selected from the group consisting of carboxylate reductase activity and ω-transaminase activity. The polypeptide having carboxylate reductase activity can be used in combination with a polypeptide having phosphopantetheine transferase enhancer activity.

In some embodiments, the C5 building block is 5-hydroxypentanoic acid and the method further includes enzymatically converting 5-hydroxypentanoic acid to the C5 building block cadaverine using at least one polypeptide having an activity selected from the group consisting of carboxylate reductase activity, ω-transaminase activity, and alcohol dehydrogenase activity. The polypeptide having carboxylate reductase activity can be used in combination with a polypeptide having phosphopantetheine transferase enhancer activity.

In some embodiments, the intermediate is 5-oxopentanoic acid and is enzymatically converted to the C5 building block cadaverine using at least one polypeptide having an activity selected from the group consisting of carboxylate reductase activity and ω-transaminase activity. The polypeptide having carboxylate reductase activity can be used in combination with a polypeptide having phosphopantetheine transferase enhancer activity.

In some embodiments, the C5 building block is 5-hydroxypentanoic acid and the method further includes enzymatically converting the 5-hydroxypentanoic acid to the C5 building block 1,5-pentanediol using at least one polypeptide having an activity selected from the group consisting of carboxylate reductase activity and alcohol dehydrogenase activity. The polypeptide having carboxylate reductase activity is used in combination with a polypeptide having phosphopantetheine transferase enhancer activity. The method can further include enzymatically converting the 1,5-pentanediol to the C5 building block cadaverine using at least one polypeptide having an activity selected from the group consisting of alcohol dehydrogenase activity and ω-transaminase activity.

In some embodiments, the C5 building block is 5-aminopentanoic acid and the method further includes enzymatically converting the 5-aminopentanoic acid to the C5 building block cadaverine using at least one polypeptide having an activity selected from the group consisting of N-acetyltransferase activity, carboxylate reductase activity, ω-transaminase activity, and deacetylase activity. The polypeptide having carboxylate reductase activity can be used in combination with a polypeptide having phosphopantetheine transferase enhancer activity.

The polypeptide having carboxylate reductase activity can at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in any one of SEQ ID NOs: 2-7.

The polypeptide having ω-transaminase activity has at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in any one of SEQ ID NOs: 8-13.

The polypeptide having phosphopantetheine transferase enhancer activity has at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 14 or 15.

In some embodiments, the host is subjected to a cultivation strategy under aerobic or micro-aerobic cultivation conditions.

In some embodiments, the host is cultured under conditions of nutrient limitation either via nitrogen, phosphate or oxygen limitation.

In some embodiments, the host is retained using a ceramic membrane to maintain a high cell density during fermentation.

In some embodiments, the method further includes a principal carbon source fed to the fermentation derived from a biological feedstock.

In some embodiments, the biological feedstock is, or derives from monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the method further includes a principal carbon source fed to the fermentation derived from a non-biological feedstock. The non-biological feedstock can be, or can be derived from, natural gas, syngas, $CO_2/H_2$, methanol, ethanol, benzoate, non-volatile residue (NVR) or a caustic wash waste stream from cyclohexane oxidation processes, terephthalic acid/isophthalic acid mixture waste streams, or combinations thereof.

In some embodiments, the host exhibits tolerance to high concentrations of a C5 building block. In some embodiments the tolerance to high concentrations of a C5 building block is improved through continuous cultivation in a selective environment.

In some embodiments, the host includes one or more of the following attenuations: a polyhydroxyalkanoate synthase, an acetyl-CoA thioesterase, an acetyl-CoA specific β-ketothiolase, an acetoacetyl-CoA reductase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the cofactor imbalance, an NADH-specific glutamate dehydrogenase, a NADH/NADPH-utilizing glutamate dehydrogenase, a glutaryl-CoA dehydrogenase or an acyl-CoA dehydrogenase accepting C5 building blocks and central precursors as substrates.

Any of the recombinant hosts described herein further can overexpress one or more genes encoding a polypeptide having an activity selected from the group consisting of: an acetyl-CoA synthetase, a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a propionyl-CoA synthetase; a L-alanine dehydrogenase; an NADPH-specific L-glutamate dehydrogenase; a PEP carboxylase, a pyruvate carboxylase, PEP carboxykinase, PEP synthase, a L-glutamine synthetase; a lysine transporter; a dicarboxylate transporter; and/or a multidrug transporter activity.

In another aspect, this document features a recombinant host cell. The recombinant host cell includes at least one exogenous nucleic acid encoding at least one polypeptide having an activity selected from the group consisting of alpha-aminotransferase activity, 2-oxoacid decarboxylase activity and activity of a 2-oxoglutarate dehydrogenase complex, the host producing an intermediate from 2-oxoadipate, wherein the intermediate is selected from the group consisting of 2-amino-adipate, 5-oxopentanoic acid, and glutaryl-CoA. The recombinant host cell further includes at least one exogenous nucleic acid encoding at least one polypeptide having an activity selected from the group consisting of thioesterase activity, CoA-ligase activity, CoA-transferase activity, acylating dehydrogenase activity, aldehyde dehydrogenase activity, 5-hydroxypentanoate dehydrogenase activity, 6-hydroxyhexanoate dehydrogenase activity, alcohol dehydrogenase activity, carboxylate reductase activity, ω-transaminase activity, alpha-amino decarboxylase activity, N-acetyltransferase activity, and deacetylase activity, the host producing a C5 building block from the intermediate, wherein the C5 building block is selected from the group consisting of glutaric acid, 5-hydroxypentanoic acid, 5-aminopentanoic acid, cadaverine, and 1,5-pentanediol.

The polypeptide having 2-oxoacid decarboxylase activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 1.

The polypeptide having the activity of a 2-oxoglutarate dehydrogenase complex can include activities classified under EC 1.2.4.2, EC 1.8.1.4 and EC 2.3.1.61.

The polypeptide having the activity of a 2-oxoglutarate dehydrogenase complex can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 16.

The host can further include one or more exogenous polypeptides having an activity selected from the group consisting of 2-isopropylmalate synthase activity, homocitrate synthase activity, homoaconitate hydratase activity, 3-isopropylmalate dehydratase activity, homoisocitrate dehydrogenase activity, and 3-isopropylmalate dehydrogenase activity, the host producing 2-oxo-adipate from 2-oxoglutarate.

The host can further include an exogenous polypeptide having phosphopantetheine transferase enhancer activity.

In some embodiments, the host includes one or more exogenous polypeptides having an activity selected from the group consisting of thioesterase activity, CoA-transferase activity, CoA-ligase activity, acylating dehydrogenase activity, carboxylate reductase activity, and aldehyde dehydrogenase activity, the host producing the C5 building block glutaric acid from the intermediate glutaryl-CoA. In some embodiments, the host includes an exogenous polypeptide having dehydrogenase activity, the host producing the intermediate 5-oxopentanoic acid from glutaryl-CoA The polypeptide having thioesterase activity has at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 17 or 18.

In some embodiments, the host includes an exogenous polypeptide having ω-transaminase activity, the host producing C5 building block 5-aminopentanoic acid from 5-oxopentanoic acid.

In some embodiments, the host includes an exogenous polypeptides having alpha-amino decarboxylase activity, the host producing the C5 building block 5-aminopentanoic acid from the intermediate 2-amino-adipate.

The polypeptide having alpha-amino decarboxylase activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in any one of SEQ ID NOs: 19-22.

In some embodiments, the host includes one or more exogenous polypeptides having an activity selected from the group consisting of carboxylate reductase activity and ω-transaminase activity, the host producing the C5 building block 5-aminopentanoic acid from the C5 building block glutaric acid.

In some embodiments, the host includes one or more exogenous polypeptides having an activity selected from the group consisting of 5-hydroxypentanoate dehydrogenase activity and 6-hydroxyhexanoate dehydrogenase activity, the host producing the C5 building block 5-hydroxypentanoic acid from the intermediate is 5-oxopentanoic acid.

In some embodiments, the host includes one or more exogenous polypeptides having an activity selected from the group consisting of carboxylate reductase activity and alcohol dehydrogenase activity, the host producing the C5 building block 5-hydroxypentainoic acid from the C5 building block glutaric acid. The host can further include an exogenous polypeptide having phosphopantetheine transferase enhancer activity.

In some embodiments, the host includes one or more exogenous polypeptides having an activity selected from the group consisting of carboxylate reductase activity and ω-transaminase activity, the host producing the C5 building block cadaverine from the C5 building block 5-aminopentanoic acid. The host can further include an exogenous polypeptide having phosphopantetheine transferase enhancer activity.

In some embodiments, the host includes one or more exogenous polypeptides having an activity selected from the group consisting of carboxylate reductase activity, ω-transaminase activity, and alcohol dehydrogenase activity, the host producing the C5 building block cadaverine from the C5 building block 5-hydroxypentanoic acid.

In some embodiments, the host includes one or more exogenous polypeptides having an activity selected from the group consisting of carboxylate reductase activity and ω-transaminase activity, the host producing the C5 building block cadaverine from the intermediate 5-oxopentanoic acid. The host can further include an exogenous polypeptide having phosphopantetheine transferase enhancer activity.

In some embodiments, the host includes one or more exogenous polypeptides having an activity selected from the group consisting of carboxylate reductase activity and alcohol dehydrogenase activity, the host producing the C5 building block 1,5-pentanediol from the C5 building block 5-hydroxypentanoic acid. The host can further include one or more exogenous polypeptides having an activity selected from the group consisting of ω-transaminase activity and alcohol dehydrogenase activity, the host producing the C5 building block cadaverine from the C5 building block 1,5-pentanediol. The host can further include an exogenous polypeptide having phosphopantetheine transferase enhancer activity.

In some embodiments, the host includes one or more exogenous polypeptides having an activity selected from the group consisting of N-acetyltransferase activity, carboxylate reductase activity, ω-transaminase activity, and deacetylase activity, the host producing the C5 building block cadaverine form the C5 building block 5-aminopentanoic acid. The host can further include an exogenous polypeptide having phosphopantetheine transferase enhancer activity.

The polypeptide having carboxylate reductase activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in any one of SEQ ID NOs: 2-7.

The polypeptide having ω-transaminase activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in any one of SEQ ID NOs: 8-13.

The polypeptide having phosphopantetheine transferase enhancer activity can have at least 70% sequence identity (homology) (e.g., at least 75%, 80%, 85%, 90%, 91%, 92%, 93%, 94%, 95%, 96%, 97%, 98%, 99%, or 100%) to the amino acid sequence set forth in SEQ ID NO: 14 or 15.

In one aspect, this document features a method for producing a bioderived five carbon compound. The method for producing the bioderived five carbon compound can include culturing or growing a host as described herein under conditions and for a sufficient period of time to produce the bioderived five carbon compound, wherein, optionally, the bioderived five carbon compound is selected from the group consisting of glutaric acid, 5-hydroxypentanoic acid, 5-aminopentanoic acid, cadaverine, 1,5-pentanediol, and combinations thereof.

In one aspect, this document features compositions comprising a bioderived five carbon compound as described herein and a compound other than the bioderived five carbon compound, wherein the bioderived five carbon compound is selected from the group consisting of glutaric acid, 5-hydroxypentanoic acid, 5-aminopentanoic acid, cadaverine, 1,5-pentanediol, and combinations thereof. For example, the bioderived five carbon compound is a cellular portion of a host cell or an organism.

This document also features a biobased polymer comprising the bioderived glutaric acid, 5-hydroxypentanoic acid, 5-aminopentanoic acid, cadaverine, 1,5-pentanediol, and combinations thereof.

This document also features a biobased resin comprising the bioderived glutaric acid, 5-hydroxypentanoic acid, 5-aminopentanoic acid, cadaverine, 1,5-pentanediol, and combinations thereof, as well as a molded product obtained by molding a biobased resin.

In another aspect, this document features a process for producing a biobased polymer that includes chemically reacting the bioderived glutaric acid, 5-hydroxypentanoic acid, 5-aminopentanoic acid, cadaverine, 1,5-pentanediol, with itself or another compound in a polymer producing reaction.

In another aspect, this document features a bio-derived product, bio-based product or fermentation-derived product, wherein the product includes (i.) a composition including at least one bio-derived, bio-based or fermentation-derived compound as described herein, or any combination thereof; (ii.) a bio-derived, bio-based or fermentation-derived polymer comprising the bio-derived, bio-based or fermentation-derived composition or compound of (i.), or any combination thereof; (iii.) a bio-derived, bio-based or fermentation-derived resin comprising the bio-derived, bio-based or fermentation-derived compound or bio-derived, bio-based or fermentation-derived composition of (i.) or any combination thereof or the bio-derived, bio-based or fermentation-derived polymer of ii. or any combination thereof; (iv.) a molded substance obtained by molding the bio-derived, bio-based or fermentation-derived polymer of (ii.) or the bio-derived, bio-based or fermentation-derived resin of (iii.), or any combination thereof; (v.) a bio-derived, bio-based or fermentation-derived formulation comprising the bio-derived, bio-based or fermentation-derived composition of (i.), bio-derived, bio-based or fermentation-derived compound of (i.), bio-derived, bio-based or fermentation-derived polymer of (ii.), bio-derived, bio-based or fermentation-derived resin of (iii.), or bio-derived, bio-based or fermentation-derived molded substance of (iv.), or any combination thereof; or (vi.) a bio-derived, bio-based or fermentation-derived semi-solid or a non-semi-solid stream, comprising the bio-derived, bio-based or fermentation-derived composition of (i.), bio-derived, bio-based or fermentation-derived compound of (i.), bio-derived, bio-based or fermentation-derived polymer of (ii.), bio-derived, bio-based or fermentation-derived resin of (iii.), bio-derived, bio-based or fermentation-derived formulation of (v.), or bio-derived, bio-based or fermentation-derived molded substance of (iv.), or any combination thereof.

Also described herein is a biochemical network including at least one enzyme selected from the group consisting of an alpha-aminotransferase, a 2-oxoacid decarboxylase and a 2-oxoglutarate dehydrogenase complex and 2-oxo-adipate wherein the alpha-aminotransferase, the 2-oxoacid decarboxylase or the 2-oxoglutarate dehydrogenase enzymatically convert the 2-oxo-adipate to an intermediate. The intermediate is selected from the group consisting of 2-amino-adipate, 5-oxopentanoic acid, and glutaryl-CoA. The biochemical network further includes at least one enzyme selected from the group consisting of a thioesterase, a CoA-ligase, a CoA-transferase, an acylating dehydrogenase, an aldehyde dehydrogenase, a 5-hydroxypentanoate dehydrogenase, a 6-hydroxyhexanoate dehydrogenase, an alcohol dehydrogenase, a carboxylate reductase, an ω-transaminase, an alpha-amino decarboxylase, an N-acetyltransferase, and an acetylputrescine deacetylase and the intermediate wherein the at least one of the thioesterase, the CoA-ligase, the CoA-transferase, the acylating dehydrogenase, the aldehyde dehydrogenase, the 5-hydroxypentanoate dehydrogenase, the 6-hydroxyhexanoate dehydrogenase, the alcohol dehydrogenase, the carboxylate reductase, the ω-transaminase, the alpha-amino decarboxylase, the N-acetyltransferase, and the acetylputrescine deacetylase enzymatically converts the intermediate to a C5 building block. The C5 building block is selected from the group consisting of glutaric acid, 5-hydroxypentanoic acid, 5-aminopentanoic acid, cadaverine, and 1,5-pentanediol.

The biochemical network can further include a 2-isopropylmalate synthase, a homocitrate synthase, a homoaconitate hydratase, a 3-isopropylmalate dehydratase, a homoisocitrate dehydrogenase, a 3-isopropylmalate dehydrogenase, an alpha-aminotransferase, a 2-oxoacid decarboxylase or a 2-oxoglutarate dehydrogenase complex and 2-oxo-glutarate wherein the 2-isopropylmalate synthase, the homocitrate synthase, the homoaconitate hydratase, the 3-isopropylmalate dehydratase, the homoisocitrate dehydrogenase, the 3-isopropylmalate dehydrogenase, the alpha-aminotransferase, the 2-oxoacid decarboxylase or the 2-oxoglutarate dehydrogenase enzymatically converts 2-oxo-gluterate to 2-oxo-adipate.

The biochemical network can further include a phosphopantetheine transferase enhancer.

The biochemical network can include one or more of a thioesterase, a CoA-ligase, an acylating dehydrogenase, and an aldehyde dehydrogenase and the glutaryl-CoA wherein the one or more of the thioesterase, the CoA-ligase, the acylating dehydrogenase, and the aldehyde dehydrogenase enzymatically converts the glutaryl-CoA to glutaric acid.

The biochemical network can include a ω-transaminase and 5-oxopentanoic acid, wherein the ω-transaminase enzymatically converts the 5-oxopentanoic to 5-aminopentanoic acid.

The biochemical network can include an alpha-amino decarboxylase and 2-amino-adipate, wherein the alpha-amino decarboxylase enzymatically converts the 2-amino-adipate to 5-aminopentanoic acid.

The biochemical network can include one or more of a carboxylate reductase activity and a ω-transaminase, and glutaric acid, wherein one or more of the carboxylate reductase activity and the ω-transaminase enzymatically convert the glutaric acid to 5-aminopentanoic acid.

The biochemical network can include one or more of a 5-hydroxypentanoate dehydrogenase and 6-hydroxyhexanoate dehydrogenase, and 5-oxopentanoic acid wherein one or more of the 5-hydroxypentanoate dehydrogenase and the 6-hydroxyhexanoate dehydrogenase enzymatically convert 5-oxopentanoic acid to 5-hydroxypentanoic acid.

The biochemical network can include one or more of a carboxylate reductase and an alcohol dehydrogenase, and glutaric acid wherein one or more of the carboxylate reductase and the alcohol dehydrogenase enzymatically convert the glutaric acid to 5-hydroxypentainoic acid.

The biochemical network can include one or more of a carboxylate reductase, a ω-transaminase, and an alcohol dehydrogenase and 5-hydroxypentanoic acid, wherein one or more of the carboxylate reductase, the ω-transaminase, and the alcohol dehydrogenase enzymatically converts 5-hydroxypentanoic acid to cadaverine.

The biochemical network can include one or more of a carboxylate reductase and a ω-transaminase and 5-oxopentanoic acid, wherein one or more of the carboxylate reductase and a ω-transaminase enzymatically convert the 5-oxopentanoic acid cadaverine.

The biochemical network can include one or more of a carboxylate reductase and an alcohol dehydrogenase and 5-hydroxypentanoic acid, wherein one or more of the carboxylate reductase and the alcohol dehydrogenase enzymatically convert the 5-hydroxypentanoic acid to 1,5-pentanediol.

The biochemical network can include an ω-transaminase and 1,5-pentanediol wherein the ω-transaminase enzymatically converts the 1,5-pentanediol to cadaverine.

The biochemical network can include one or more of a N-acetyltransferase, a carboxylate reductase, a ω-transaminase, and an acetylputrescine deacetylase and 5-aminopentanoic acid wherein one or more of the N-acetyltransferase, the carboxylate reductase, the ω-transaminase, and the acetylputrescine deacetylase enzymatically convert the 5-aminopentanoic acid to cadaverine.

The biochemical network can further include phosphopantetheine transferase enhancer when a carboxylate reductase is present in the biochemical network.

This document also features a recombinant host that includes at least one exogenous nucleic acid encoding a (i) 2-oxoaciddecarboxylase or a 2-oxoglutaryl-CoA dehydrogenase complex and (ii) a synthase, hydratase and dehydrogenase, and produce 5-oxopentanoate (also known as glutarate semialdehyde) or glutaryl-CoA. Such a recombinant host producing 5-oxopentanoate further can include one or more of an aldehyde dehydrogenase such as 7-oxoheptanoate dehydrogenase, 6-oxohexanoate dehydrogenase or 5-oxopentanoate dehydrogenase and further produce glutaric acid. Such a recombinant host producing glutaryl-CoA further can include one or more of (i) a thioesterase, (ii) a reversible CoA-ligase, (iii) a CoA-transferase, or (iv) an acylating dehydrogenase, and (v) an aldehyde dehydrogenase and further produce glutaric acid or 5-oxopentanoate.

This document further features a recombinant host that includes at least one exogenous nucleic acid encoding a (i) an alpha-aminodecarboxylase and (ii) a synthase, a hydratase, a dehydrogenase and an alpha-amino transaminase, and produce 5-aminopentanoate.

A recombinant host producing 5-oxopentanoate or glutaric acid further can include one or more of (i) a ω-transaminase or (ii) a carboxylate reductase and further produce 5-aminopentanoate.

A recombinant host producing 5-oxopentanoate or glutaric acid further can include one or more of (i) an alcohol dehydrogenase or (ii) a carboxylate reductase and further produce 5-hydroxypentanoate.

A recombinant host producing 5-hydroxypentanoate can further include one or more of (i) a carboxylase reductase and (ii) an alcohol dehydrogenase, the host further producing 1,5-pentanediol.

A recombinant host producing 5-hydroxypentanoate can further include one or more of (i) a carboxylase reductase, (ii) one or more ω-transaminases and (iii) an alcohol dehydrogenase, the host further producing cadaverine.

A recombinant host producing 5-aminopentanoate can further include one or more of (i) a carboxylase reductase and (ii) a ω-transaminase, the host further producing cadaverine.

A recombinant host producing 5-oxopentanoate can further include one or more of (i) a carboxylase reductase and (ii) one or more ω-transaminases, the host further producing cadaverine.

A recombinant host producing 1,5-pentanediol can further include (i) one or more alcohol dehydrogenases and (ii) one or more ω-transaminases, the host further producing cadaverine.

A recombinant host producing 5-aminopentanoate can further include one or more of (i) an N-acetyltransferase, (ii) a carboxylate reductase, (iii) a ω-transaminase and (iv) an acetylase, the host further producing cadaverine.

In any of the embodiments described herein, the recombinant host can be a prokaryote, e.g., from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia acidovorans*, from the genus *Bacillus* such as *Bacillus subtillis*; from the genes *Lactobacillus* such as *Lactobacillus delbrueckii*; from the genus *Lactococcus* such as *Lactococcus lactis* or from the genus *Rhodococcus* such as *Rhodococcus equi*.

In any of the embodiments described herein, the recombinant host can be a eukaryote, e.g., a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

In some embodiments, the host's endogenous biochemical network is attenuated or augmented to (1) ensure the intracellular availability of 2-oxoglutarate, (2) create a NADPH cofactor imbalance that may be balanced via the formation of C5 building blocks, (3) prevent degradation of central metabolites, central precursors leading to and including C5 building blocks and (4) ensure efficient efflux from the cell.

Any of the recombinant hosts described herein further can include one or more of the following attenuated enzymes: polyhydroxyalkanoate synthase, an acetyl-CoA thioesterase, an acetyl-CoA specific β-ketothiolase, an acetoacetyl-CoA reductase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the cofactor imbalance, an NADH-specific glutamate dehydrogenase, a NADH/NADPH-utilizing glutamate dehydrogenase, a glutaryl-CoA dehydrogenase or an acyl-CoA dehydrogenase accepting C5 building blocks and central precursors as substrates.

Any of the recombinant hosts described herein further can overexpress one or more genes encoding: an acetyl-CoA synthetase, a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a propionyl-CoA synthetase; a L-alanine dehydrogenase; an NADPH-specific L-glutamate dehydrogenase; a PEP carboxylase, a pyruvate carboxylase, PEP carboxykinase, PEP synthase, a L-glutamine synthetase; a lysine transporter; a dicarboxylate transporter; and/or a multidrug transporter.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Extracted enzymes can optionally be immobilized to the floors and/or walls of appropriate reaction vessels. Moreover, such extracts include lysates (e.g. cell lysates) that can be used as sources of relevant enzymes. In the methods provided by the document, all the steps can be performed in cells (e.g., host cells), all the steps can be performed using extracted enzymes, or some of the steps can be performed in cells and others can be performed using extracted enzymes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein including GenBank and NCBI submissions with accession numbers are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

One of skill in the art understands that compounds containing carboxylic acid groups (such as but not limited to organic monoacids, hydroxyacids, aminoacids and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

One of skill in the art understands that compounds containing carboxylic acid groups (including, but not limited to, organic monoacids, hydroxyacids, aminoacids, and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

One of skill in the art understands that compounds containing amine groups (including, but not limited to, organic amines, aminoacids, and diamines) are formed or converted to their ionic salt form, for example, by addition of an acidic proton to the amine to form the ammonium salt, formed with inorganic acids such as hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free amine by raising the pH to above the pKb through addition of base or treatment with a basic ion exchange resin.

One of skill in the art understands that compounds containing both amine groups and carboxylic acid groups (including, but not limited to, aminoacids) are formed or converted to their ionic salt form by either 1) acid addition salts, formed with inorganic acids including, but not limited to, hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt can of the present invention is isolated as a salt or converted to the free acid by reducing the pH to below the pKa through addition of acid or treatment with an acidic ion exchange resin.

DESCRIPTION OF DRAWINGS

FIG. 10 contains the amino acid sequences of a *Salmonella typhimurium* indolepyruvate decarboxylase (see Genbank Accession No. CAC48239.1, SEQ ID NO: 1), a *Mycobacterium marinum* carboxylate reductase (see Genbank Accession No. ACC40567.1, SEQ ID NO: 2), a *Mycobacterium smegmatis* carboxylate reductase (see Genbank Accession No. ABK71854.1, SEQ ID NO: 3), a *Segniliparus rugosus* carboxylate reductase (see Genbank Accession No. EFV11917.1, SEQ ID NO: 4), a *Mycobacterium smegmatis* carboxylate reductase (see Genbank Accession No. ABK75684.1, SEQ ID NO: 5), a *Mycobacterium massiliense* carboxylate reductase (see Genbank Accession No. EIV11143.1, SEQ ID NO: 6), a *Segniliparus rotundus* carboxylate reductase (see Genbank Accession No. ADG98140.1, SEQ ID NO: 7), a *Chromobacterium violaceum* ω-transaminase (see Genbank Accession No. AAQ59697.1, SEQ ID NO: 8), a *Pseudomonas aeruginosa* ω-transaminase (see Genbank Accession No. AAG08191.1, SEQ ID NO: 9), a *Pseudomonas syringae* ω-transaminase (see Genbank Accession No. AAY39893.1, SEQ ID NO: 10), a *Rhodobacter sphaeroides* ω-transaminase (see Genbank Accession No. ABA81135.1, SEQ ID NO: 11), an *Escherichia coli* ω-transaminase (see Genbank Accession No. AAA57874.1, SEQ ID NO: 12), a *Vibrio fluvialis* ω-transaminase (See Genbank Accession No. AEA39183.1, SEQ ID NO: 13), a *Bacillus subtilis* phosphopantetheinyl transferase (see Genbank Accession No. CAA44858.1, SEQ ID NO: 14), a *Nocardia* sp. NRRL 5646 phosphopantetheinyl transferase (see Genbank Accession No. ABI83656.1, SEQ ID NO: 15), an *Azotobacter vinelandii* 2-oxoglutarate dehydrogenase complex (see Genbank Accession Nos. CAA36680.1 & CAA36678.1 & CAA36679.1, SEQ ID NO: 16), a *Lactobacillus brevis* acyl-[acp] thioesterase (see Genbank Accession Nos. ABJ63754.1, SEQ ID NO: 17), a *Lactobacillus plantarum* acyl-[acp] thioesterase (see Genbank Accession Nos. ABJ63754.1, SEQ ID NO: 18), an *Escherichia coli* glutamate decarboxylase (see Genbank Accession No. AAA23833.1, SEQ ID: 19), an *Escherichia coli* lysine decarboxylase (see Genbank Accession No. AAA23536.1, SEQ ID: 20), an *Escherichia coli* ornithine decarboxylase (see Genbank Accession No. AAA62785.1, SEQ ID: 21), an *Escherichia coli* lysine decarboxylase (see Genbank Accession No. BAA21656.1, SEQ ID: 22).

DETAILED DESCRIPTION

Figure 1:
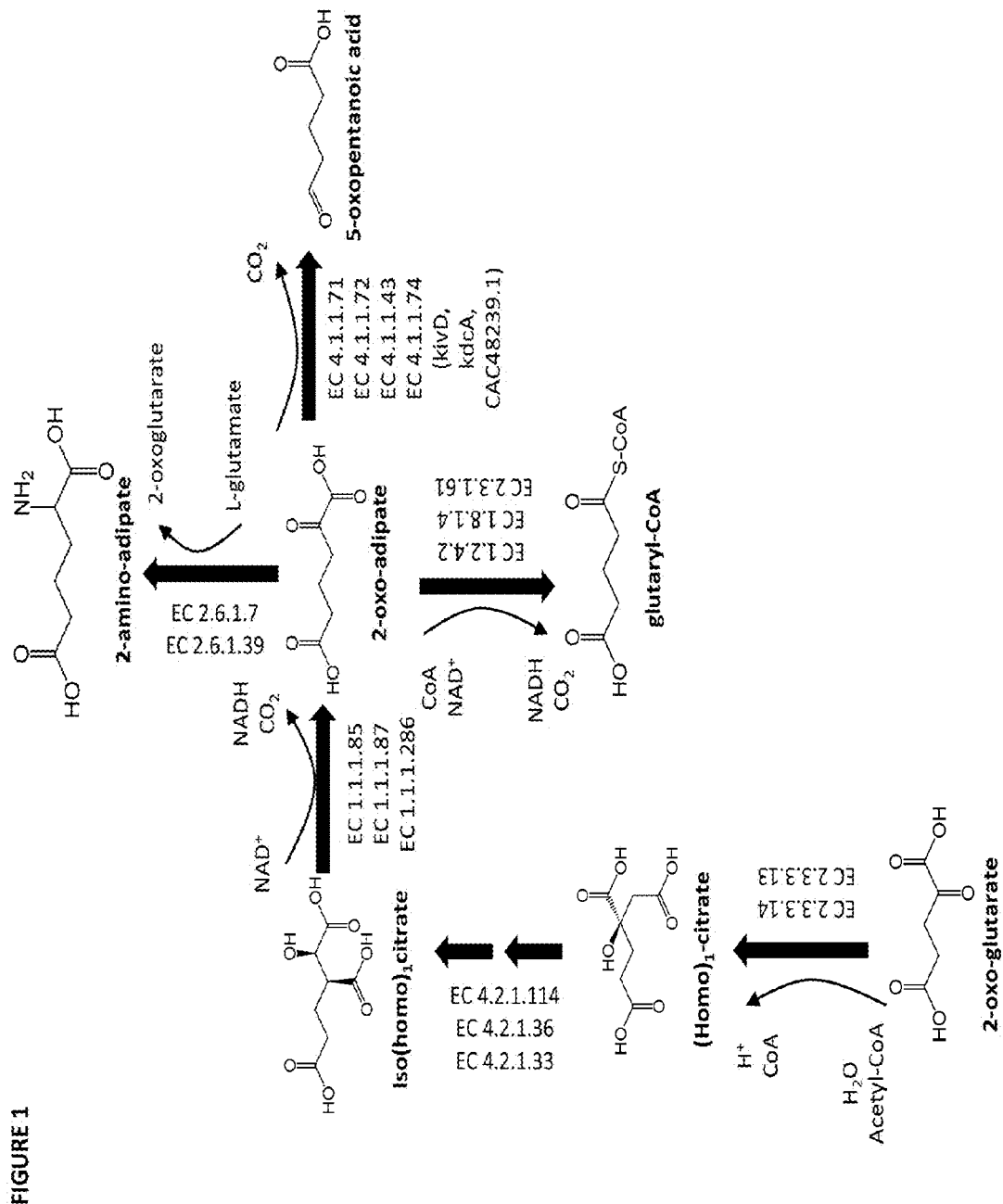
FIG. 1 is a schematic of exemplary biochemical pathways leading to glutaryl-CoA, 2-amino-adipate, or 5-oxopentanoic acid from 2-oxo-glutarate.

This document provides enzymes, non-natural pathways, cultivation strategies, feedstocks, host microorganisms and attenuations to the host's biochemical network, which generates a five carbon chain backbone such as glutaryl-CoA or 5-oxopentanoate (also known as glutarate semialdehyde) from central metabolites in which one or two terminal functional groups may be formed leading to the synthesis of one or more of glutaric acid, 5-aminopentanoic acid, cadaverine (also known as 1,5 pentanediamine), 5-hydroxypentanoic acid, or 1,5-pentanediol (hereafter "C5 building blocks"). Glutarate semialdehyde (also known as 5-oxopentanoate) can be produced as an intermediate to other products. As used herein, the term "central precursor" is used to denote any metabolite in any metabolic pathway shown herein leading to the synthesis of a C5 building block. The term "central metabolite" is used herein to denote a metabolite that is produced in all microorganisms to support growth.

Host microorganisms described herein can include endogenous pathways that can be manipulated such that one or more C5 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host including (i) a homocitrate synthase or a 2-isopropylmalate synthase, (ii) a homoaconitate hydratase or a 3-isopropylmalate dehydratase (iii) a homoisocitrate dehydrogenase or 3-isopropylmalate dehydrogenase, (iv) a 2-oxoacid decarboxylase, a 2-oxoglutarate dehydrogenase complex or an alpha-amino decarboxylase, a 4-hydroxybutyrate dehydrogenase, a 5-hydroxypentanoate dehydrogenase, a 6-hydroxyhexanoate dehydrogenase, an alcohol dehydrogenase, a 5-oxopentanoate dehydrogenase, a 6-oxohexanoate dehydrogenase, a 7-oxoheptanoate dehydrogenase, an aldehyde dehydrogenase, a ω-transaminase, or a carboxylate reductase. In recombinant hosts expressing a carboxylate reductase, a phosphopantetheinyl transferase also can be expressed as it enhances activity of the carboxylate reductase.

In some embodiments, a recombinant host can include at least one exogenous nucleic acid encoding one or more of a (i) a homocitrate synthase or a 2-isopropylmalate synthase, (ii) a homoaconitate hydratase or a 3-isopropylmalate dehydratase (iii) a homoisocitrate dehydrogenase or 3-isopropylmalate dehydrogenase, and produce 2-oxoadipate.

In some embodiments, a recombinant host that produces 2-oxoadipate can include at least one exogenous nucleic acid encoding a 2-oxoacid decarboxylase or a 2-oxoglutarate dehydrogenase complex, and further produce 5-oxopentanoate or glutaryl-CoA.

In some embodiments, a recombinant host producing 5-oxopentanoate includes at least one exogenous nucleic acid encoding an aldehyde dehydrogenase such as a succinate semialdehyde dehydrogenase, a 5-oxopentanoate dehydrogenase, a 6-oxohexanoate dehydrogenase, or a 7-oxoheptanoate dehydrogenase and produces glutarate.

In some embodiments, a recombinant host producing glutaryl-CoA includes at least one exogenous nucleic acid encoding a (i) a thioesterase, (ii) a reversible CoA-ligase, (iii) a CoA-transferase, or (iv) an acylating dehydrogenase, and (v) an aldehyde dehydrogenase and further produce glutaric acid or 5-oxopentanoate.

In some embodiments, a recombinant host that produces 2-oxoadipate can include at least one exogenous nucleic acid encoding an alpha-amino transaminase and an alpha-amino decarboxylase, and further produce 5-aminopentanoate.

In some embodiments, a recombinant host that produces 5-oxopentanoate can include at least one exogenous nucleic acid encoding (i) a reversible ω-transaminase (e.g., a 5-aminovalerate transaminase) and produce 5-aminopentanoate.

In some embodiments, a recombinant host that produces 5-oxopentanoate can include at least one exogenous nucleic acid encoding an alcohol dehydrogenase such as 4-hydroxybutyrate dehydrogenase, a 5-hydroxypentanoate dehydrogenase, a 6-hydroxyhexanoate dehydrogenase, and further produce 5-hydroxypentanoate.

A recombinant host producing 5-hydroxypentanoic acid further can include one or more of (i) a carboxylate reductase and (ii) an alcohol dehydrogenase, and produce 1,5-pentanediol.

A recombinant host producing 5-aminopentanoate, 5-hydroxypentanoate, 1,5-pentanediol or glutarate semialdehyde further can include one or more of (i) a carboxylate reductase, (ii) a ω-transaminase, (iii) a N-acetyltransferase, (iv) an alcohol dehydrogenase and (v) a deacetylase, and produce cadaverine.

Within an engineered pathway, the enzymes can be from a single source, i.e., from one species or genus, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C5 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a 2-oxoacid decarboxylase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Salmonella typhimurium* indolepyruvate decarboxylase (see Genbank Accession No. CAC48239.1, SEQ ID NO: 1). See, FIG. 1.

For example, a carboxylate reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium smegmatis* (see Genbank Accession No. ABK75684.1, SEQ ID NO: 5), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7) carboxylate reductase. See, FIG. 4 and FIG. 9.

Figure 6:
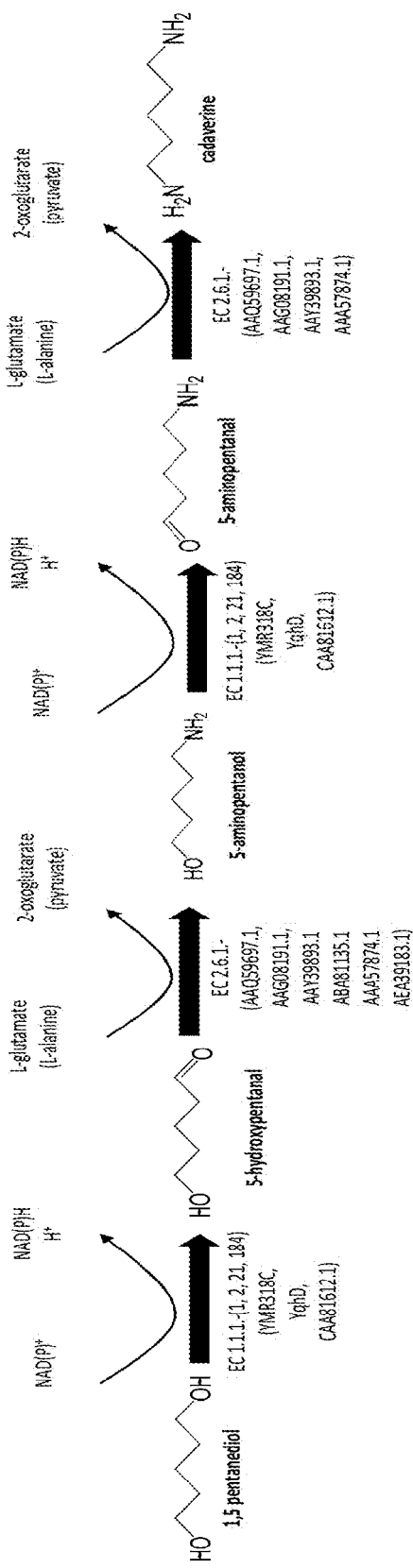
FIG. 6 is a schematic of an exemplary biochemical pathway leading to cadaverine using 1,5-pentanediol as a central precursor.
Figure 7:
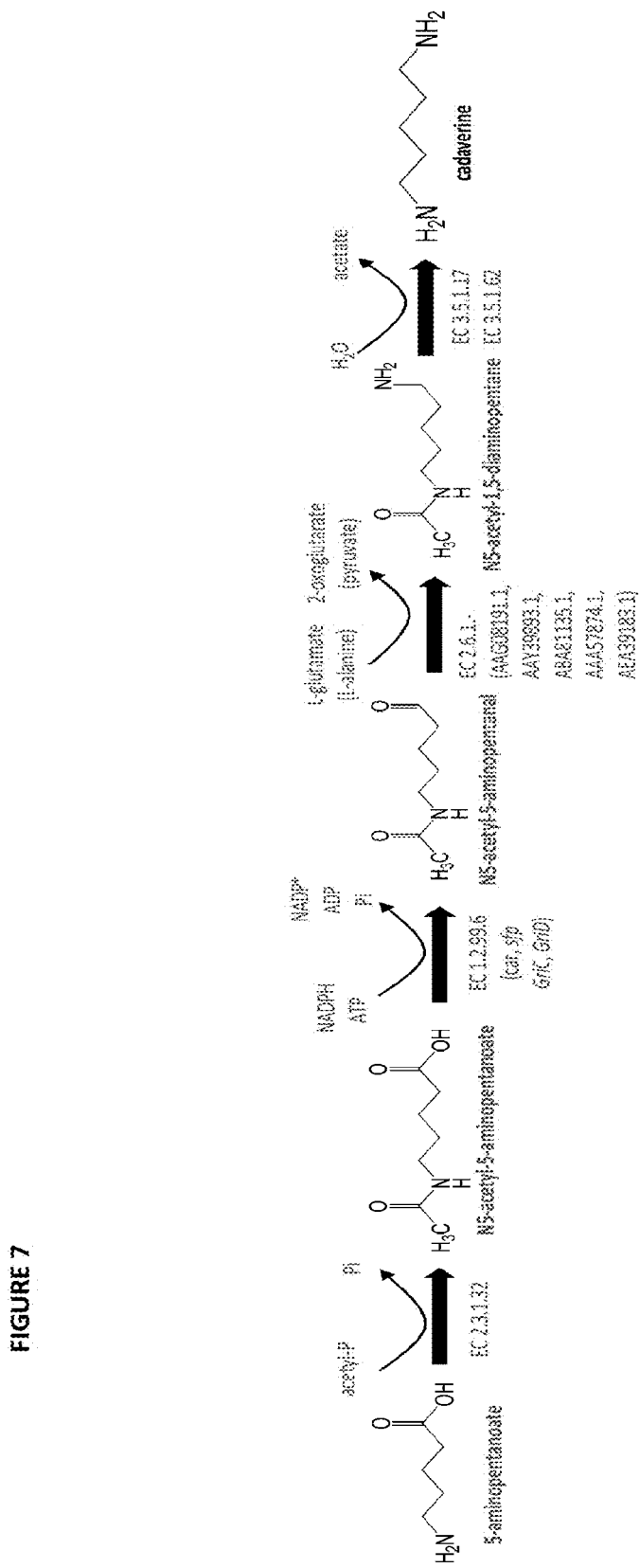
FIG. 7 is a schematic of an exemplary biochemical pathway leading to cadaverine using 5-aminopentanoate as a central precursor.

For example, a ω-transaminase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Chromobacterium violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), a *Rhodobacter sphaeroides* (see Genbank Accession No. ABA81135.1, SEQ ID NO: 11), an *Escherichia coli* (see Genbank Accession No. AAA57874.1, SEQ ID NO: 12), or a *Vibrio fluvialis* (see Genbank Accession No. AEA39183.1, SEQ ID NO: 13) ω-transaminase. Some of these ω-transaminases are diamine ω-transaminases. See, FIG. 5-7.

For example, a phosphopantetheinyl transferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Bacillus subtilis* phosphopantetheinyl transferase (see Genbank Accession No. CAA44858.1, SEQ ID NO: 14) or a *Nocardia* sp. NRRL 5646 phosphopantetheinyl transferase (see Genbank Accession No. ABI83656.1, SEQ ID NO: 15). See FIG. 4 and FIG. 9.

For example, a 2-oxoglutaryl-CoA dehydrogenase complex described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Azotobacter vinelandii* 2-oxoglutarate dehydrogenase complex (see Genbank Accession Nos. CAA36680.1 & CAA36678.1 & CAA36679.1, SEQ ID NO: 16). See FIG. 1.

For example, a thioesterase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Lactobacillus brevis* acyl-[acp] thioesterase (see Genbank Accession Nos. ABJ63754.1, SEQ ID NO: 17), a *Lactobacillus plantarum* acyl-[acp] thioesterase (see Genbank Accession Nos. CCC78182.1, SEQ ID NO: 18). See FIG. 2.

For example, an alpha-amino decarboxylase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* glutamate decarboxylase (see Genbank Accession No. AAA23833.1, SEQ ID: 19), an *Escherichia coli* lysine decarboxylase (see Genbank Accession No. AAA23536.1, SEQ ID: 20), an *Escherichia coli* ornithine decarboxylase (see Genbank Accession No. AAA62785.1, SEQ ID: 21), an *Escherichia coli* lysine decarboxylase (see Genbank Accession No. BAA21656.1, SEQ ID: 22). See FIG. 3.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences.

Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a reductase, deacetylase, N-acetyltransferase, synthase, hydratase, dehydrogenase, decarboxylase, or ω-transaminase as described herein.

In addition, the production of one or more C5 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Figure 2:
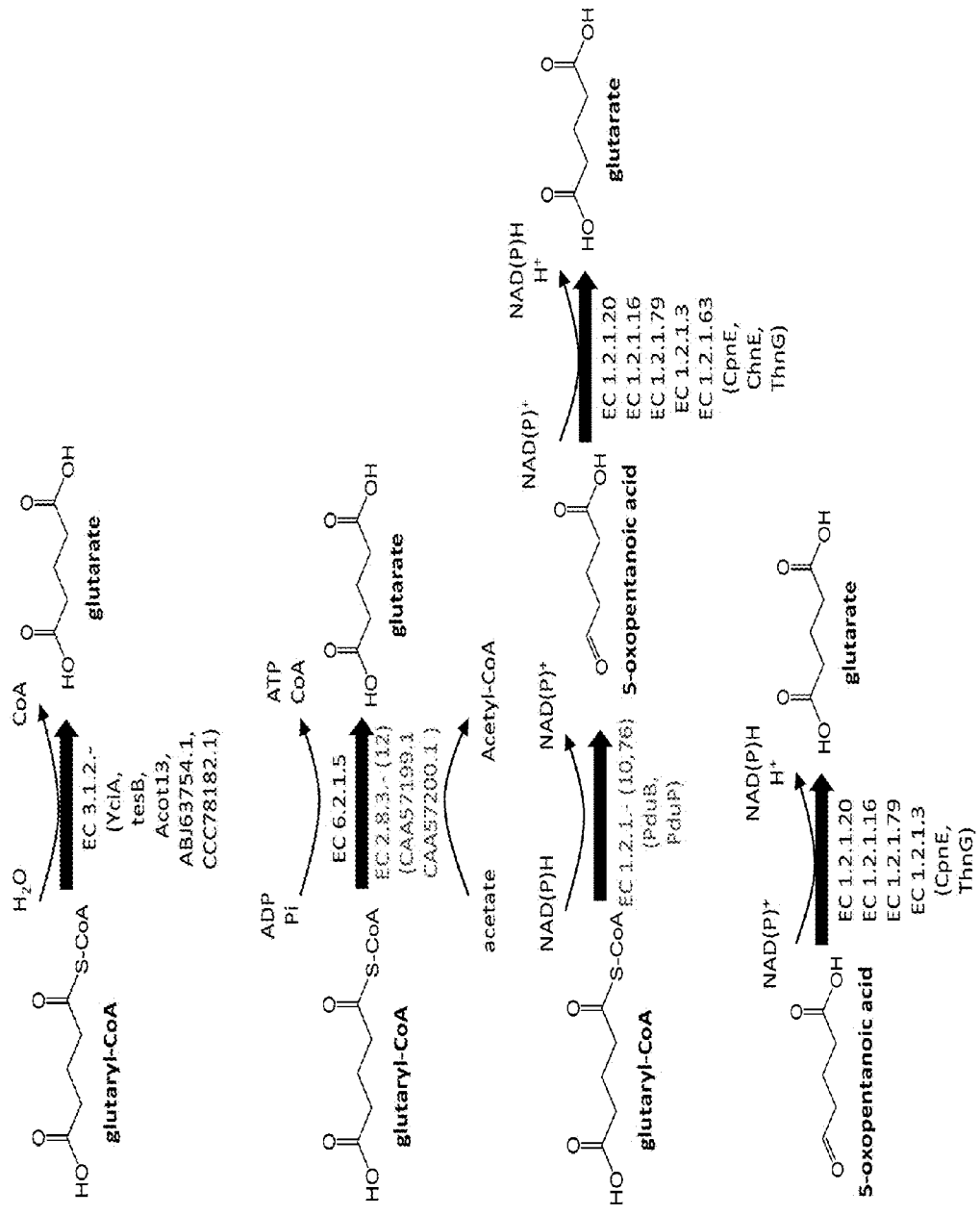
FIG. 2 is a schematic of exemplary biochemical pathways leading to glutarate from glutaryl-CoA or 5-oxopentanoic acid.

Enzymes Generating the Terminal Carboxyl Groups in the Biosynthesis of a C5 Building Block As depicted in FIG. 2, a terminal carboxyl group can be enzymatically formed using (i) a thioesterase, (ii) a reversible CoA-ligase, (iii) a CoA-transferase, or (iv) an acylating dehydrogenase, and (v) an aldehyde dehydrogenase such as a 7-oxoheptanoate dehydrogenase, a 6-oxohexanoate dehydrogenase, or a 5-oxopentanoate dehydrogenase.

In some embodiments, a terminal carboxyl group leading to the synthesis of glutarate is enzymatically formed by a thioesterase classified under EC 3.1.2.-, such as the gene product of YciA, tesB (Genbank Accession No. AAA24665.1) or Acot13 (see, for example, Cantu et al., *Protein Science*, 2010, 19, 1281-1295; Zhuang et al., *Biochemistry*, 2008, 47(9), 2789-2796; or Naggert et al., *J. Biol. Chem.*, 1991, 266(17), 11044-11050).

In some embodiments, the second terminal carboxyl group leading to the synthesis of glutaric acid is enzymatically formed by a CoA-transferase such as a glutaconate CoA-transferase classified, for example, under EC 2.8.3.12 such as from *Acidaminococcus fermentans*. See, for example, Buckel et al., 1981, *Eur. J. Biochem.*, 118:315-321. See, e.g., FIG. 2.

In some embodiments, the second terminal carboxyl group leading to the synthesis of glutaric acid is enzymatically formed by a reversible CoA-ligase such as a succinate-CoA ligase classified, for example, under EC 6.2.1.5 such as from *Thermococcus kodakaraensis*. See, for example, Shikata et al., 2007, *J. Biol. Chem.*, 282(37):26963-26970. See, e.g., FIG. 2.

In some embodiments, the second terminal carboxyl group leading to the synthesis of glutaric acid is enzymatically formed by an acyl-[acp] thioesterase classified under EC 3.1.2.-, such as the acyl-[acp] thioesterase from *Lactobacillus brevis* (GenBank Accession No. ABJ63754.1, SEQ ID NO: 17) or from *Lactobacillus plantarum* (GenBank Accession No. CCC78182.1, SEQ ID NO: 18). Such acyl-[acp] thioesterases have C6-C8 chain length specificity (see, for example, Jing et al., 2011, *BMC Biochemistry*, 12(44)). See, e.g., FIG. 2.

In some embodiments, the second terminal carboxyl group leading to the synthesis of glutaric acid is enzymatically formed by an aldehyde dehydrogenase classified, for example, under EC 1.2.1.3 (see, Guerrillot & Vandecasteele, *Eur. J. Biochem.*, 1977, 81, 185-192). See, e.g., FIG. 2.

Figure 4:
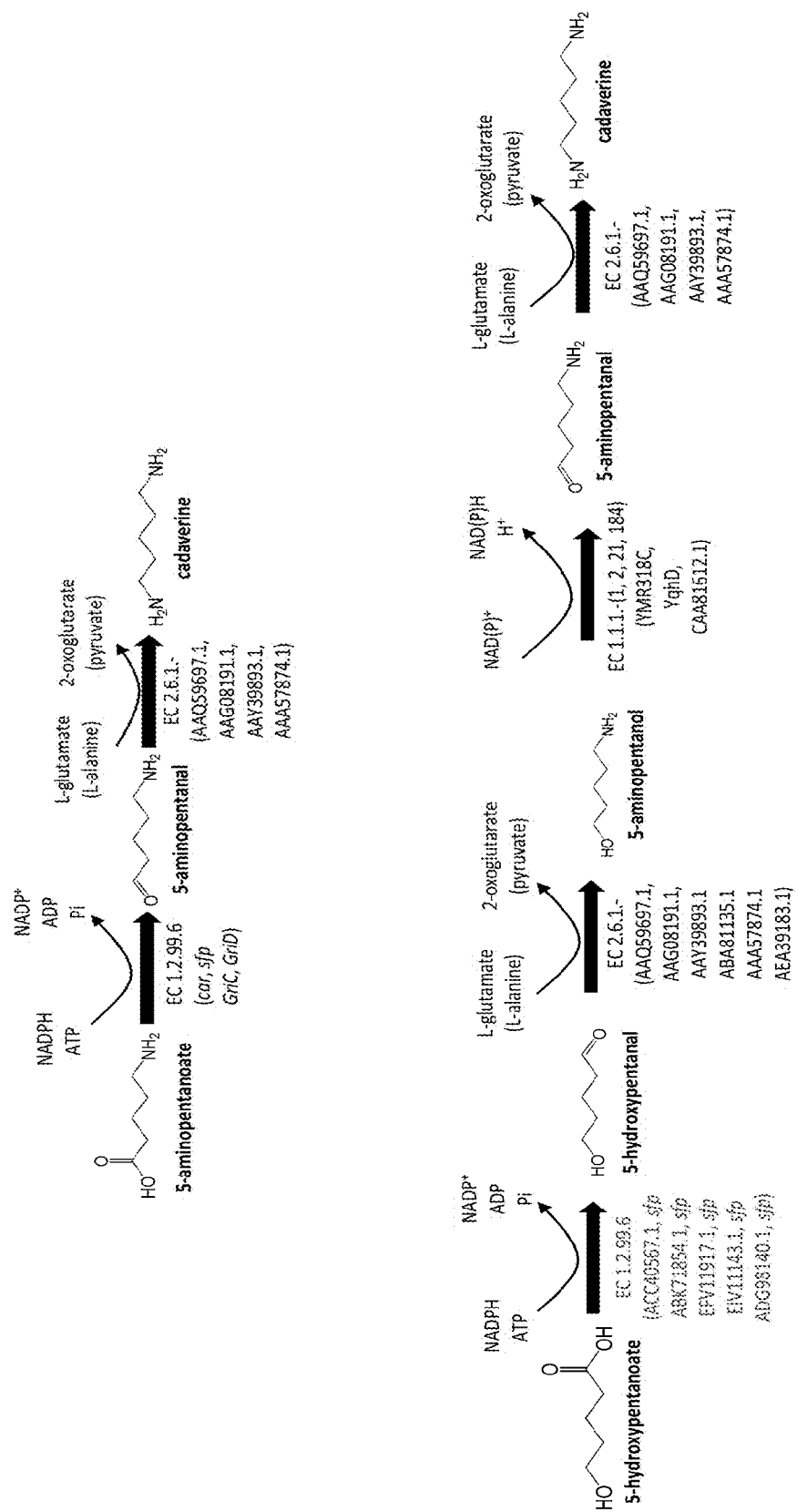
FIG. 4 is a schematic of exemplary biochemical pathways leading to cadaverine using 5-aminopentanoate (also known as 5-aminovalerate) or 5-hydroxypentanoate.
Figure 5:
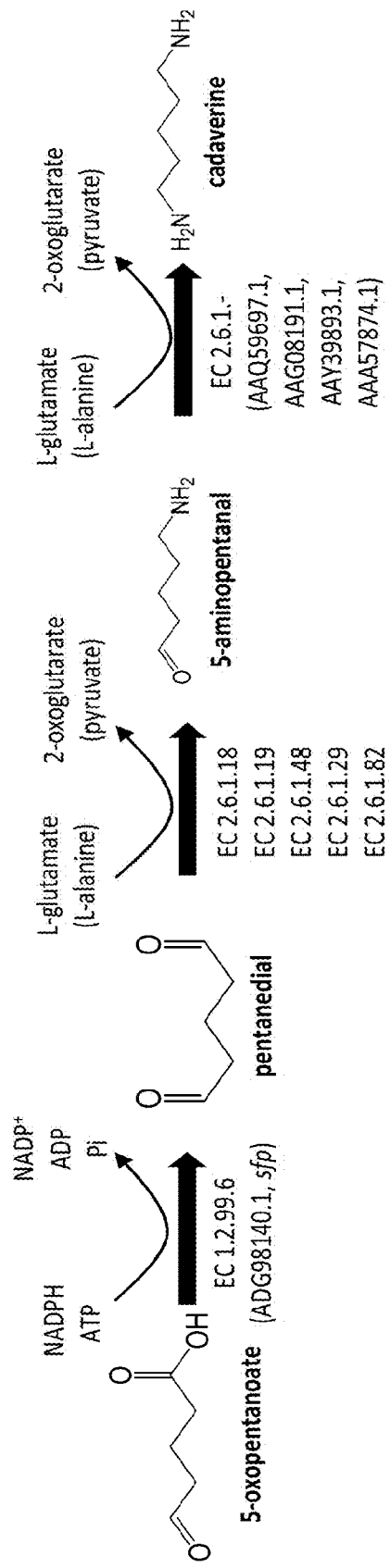
FIG. 5 is a schematic of an exemplary biochemical pathway leading to cadaverine using glutarate semialdehyde (also known as 5-oxopentanoate) as a central precursor.

In some embodiments, the second terminal carboxyl group leading to the synthesis of glutaric acid is enzymatically formed by an aldehyde dehydrogenase classified under EC 1.2.1.- such as a glutarate semialdehyde dehydrogenase classified, for example, under EC 1.2.1.20, a succinate-semialdehyde dehydrogenase classified, for example, under EC 1.2.1.16 or EC 1.2.1.79, or an aldehyde dehydrogenase classified under EC 1.2.1.3. For example, an aldehyde dehydrogenase classified under EC 1.2.1.- can be a 5-oxopentanoate dehydrogenase such as the gene product of CpnE, a 6-oxohexanoate dehydrogenase (e.g., the gene product of ChnE from *Acinetobacter sp.*), or a 7-oxoheptanoate dehydrogenase (e.g., the gene product of ThnG from *Sphingomonas macrogolitabida*) (Iwaki et al., *Appl. Environ. Microbiol.*, 1999, 65(11), 5158-5162; Lopez-Sanchez et al., *Appl. Environ. Microbiol.*, 2010, 76(1), 110-118). For example, a 6-oxohexanoate dehydrogenase can be classified under EC 1.2.1.63 such as the gene product of ChnE. For example, a 7-oxoheptanoate dehydrogenase can be classified under EC 1.2.1.-. See, e.g., Enzymes Generating the Terminal Amine Groups in the Biosynthesis of a C5 Building Block As depicted in FIG. 4 and FIG. 5, terminal amine groups can be enzymatically formed using an alpha-amino decarboxylase, ω-transaminase or a deacetylase.

In some embodiments, the first terminal carboxyl group is formed by an alpha-amino decarboxylase classified, for example, under EC 4.1.1.- such as EC 4.1.1.15, EC 4.1.1.17, EC 4.1.1.18 or EC 4.1.1.19.

In some embodiments, the first terminal carboxyl group is formed by a 5-aminovalerate transaminase classified, for example, under EC 2.6.1.48, such as obtained from *Clostridium viride*. The reversible 5-aminovalerate transaminase from *Clostridium viride* has demonstrated analogous activity for the conversion of 6-aminohexanoate to adipate semialdehyde (Barker et al., *J. Biol. Chem.*, 1987, 262(19), 8994-9003).

In some embodiments, one terminal amine group leading to the synthesis of 5-aminopentanol or 5-aminopentanal can be enzymatically formed by a ω-transaminase classified, for example, under EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 8), *Pseudomonas aeruginosa* (Genbank Accession No. AAG08191.1, SEQ ID NO: 9), *Pseudomonas syringae* (Genbank Accession No. AAY39893.1, SEQ ID NO: 10), *Rhodobacter sphaeroides* (Genbank Accession No. ABA81135.1, SEQ ID NO: 11), *Escherichia coli* (Genbank Accession No. AEA39183.1, SEQ ID NO: 13), *Vibrio fluvialis* (Genbank Accession No. AAA57874.1, SEQ ID NO: 12), or *Streptomyces griseus*. Some of the ω-transaminases classified, for example, under EC 2.6.1.29 or EC 2.6.1.82 are diamine ω-transaminases (e.g., SEQ ID NO: 11). See, FIG. 4.

The reversible ω-transaminase from *Chromobacterium violaceum* (Genbank Accession No. AAQ59697.1, SEQ ID NO: 8) has demonstrated analogous activity accepting 6-aminohexanoic acid as amino donor, forming the first terminal amine group in adipate semialdehyde (Kaulmann et al., *Enzyme and Microbial Technology*, 2007, 41, 628-637).

The reversible 4-aminobubyrate: 2-oxoglutarate transaminase from *Streptomyces griseus* has demonstrated analogous activity for the conversion of 6-aminohexanoate to adipate semialdehyde (Yonaha et al., *Eur. J. Biochem.*, 1985, 146, 101-106).

In some embodiments, the second terminal amine group leading to the synthesis of cadaverine is enzymatically formed by a diamine transaminase. For example, the second terminal amino group can be enzymatically formed by a diamine transaminase classified, for example, under EC 2.6.1.29 or classified, for example, under EC 2.6.1.82, such as the gene product of YgjG from *E. coli* (Genbank Accession No. AAA57874.1, SEQ ID NO: 12).

The gene product of ygjG accepts a broad range of diamine carbon chain length substrates, such as putrescine, cadaverine and spermidine (Samsonova et al., *BMC Microbiology*, 2003, 3:2).

The diamine transaminase from *E. coli* strain B has demonstrated activity for 1,5 diaminopentane (Kim, *The Journal of Chemistry*, 1964, 239(3), 783-786).

In some embodiments, the second terminal amine group leading to the synthesis of hexamethylenediamine is enzymatically formed by a deacetylase such as an acyl-lysine deacylase classified, for example, under EC 3.5.1.17 or such as acetylputrescine deacetylase classified, for example, under EC 3.5.1.62. The acetylputrescine deacetylase from *Micrococcus luteus* K-11 accepts a broad range of carbon chain length substrates, such as acetylputrescine, acetylcadaverine and $N^8$-acetylspermidine (see, for example, Suzuki et al., 1986, *BBA—General Subjects*, 882(1):140-142).

Figure 8:
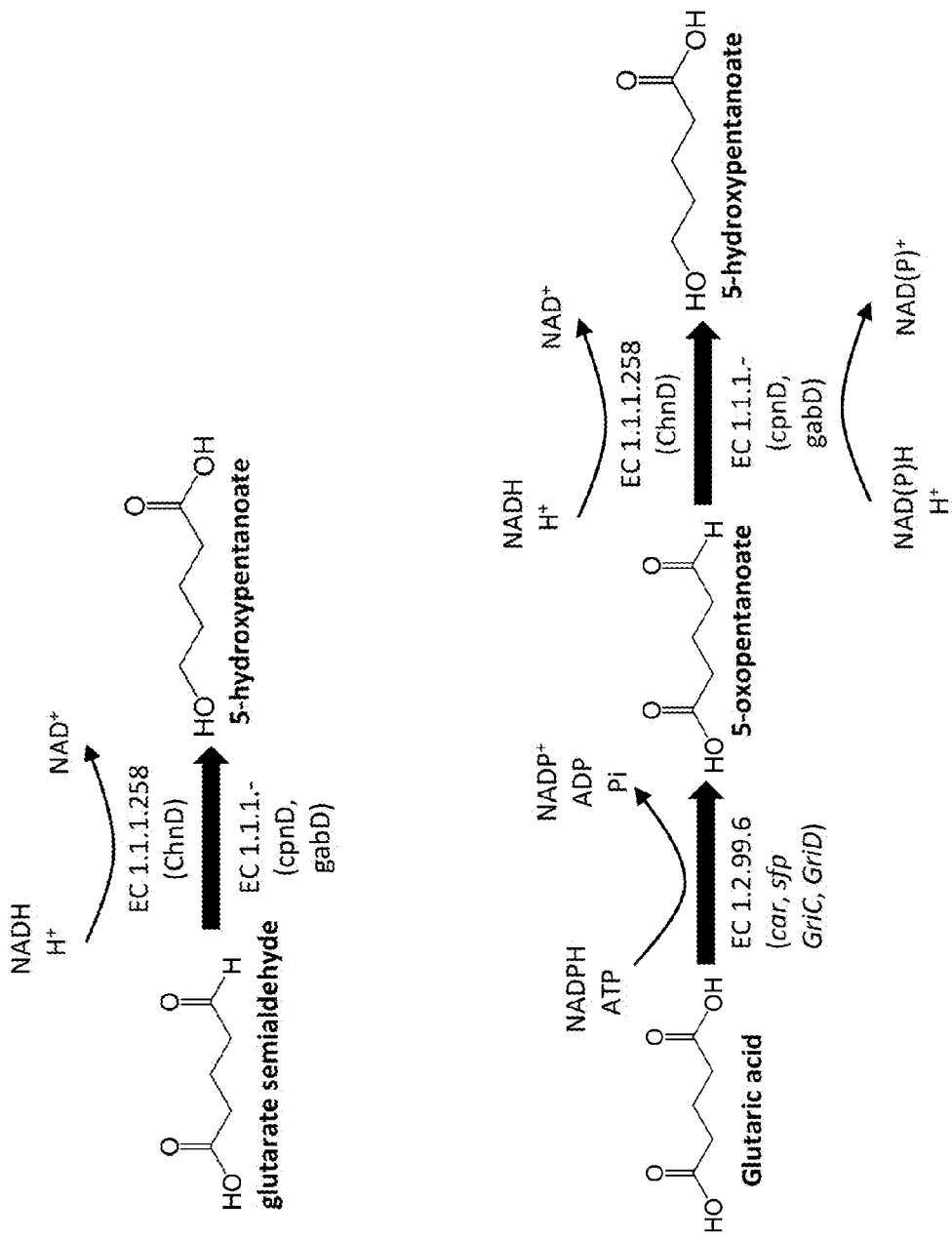
FIG. 8 is a schematic of exemplary biochemical pathways leading to 5-hydroxypentanoate using glutarate or glutarate semialdehyde (also known as 5-oxopentanoate) as a central precursor.
Figure 9:
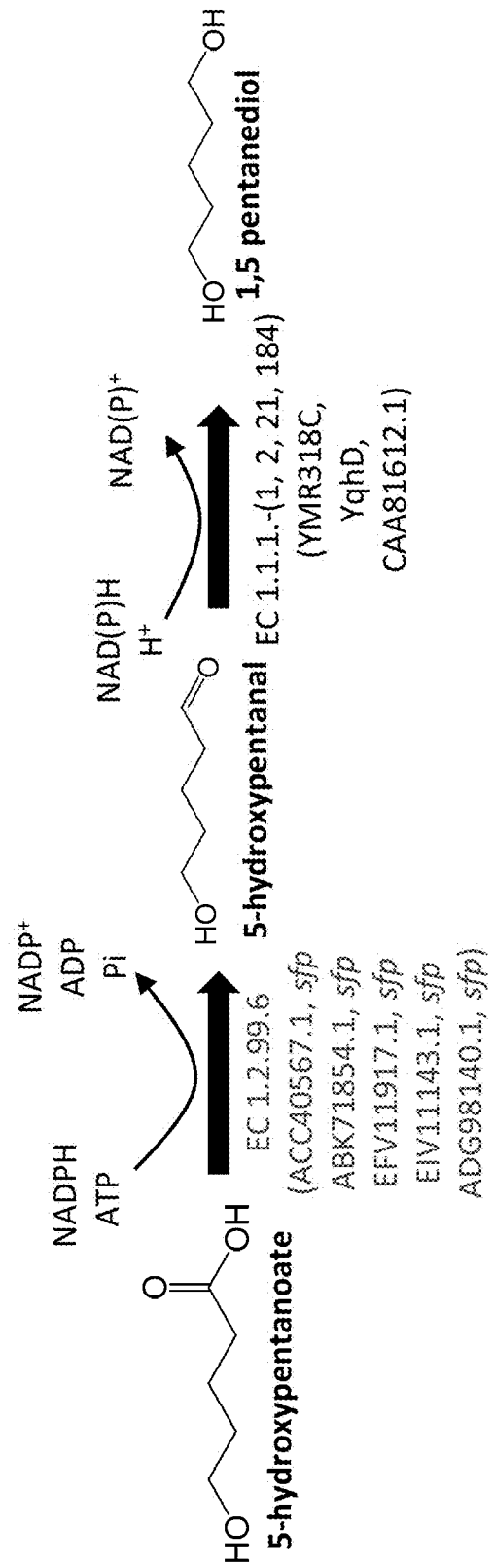
FIG. 9 is a schematic of an exemplary biochemical pathway leading to 1,5 pentanediol using 5-hydroxypentanoate as a central precursor.

Enzymes Generating the Terminal Hydroxyl Groups in the Biosynthesis of a C5 Building Block As depicted in FIGS. 8 and 9, a terminal hydroxyl group can be enzymatically formed using an alcohol dehydrogenase such as a 6-hydroxyhexanoate dehydrogenase, a 5-hydroxypentanoate dehydrogenase, or a 4-hydroxybutyrate dehydrogenase.

For example, a terminal hydroxyl group leading to the synthesis of 5-hydroxypentanoate can be enzymatically formed by a dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.- such as the gene product of CpnD (see, for example, Iwaki et al., 2002, *Appl. Environ. Microbiol.*, 68(11):5671-5684), a 5-hydroxypentanoate dehydrogenase from *Clostridium viride*, or a 4-hydroxybutyrate dehydrogenase such as gabD (see, for example, Lütke-Eversloh & Steinbüchel, 1999, *FEMS Microbiology Letters*, 181(1):63-71). See, FIG. 8.

A terminal hydroxyl group leading to the synthesis of 1,5 pentanediol can be enzymatically formed by an alcohol dehydrogenase classified under EC 1.1.1.- (e.g., EC 1.1.1.1, 1.1.1.2, 1.1.1.21, or 1.1.1.184). See FIG. 9.

Biochemical Pathways

Pathway to 2-Oxoadipate

As depicted in FIG. 1, 2-oxoglutarate can be converted to homocitrate by a 2-isopropylmalate synthase or homocitrate synthase classified, for example, under EC 2.3.3.14 or EC 2.3.3.13; followed by conversion of homocitrate to isohomocitrate by a homoaconitate hydratase or 3-isopropylmalate dehydratase classified, for example, under EC 4.2.1.114, EC 4.2.1.36 or EC 4.2.1.33; followed by conversion of isohomocitrate to 2-oxoadipate by a homoisocitrate dehydrogenase or a 3-isopropylmalate dehydrogenase classified, for example, under EC 1.1.1.85, EC 1.1.1.87 or EC 1.1.1.286.

Pathway to 5-Oxopentanoate, Glutaryl-CoA, or Glutarate Using 2-Oxoadipate as a Central Precursor As depicted in FIG. 1, 2-oxoadipate can be converted to 5-oxopentanoate (glutarate semialdehyde) by a 2-oxoacid decarboxylase classified, for example, under EC 4.1.1.71, EC 4.1.1.72, EC 4.1.1.43 or EC 4.1.1.74.

As depicted in FIG. 1 and FIG. 2, 2-oxoadipate can be converted to glutaryl-CoA by a 2-oxoglutarate dehydrogenase complex classified, for example, under EC 1.2.4.2, EC 1.8.1.4 and EC 2.3.1.61; followed by conversion to glutarate by a (i) a thioesterase classified, for example, EC 3.1.2.-, (ii) a reversible CoA-ligase classified, for example, under EC 6.2.1.5, (iii) a CoA-transferase classified, for example, under EC 2.8.3.- such as EC 2.8.3.12, or (iv) an acylating dehydrogenase classified under, for example, EC 1.2.1.10 or EC 1.2.1.76 and an aldehyde dehydrogenase classified under EC 1.2.1.- such as a glutarate semialdehyde dehydrogenase classified, for example, under EC 1.2.1.20, a succinate-semialdehyde dehydrogenase classified, for example, under EC 1.2.1.16 or EC 1.2.1.79, or an aldehyde dehydrogenase classified under EC 1.2.1.3. For example, a 5-oxovalerate dehydrogenase such as the gene product of CpnE, a 6-oxohexanoate dehydrogenase such as the gene product of ChnE, or a 7-oxoheptanoate dehydrogenase (e.g., the gene product of ThnG from *Sphingomonas macrogolitabida*) can be used to convert 5-oxopentanoic acid to glutarate.

As depicted in FIG. 1 and FIG. 2, 2-oxoadipate can be converted to glutaryl-CoA by a 2-oxoglutarate dehydrogenase complex classified, for example, under EC 1.2.4.2, EC 1.8.1.4 and EC 2.3.1.61; followed by conversion to 5-oxopentanoate by an acylating dehydrogenase classified under, for example, EC 1.2.1.10 or EC 1.2.1.76.

Figure 3:
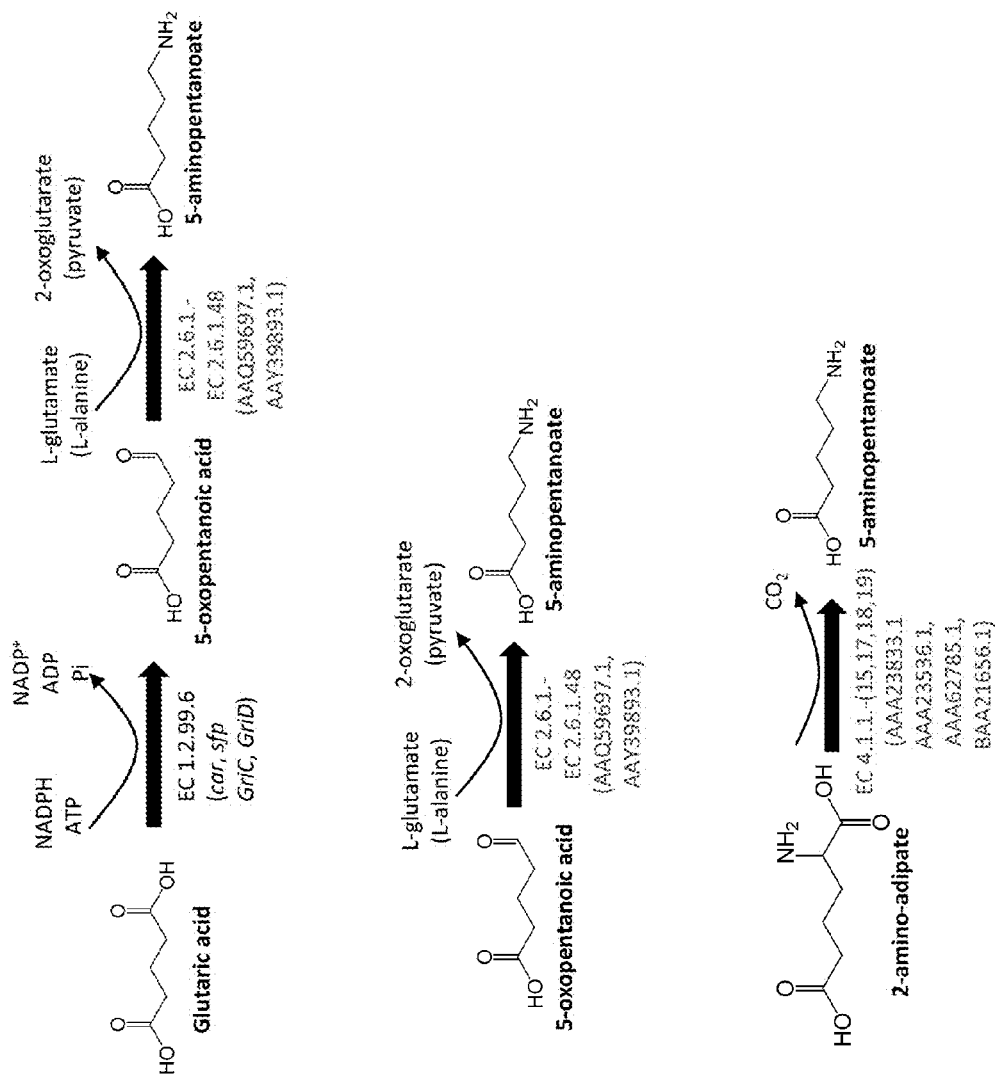
FIG. 3 is a schematic of exemplary biochemical pathways leading to 5-aminopentanoate using glutarate, 5-oxopentanoate or 2-aminoadipate as a central precursor.

Pathway to 5-Aminopentanoate Using 5-Oxopentanoate, Glutarate and 2-Aminoadipate as a Central Precursor As depicted in FIG. 3, glutarate can be converted to 5-aminopentanoate (5-aminovaleric acid) by a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus*; followed by conversion to 5-aminopentanoate by a ω-transaminase classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 8), a *Pseudomonas syringae* (see Genbank Accession No. AAY39893.1, SEQ ID NO: 10) or obtained from *Clostridium viride*.

As depicted in FIG. 3, 5-oxopentanoate can be converted to 5-aminopentanoate (5-aminovaleric acid) by a ω-transaminase classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 8), a *Pseudomonas syringae* (see Genbank Accession No. AAY39893.1, SEQ ID NO: 10) or obtained from *Clostridium viride*. As depicted in FIG. 1 and FIG. 3, 2-oxoadipate can be converted to 2-aminoadipate by an alpha-aminotransaminase classified, for example, under EC 2.6.1.- such as EC 2.6.1.7 or EC 2.6.1.39; followed by conversion to 5-aminopentanoate by an alpha-amino decarboxylase classified, for example, under EC 4.1.1.- such as EC 4.1.1.15, EC 4.1.1.17, EC 4.1.1.18, EC 4.1.1.19 such as from *Escherichia coli* (see Genbank Accession Nos. AAA23833.1, AAA23536.1, AAA62785.1 or BAA21656.1, SEQ ID NOs. 19-22).

Pathway to 5-Hydroxypentanoate Using 5-Oxopentanoate or Glutaric Acid as a Central Precursor As depicted in FIG. 8, 5-oxopentanoate can be converted to 5-hydroxypentanoate by a dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.- such as the gene product of CpnD (see, for example, Iwaki et al., 2002, *Appl. Environ. Microbiol.*, 68(11):5671-5684), a 5-hydroxypentanoate dehydrogenase from *Clostridium viride*, or a 4-hydroxybutyrate dehydrogenase such as gabD (see, for example, Lütke-Eversloh & Steinbüchel, 1999, *FEMS Microbiology Letters*, 181(1):63-71).

As depicted in FIG. 8, glutaric acid can be converted to 5-hydroxypentanoate by a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus*; followed by conversion to 5-hydroxypentanoate dehydrogenase by an alcohol dehydrogenase classified, for example, under EC 1.1.1.- such as a 6-hydroxyhexanoate dehydrogenase classified, for example, under EC 1.1.1.258 (e.g., the gene from of ChnD), a 5-hydroxypentanoate dehydrogenase classified, for example, under EC 1.1.1.- such as the gene product of CpnD (see, for example, Iwaki et al., 2002, *Appl. Environ. Microbiol.*, 68(11):5671-5684), a 5-hydroxypentanoate dehydrogenase from *Clostridium viride*, or a 4-hydroxybutyrate dehydrogenase such as gabD (see, for example, Lütke-Eversloh & Steinbüchel, 1999, *FEMS Microbiology Letters*, 181(1):63-71).

Pathway Using 5-Aminopentanoate, 5-Hydroxypentanoate, or Glutarate Semialdehyde as Central Precursor to Cadaverine As depicted in FIG. 4, cadaverine is synthesized from the central precursor 5-aminopentanoate by conversion of 5-aminopentanoate to 5-aminopentanal by a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus*; followed by conversion of 5-aminopentanal to cadaverine by a ω-transaminase classified, for example, under EC 2.6.1.- such as 2.6.1.18, EC 2.6.1.19, EC 2.6.1.29, EC 2.6.1.48, or EC 2.6.1.82 such as from a Chromobacterium *violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO:

10), or an *Escherichia coli* (see Genbank Accession No. AAA57874.1, SEQ ID NO: 12).

The carboxylate reductase encoded by the gene product of car and enhancer npt or sfp has broad substrate specificity, including terminal difunctional C4 and C5 carboxylic acids (Venkitasubramanian et al., *Enzyme and Microbial Technology*, 2008, 42, 130-137).

In some embodiments, cadaverine is synthesized from the central precursor 5-hydroxypentanoate (which can be produced as described in FIG. 8), by conversion of 5-hydroxypentanoate to 5-hydroxypentanal by a carboxylate reductase classified, for example, under EC 1.2.99.6 such as from a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7), in combination with a phosphopantetheine transferase enhancer (e.g., encoded by a sfp (Genbank Accession No. CAA44858.1, SEQ ID NO: 21) gene from *Bacillus subtilis* or npt (Genbank Accession No. ABI83656.1, SEQ ID NO: 22) gene from *Nocardia*), or the gene product of GriC & GriD (Suzuki et al., *J. Antibiot.*, 2007, 60(6), 380-387); followed by conversion of 5-oxopentanol to 5-aminopentanol by a ω-transaminase classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), a *Rhodobacter sphaeroides* (see Genbank Accession No. ABA81135.1, SEQ ID NO: 11), an *Escherichia coli* (see Genbank Accession No. AAA57874.1, SEQ ID NO: 12), or a *Vibrio fluvialis* (see Genbank Accession No. AEA39183.1, SEQ ID NO: 13); followed by conversion to 5-aminopentanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to cadaverine by a ω-transaminase classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), or an *Escherichia coli* (see Genbank Accession No. AAA57874.1, SEQ ID NO: 12). See FIG. 4.

In some embodiments, cadaverine is synthesized from the central precursor 5-aminopentanoate by conversion of 5-aminopentanoate to N5-acetyl-5-aminopentanoate by an N-acetyltransferase such as a lysine N-acetyltransferase classified, for example, under EC 2.3.1.32; followed by conversion to N5-acetyl-5-aminopentanal by a carboxylate reductase such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus*; followed by conversion to N5-acetyl-1,5-diaminopentane by a ω-transaminase classified, for example, under EC 2.6.1.- such as 2.6.1.18, EC 2.6.1.19, EC 2.6.1.29, EC 2.6.1.48, or EC 2.6.1.82 such as from a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), a *Rhodobacter sphaeroides* (see Genbank Accession No. ABA81135.1, SEQ ID NO: 11), an *Escherichia coli* (see Genbank Accession No. AAA57874.1, SEQ ID NO: 12), or a *Vibrio fluvialis* (see Genbank Accession No. AEA39183.1, SEQ ID NO: 13); followed by conversion to cadaverine by an acetylputrescine deacetylase classified, for example, under EC 3.5.1.17 or EC 3.5.1.62. See, FIG. 7.

In some embodiments, cadaverine is synthesized from the central precursor glutarate semialdehyde by conversion of glutarate semialdehyde to pentanedial by a carboxylate reductase classified, for example, under EC 1.2.99.6 such as from a *Segniliparus rotundus* (see Genbank Accession No. ADG98140.1, SEQ ID NO: 7), in combination with a phosphopantetheine transferase enhancer (e.g., encoded by a sfp (Genbank Accession No. CAA44858.1, SEQ ID NO:21) gene from *Bacillus subtilis* or npt (Genbank Accession No. ABI83656.1, SEQ ID NO:22) gene from *Nocardia*), or the gene product of GriC & GriD (Suzuki et al., *J. Antibiot.*, 2007, 60(6), 380-387); followed by conversion to 5-aminopentanal by a ω-transaminase classified, for example, under EC 2.6.1.- such as 2.6.1.18, EC 2.6.1.19, EC 2.6.1.29, EC 2.6.1.48, or EC 2.6.1.82; followed by conversion to cadaverine by a ω-transaminase classified, for example, under EC 2.6.1.- such as 2.6.1.18, EC 2.6.1.19, EC 2.6.1.29, EC 2.6.1.48, or EC 2.6.1.82 such as from a Chromobacterium *violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), or an *Escherichia coli* (see Genbank Accession No. AAA57874.1, SEQ ID NO: 12). See FIG. 5.

In some embodiments, cadaverine is synthesized from the central precursor 1,5-pentanediol by conversion of 1,5-pentanediol to 5-hydroxypentanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion of 5-oxopentanal to 5-aminopentanol by a ω-transaminase classified, for example, under EC 2.6.1.- such as 2.6.1.18, EC 2.6.1.19, EC 2.6.1.29, EC 2.6.1.48, or EC 2.6.1.82 such as from a Chromobacterium *violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), a *Rhodobacter sphaeroides* (see Genbank Accession No. ABA81135.1, SEQ ID NO: 11), an *Escherichia coli* (see Genbank Accession No. AAA57874.1, SEQ ID NO: 12), or a *Vibrio fluvialis* (see Genbank Accession No. AEA39183.1, SEQ ID NO: 13); followed by conversion to 5-aminopentanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to cadaverine by a ω-transaminase classified, for example, under EC 2.6.1.- such as 2.6.1.18, EC 2.6.1.19, EC 2.6.1.29, EC 2.6.1.48, or EC 2.6.1.82 such as from a *Chromobacterium violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), or an *Escherichia coli* (see Genbank Accession No. AAA57874.1, SEQ ID NO: 12). See FIG. 6.

Pathways Using 5-Hydroxypentanoate as Central Precursor to 1,5-Pentanediol

As depicted in FIG. 9, 1,5 pentanediol is synthesized from the central precursor 5-hydroxypentanoate by conversion of 5-hydroxypentanoate to 5-hydroxypentanal by a carboxylate reductase classified, for example, under EC 1.2.99.6 such as from a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7), in combination with a phosphopantetheine transferase enhancer (e.g., encoded by a sfp (Genbank Accession No. CAA44858.1, SEQ ID NO:21) gene from *Bacillus subtilis* or npt (Genbank Accession No. ABI83656.1, SEQ ID NO: 22) gene from *Nocardia*), or the gene product of GriC & GriD (Suzuki et al., *J. Antibiot.*, 2007, 60(6), 380-387); followed by conversion of 5-hydroxypentanal to 1,5 pentanediol by an alcohol dehydrogenase classified, for example, under EC 1.1.1.- such as EC 1.1.1.1, EC 1.1.1.2, EC 1.1.1.21, or EC 1.1.1.184) such as the gene product of YMR318C (Genbank Accession No. CAA90836.1) or YqhD (from *E. coli*, GenBank Accession No. AAA69178.1) (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*). See, FIG. 9.

Cultivation Strategy

In some embodiments, the cultivation strategy entails achieving an aerobic, anaerobic, micro-aerobic, or mixed oxygen/denitrification cultivation condition. Enzymes characterized in vitro as being oxygen sensitive require a microaerobic cultivation strategy maintaining a very low dissolved oxygen concentration (See, for example, Chayabatra & Lu-Kwang, *Appl. Environ. Microbiol.*, 2000, 66(2), 493 0 498; Wilson and Bouwer, 1997, *Journal of Industrial Microbiology and Biotechnology*, 18(2-3), 116-130).

In some embodiments, a cyclical cultivation strategy entails alternating between achieving an anaerobic cultivation condition and achieving an aerobic cultivation condition.

In some embodiments, the cultivation strategy entails nutrient limitation such as nitrogen, phosphate or oxygen limitation.

In some embodiments, a final electron acceptor other than oxygen such as nitrates can be utilized. In some embodiments, a cell retention strategy using, for example, ceramic membranes can be employed to achieve and maintain a high cell density during either fed-batch or continuous fermentation.

In some embodiments, the principal carbon source fed to the fermentation in the synthesis of one or more C5 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli*, *Cupriavidus necator*, *Pseudomonas oleavorans*, *Pseudomonas putida* and *Yarrowia lipolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida*, *Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli*, *Corynebacterium glutamicum* and *Lactobacillus delbrueckii* and *Lactococcus lactis* (see, e.g., Hermann et al, *J. Biotechnol.*, 2003, 104: 155-172; Wee et al., *Food Technol. Biotechnol.*, 2006, 44(2):163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15):5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C5 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issatchenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C5 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C5 building block.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to a C5 building block.

In some embodiments, the host microorganism's tolerance to high concentrations of a C5 building block can be improved through continuous cultivation in a selective environment.

In some embodiments, the host microorganism's endogenous biochemical network can be attenuated or augmented to (1) ensure the intracellular availability of 2-oxoglutarate, (2) create a NADPH imbalance that may be balanced via the formation of one or more C5 building blocks, (3) prevent degradation of central metabolites, central precursors leading to and including one or more C5 building blocks and/or (4) ensure efficient efflux from the cell.

In some embodiments requiring the intracellular availability of L-glutamate for C5 building block synthesis, the enzymes catalyzing anaplerotic reactions supplementing the citric acid cycle intermediates are amplified.

In some embodiments requiring the intracellular availability of 2-oxoglutarate, a PEP carboxykinase or PEP carboxylase can be overexpressed in the host to generate anaplerotic carbon flux into the Krebs cycle towards 2-oxoglutarate (Schwartz et al., 2009, *Proteomics*, 9, 5132-5142).

In some embodiments requiring the intracellular availability of 2-oxo-glutarate, a pyruvate carboxylase can be overexpressed in the host to generated anaplerotic carbon flux into the Krebs cycle towards 2-oxoglutarate (Schwartz et al., 2009, *Proteomics*, 9, 5132-5142).

In some embodiments requiring the intracellular availability of 2-oxo-glutarate, a PEP synthase can be overexpressed in the host to enhance the flux from pyruvate to PEP, thus increasing the carbon flux into the Krebs cycle via PEP carboxykinase or PEP carboxylase (Schwartz et al., 2009, *Proteomics*, 9, 5132-5142).

In some embodiments requiring the intracellular availability of 2-oxo-glutarate for C5 building block synthesis, anaplerotic reactions enzymes such as phosphoenolpyruvate carboxylase (e.g., the gene product of pck), phosphoenolpyruvate carboxykinase (e.g., the gene product of ppc), the malic enzyme (e.g., the gene product of sfcA) and/or pyruvate carboxylase are overexpressed in the host organisms (Song and Lee, 2006, *Enzyme Micr. Technol.*, 39, 352-361).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of a C5 building block, a gene such as UdhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of a C5 Building Block, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of a C5 building block, a recombinant malic enzyme gene such as maeA or maeB can be overexpressed in the host organisms (Brigham et al., 2012, supra).

In some embodiments, where pathways require excess NADPH co-factor in the synthesis of a C5 building block, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C5 building block, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C5 building block, endogenous triose phosphate isomerase (EC 5.3.1.1) can be attenuated.

In some embodiments, where pathways require excess NADPH co-factor in the synthesis of a C5 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments using hosts that naturally accumulate polyhydroxyalkanoates, the endogenous polyhydroxyalkanoate synthase enzymes can be attenuated in the host strain.

In some embodiments, a L-alanine dehydrogenase can be overexpressed in the host to regenerate L-alanine from pyruvate as an amino donor for ω-transaminase reactions.

In some embodiments, a L-glutamate dehydrogenase, a L-glutamine synthetase, or a glutamate synthase can be overexpressed in the host to regenerate L-glutamate from 2-oxoglutarate as an amino donor for ω-transaminase reactions.

In some embodiments, enzymes such as; an acyl-CoA dehydrogenase classified, for example, under EC 1.3.8.7 or EC 1.3.8.1; and/or a glutaryl-CoA dehydrogenase classified, for example, under EC 1.3.8.6 or EC 1.3.99.7 that degrade central metabolites and central precursors leading to and including C5 building blocks can be attenuated.

In some embodiments, endogenous enzymes activating C5 building blocks via Coenzyme A esterification such as CoA-ligases (e.g., a glutaryl-CoA synthetase) classified under, for example, EC 6.2.1.6 can be attenuated.

In some embodiments, the efflux of a C5 building block across the cell membrane to the extracellular media can be enhanced or amplified by genetically engineering structural modifications to the cell membrane or increasing any associated transporter activity for a C5 building block.

The efflux of cadaverine can be enhanced or amplified by overexpressing broad substrate range multidrug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother*, 38(6), 1345-1355), or Bmr from *Bacillus subtilis* (Neyfakh, 1992, *Antimicrob Agents Chemother*, 36(2), 484-485).

The efflux of 5-aminopentanoate and cadaverine can be enhanced or amplified by overexpressing the solute transporters such as the lysE transporter from *Corynebacterium glutamicum* (Bellmann et al., 2001, *Microbiology*, 147, 1765-1774).

The efflux of glutaric acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C5 Building Blocks Using a Recombinant Host

Typically, one or more C5 building blocks can be produced by providing a host microorganism and culturing the provided microorganism with a culture medium containing a suitable carbon source as described above. In general, the culture media and/or culture conditions can be such that the microorganisms grow to an adequate density and produce a C5 building block efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C5 building block. Once produced, any method can be used to isolate C5 building blocks. For example, C5 building blocks can be recovered selectively from the fermentation broth via adsorption processes. In the case of glutaric acid and 5-aminopentanoic acid, the resulting eluate can be further concentrated via evaporation, crystallized via evaporative and/or cooling crystallization, and the crystals recovered via centrifugation. In the case of cadaverine and 1,5-pentanediol, distillation may be employed to achieve the desired product purity. The invention is further described in the following examples, which do not limit the scope of the invention described in the claims.

EXAMPLES

Example 1

Enzyme Activity of ω-Transaminase Using Glutarate Semialdehyde as Substrate and Forming 5-Aminopentanoate A nucleotide sequence encoding an N-terminal His-tag was added to the genes from Chromobacterium violaceum and Rhodobacter sphaeroides encoding the ω-transaminases of SEQ ID NOs: 8 and 10 respectively (see FIG. 10) such that N-terminal HIS tagged ω-transaminases could be produced. Each of the resulting modified genes was cloned into a pET21a expression vector under control of the T7 promoter and each expression vector was transformed into a BL21[DE3] E. coli host. The resulting recombinant E. coli strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 5-aminopentanoate to glutarate semialdehyde) were performed in a buffer composed of a final concentration of 50 mM HEPES buffer (pH=7.5), 10 mM 5-aminopentanoate, 10 mM pyruvate and 100 µM pyridoxyl 5' phosphate. Each enzyme activity assay reaction was initiated by adding cell free extract of the ω-transaminase gene product or the empty vector control to the assay buffer containing the 5-aminopentanoate and incubated at 25° C. for 4 h, with shaking at 250 rpm. The formation of L-alanine from pyruvate was quantified via RP-HPLC.

Figure 17:
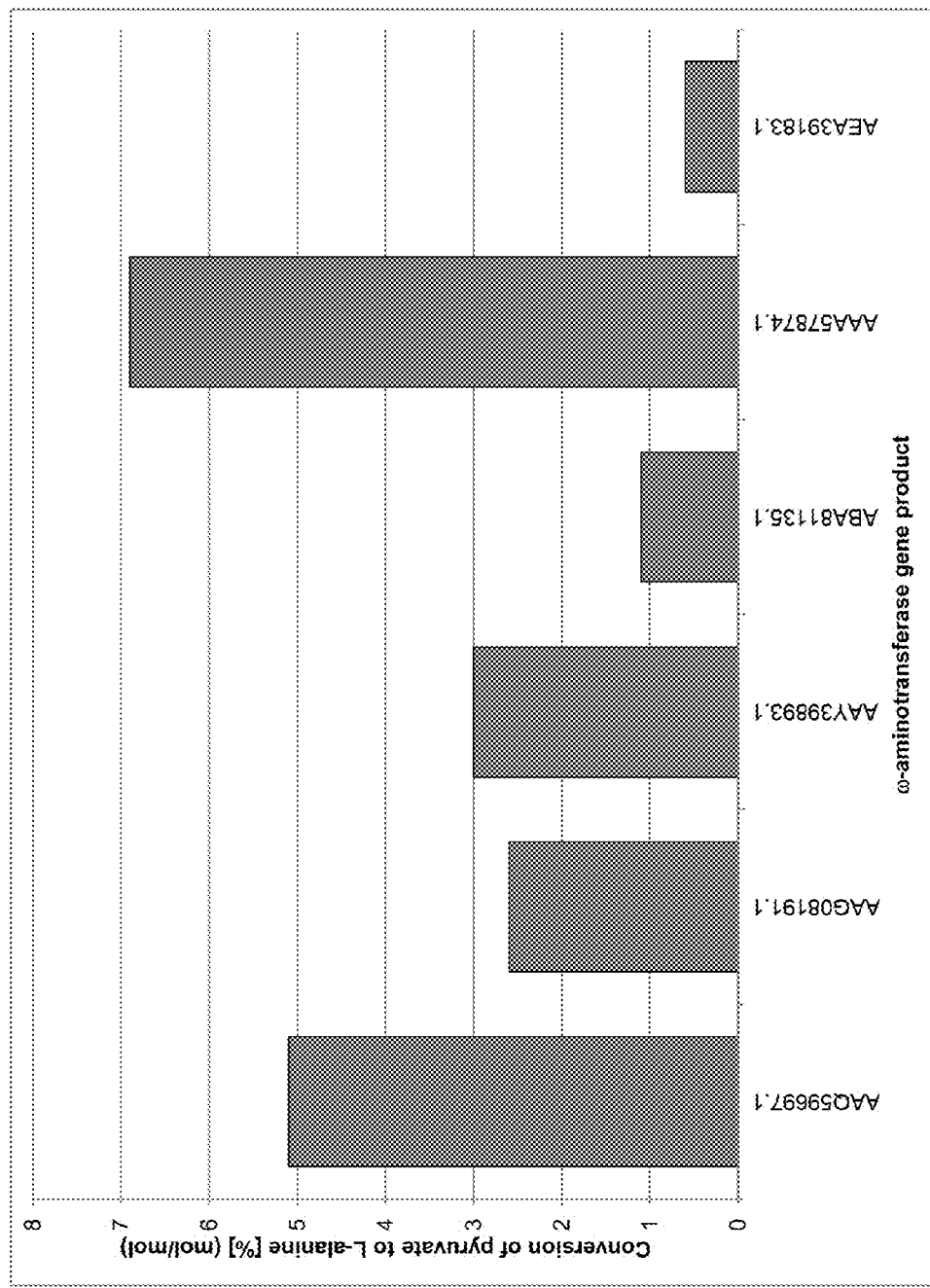
FIG. 17 is a bar graph summarizing the percent conversion of pyruvate to L-alanine (mol/mol) as a measure of the ω-transaminase activity of the enzyme only controls (no substrate).
Figure 18:
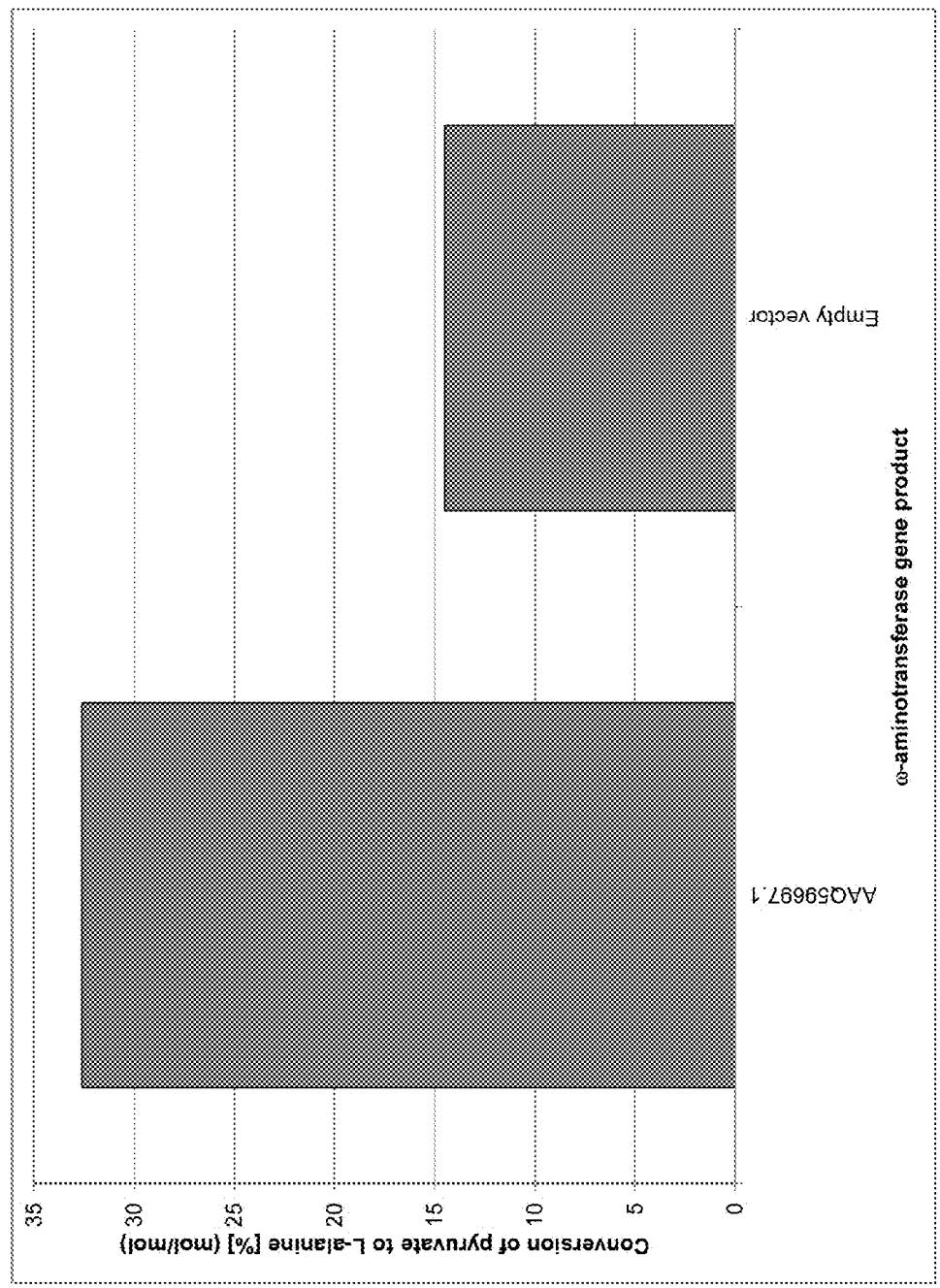
FIG. 18 is a bar graph showing the percent conversion after 4 hours of pyruvate to L-alanine (mol/mol) as a measure of the ω-transaminase activity of one ω-transaminase preparation for converting 5-aminopentanoate to glutarate semialdehyde relative to the empty vector control.

Each enzyme only control without 5-aminopentanoate demonstrated low base line conversion of pyruvate to L-alanine See FIG. 17. The gene product of SEQ ID NO 8, accepted 5-aminopentanote as substrate as confirmed against the empty vector control. See FIG. 18.

Enzyme activity in the forward direction (i.e., glutarate semialdehyde to 5-aminopentanoate) was confirmed for the transaminase of SEQ ID NO 10. Enzyme activity assays were performed in a buffer composed of a final concentration of 50 mM HEPES buffer (pH=7.5), 10 mM glutarate semialdehyde, 10 mM L-alanine and 100 µM pyridoxyl 5' phosphate. Each enzyme activity assay reaction was initiated by adding a cell free extract of the ω-transaminase gene product or the empty vector control to the assay buffer containing the glutarate semialdehyde and incubated at 25° C. for 4 h, with shaking at 250 rpm. The formation of pyruvate was quantified via RP-HPLC.

Figure 19:
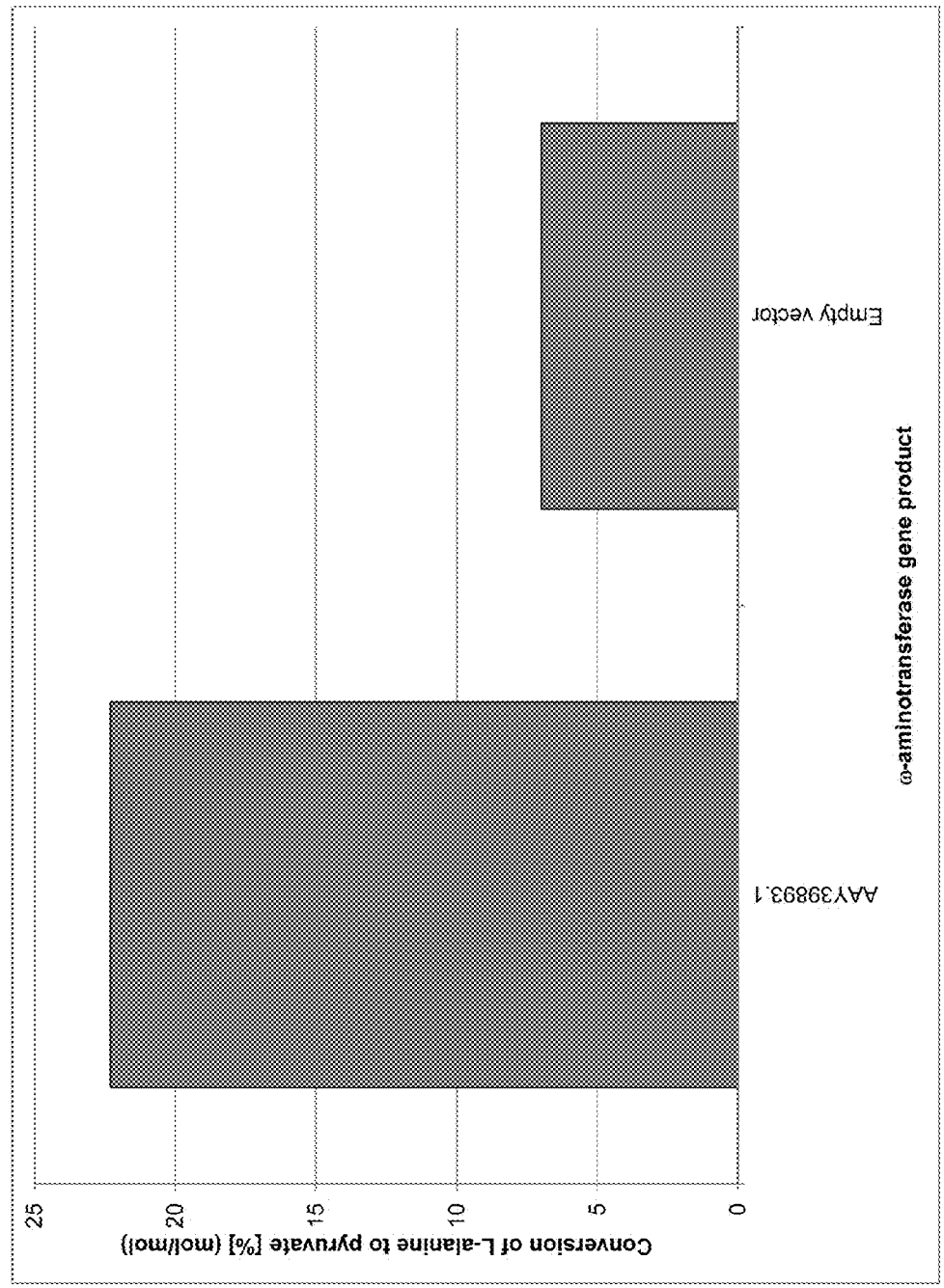
FIG. 19 is a bar graph showing the percent conversion after 4 hours of L-alanine to pyruvate (mol/mol) as a measure of the ω-transaminase activity of one CD-transaminase preparations for converting glutarate semialdehyde to 5-aminopentanoate relative to the empty vector control.

The gene product of SEQ ID NO 10 accepted glutarate semialdehyde as substrate as confirmed against the empty vector control. See FIG. 19. The reversibility of the ω-transaminase activity was confirmed, demonstrating that the ω-transaminases of SEQ ID NO 8, and SEQ ID NO 10 accepted glutarate semialdehyde as substrate and synthesized 5-aminopentanoate as a reaction product.

Example 2

Enzyme Activity of Carboxylate Reductase Using 5-Hydroxypentanoate as Substrate and Forming 5-Hydroxypentanal A nucleotide sequence encoding a His-tag was added to the genes from Mycobacterium marinum, Mycobacterium smegmatis, Segniliparus rugosus, Mycobacterium massiliense, and Segniliparus rotundus that encode the carboxylate reductases of SEQ ID NOs: 2-4, 6 and 7, respectively (GenBank Accession Nos. ACC40567.1, ABK71854.1, EFV11917.1, EIV11143.1, and ADG98140.1, respectively) (see FIG. 10) such that N-terminal HIS tagged carboxylate reductases could be produced. Each of the modified genes was cloned into a pET Duet expression vector alongside a sfp gene encoding a His-tagged phosphopantetheine transferase from Bacillus subtilis, both under control of the T7 promoter. Each expression vector was transformed into a BL21[DE3] E. coli host along with the expression vectors from Example 3. Each resulting recombinant E. coli strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Figure 12:
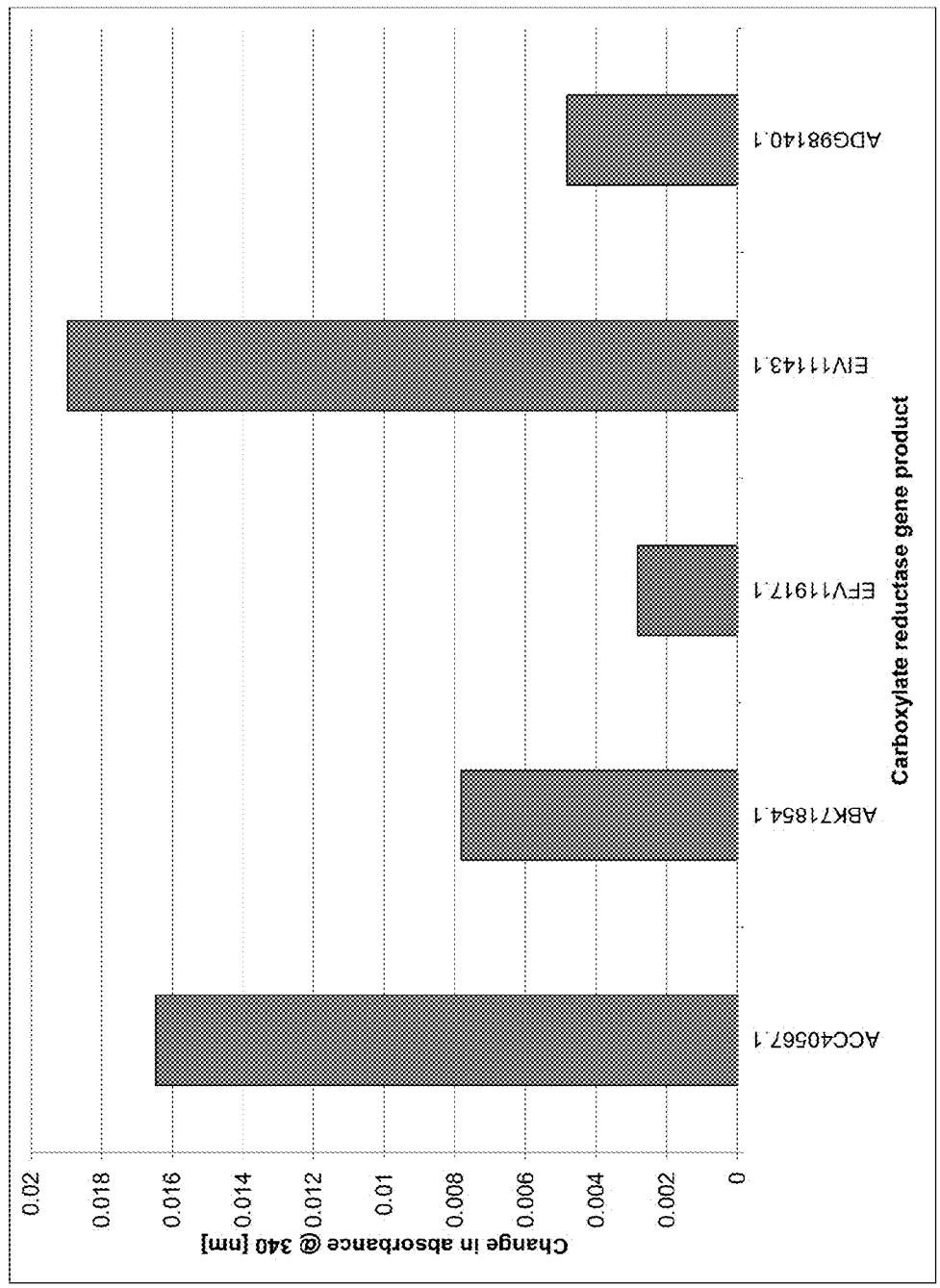
FIG. 12 is a bar graph summarizing the change in absorbance at 340 nm after 20 minutes, which is a measure of the consumption of NADPH and activity of five carboxylate reductase preparations in enzyme only controls (no substrate).

Enzyme activity (i.e., 5-hydroxypentanoate to 5-hydroxypentanal) assays were performed in triplicate in a buffer composed of a final concentration of 50 mM HEPES buffer (pH=7.5), 2 mM 5-hydroxypentanal, 10 mM MgCl$_2$, 1 mM ATP, and 1 mM NADPH. Each enzyme activity assay reaction was initiated by adding purified carboxylate reductase and phosphopantetheine transferase or the empty vector control to the assay buffer containing the 5-hydroxypentanoate and then incubated at room temperature for 20 min. The consumption of NADPH was monitored by absorbance at 340 nm. Each enzyme only control without 5-hydroxypentanoate demonstrated low base line consumption of NADPH. See FIG. 12.

Figure 14:
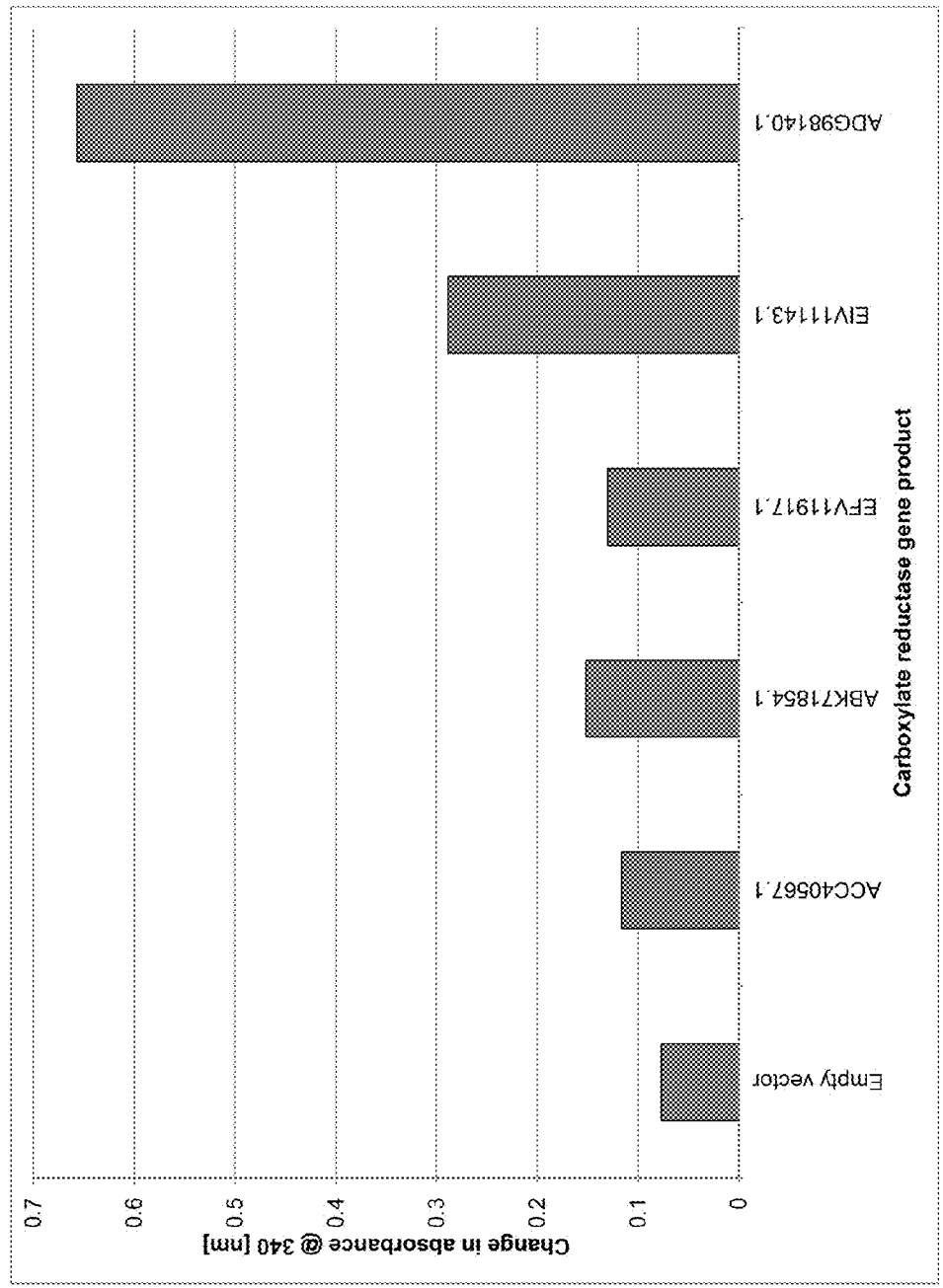
FIG. 14 is a bar graph showing the change in absorbance at 340 nm after 20 minutes, which is a measure of the consumption of NADPH and the activity of five carboxylate reductase preparations for converting 5-hydroxypentanoate to 5-hydroxypentanal relative to the empty vector control.

The gene products of SEQ ID NOs: 2-4, 6 and 7, enhanced by the gene product of sfp, accepted 5-hydroxypentanoate as substrate as confirmed against the empty vector control (see FIG. 14), and synthesized 5-hydroxypentanal.

Example 3

Enzyme Activity of ω-Transaminase for 5-Aminopentanol, Forming 5-Oxopentanol

A nucleotide sequence encoding an N-terminal His-tag was added to the *Chromobacterium violaceum, Pseudomonas aeruginosa, Pseudomonas syringae, Rhodobacter sphaeroide, Escherichia coli* and *Vibrio fluvialis* genes encoding the ω-transaminases of SEQ ID NOs: 8-13, respectively (see FIG. 10) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 5-aminopentanol to 5-oxopentanol) were performed in a buffer composed of a final concentration of 50 mM HEPES buffer (pH=7.5), 10 mM 5-aminopentanol, 10 mM pyruvate, and 100 µM pyridoxyl 5' phosphate. Each enzyme activity assay reaction was initiated by adding cell free extract of the ω-transaminase gene product or the empty vector control to the assay buffer containing the 5-aminopentanol and then incubated at 25° C. for 4 h, with shaking at 250 rpm. The formation of L-alanine was quantified via RP-HPLC.

Each enzyme only control without 5-aminopentanol had low base line conversion of pyruvate to L-alanine See FIG. 17.

Figure 13:
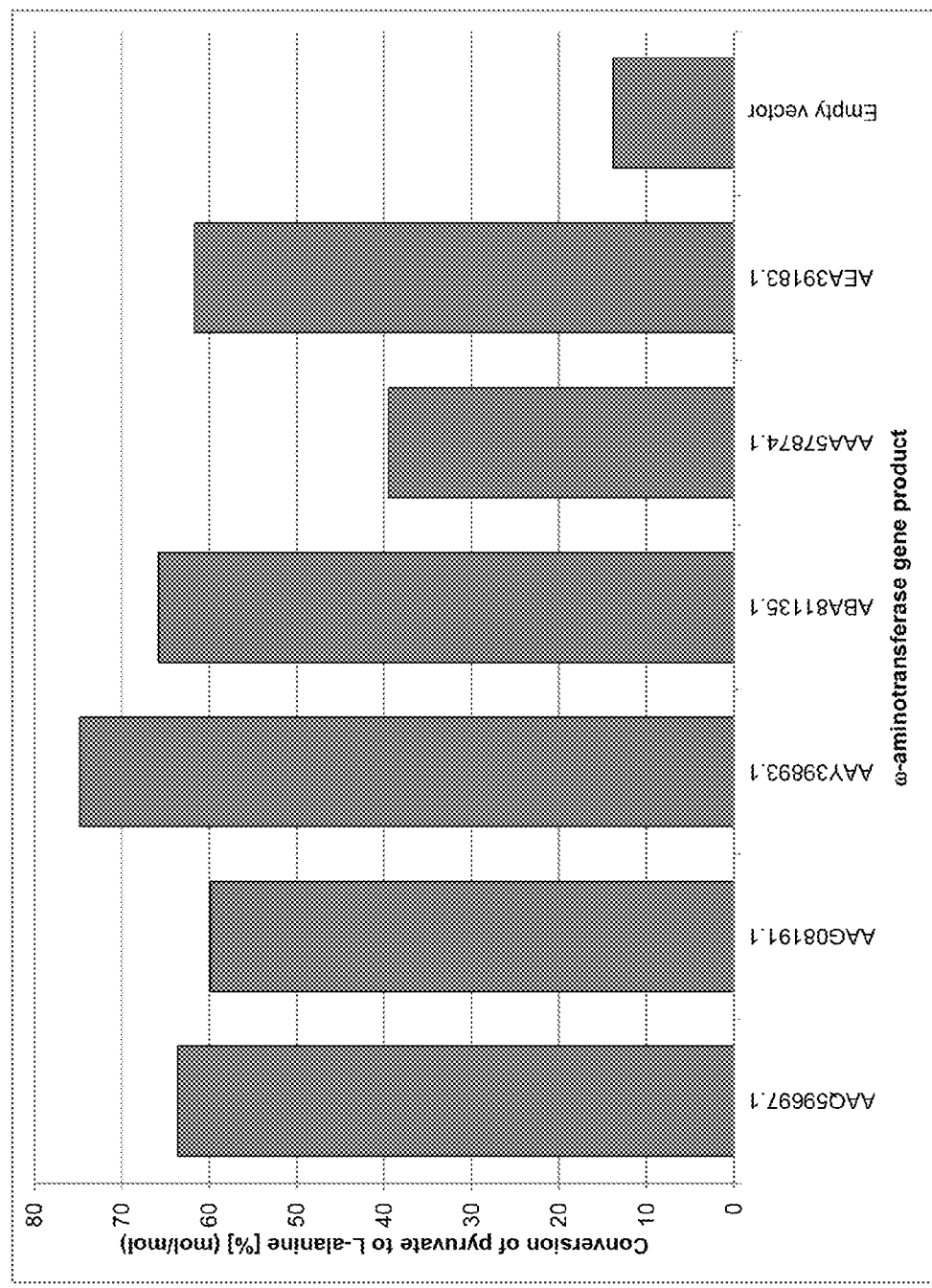
FIG. 13 is a bar graph showing the percent conversion after 4 hours of pyruvate to L-alanine (mol/mol) as a measure of the ω-transaminase activity of six ω-transaminase preparations for converting 5-aminopentanol to 5-oxopentanol relative to the empty vector control.

The gene products of SEQ ID NOs: 8-13 accepted 5-aminopentanol as substrate as confirmed against the empty vector control (see FIG. 13) and synthesized 5-oxopentanol as reaction product. Given the reversibility of the ω-transaminase activity (see Example 1), it can be concluded that the gene products of SEQ ID NOs: 8-13 accept 5-oxopentanol as substrate and form 5-aminopentanol.

Example 4

Enzyme Activity of ω-Transaminase Using Cadaverine as Substrate and Forming 5-Aminopentanal A nucleotide sequence encoding an N-terminal His-tag was added to the Chromobacterium *violaceum, Pseudomonas aeruginosa, Pseudomonas syringae*, and *Escherichia coli* genes encoding the ω-transaminases of SEQ ID NOs: 8-10 and 12, respectively (see FIG. 10) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., cadaverine to 5-aminopentanal) were performed in a buffer composed of a final concentration of 50 mM HEPES buffer (pH=7.5), 10 mM cadaverine, 10 mM pyruvate, and 100 µM pyridoxyl 5' phosphate. Each enzyme activity assay reaction was initiated by adding cell free extract of the ω-transaminase gene product or the empty vector control to the assay buffer containing the cadaverine and then incubated at 25° C. for 4 h, with shaking at 250 rpm. The formation of L-alanine was quantified via RP-HPLC.

Each enzyme only control without cadaverine had low base line conversion of pyruvate to L-alanine See FIG. 17.

Figure 11:
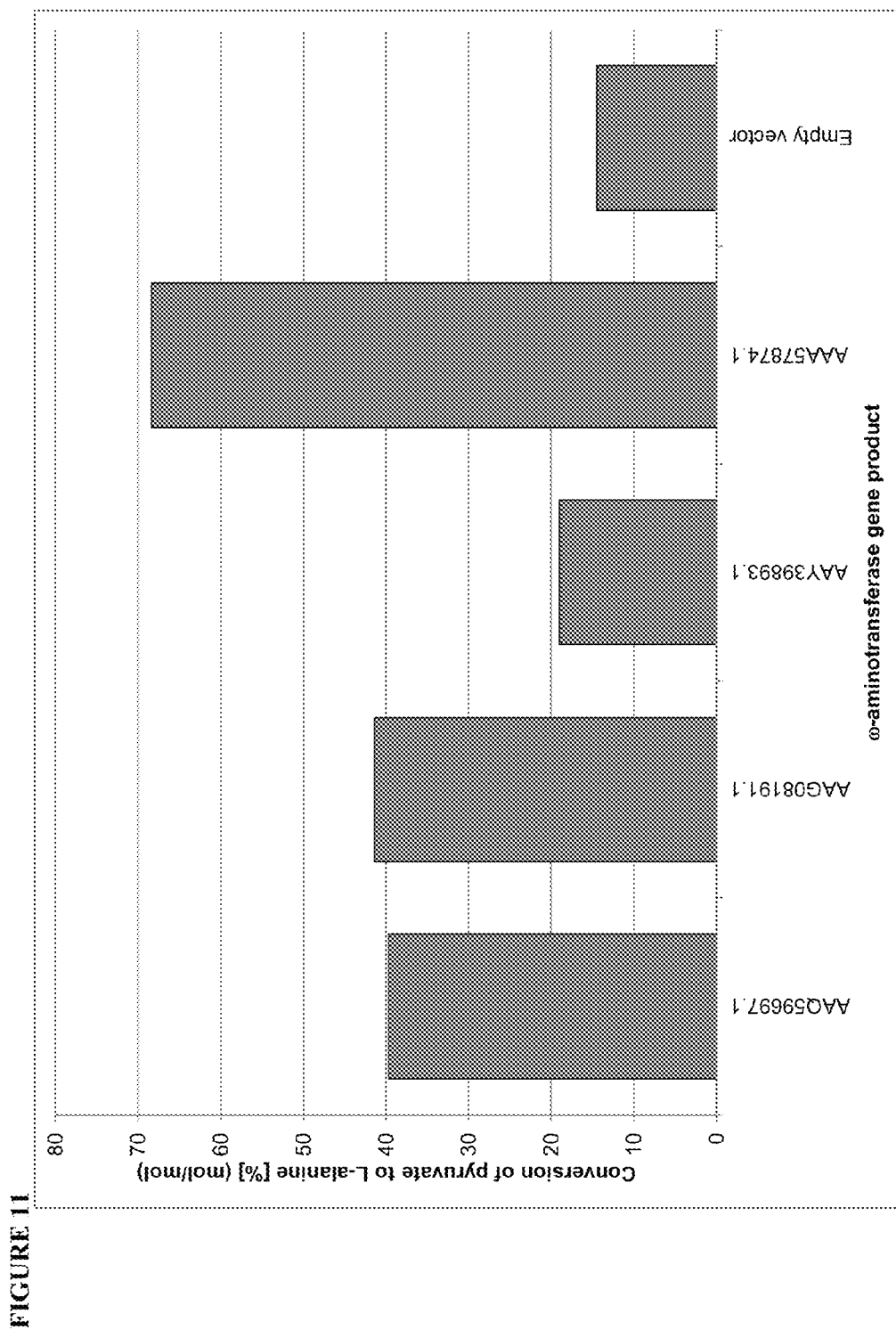
FIG. 11 is a bar graph showing the percent conversion after 4 hours of pyruvate to L-alanine (mol/mol) as a measure of the ω-transaminase activity of four ω-transaminase preparations for converting cadaverine to 5-aminopentanal relative to the empty vector control.

The gene products of SEQ ID NOs: 8-10 and 12 accepted cadaverine as substrate as confirmed against the empty vector control (see FIG. 11) and synthesized 5-aminopentanal as reaction product. Given the reversibility of the ω-transaminase activity (see Example 1), it can be concluded that the gene products of SEQ ID NOs: 8-10 and 12 accept 5-aminopentanal as substrate and form cadaverine.

Example 5

Enzyme Activity of ω-Transaminase Using N5-Acetyl-1,5-Diaminopentane, and Forming N5-Acetyl-5-Aminopentanal The activity of the N-terminal His-tagged ω-transaminases of SEQ ID NOs: 8, 10-13 (see Example 3, and FIG. 10) for converting N5-acetyl-1,5-diaminopentane to N5-acetyl-5-aminopentanal was assayed using a buffer composed of a final concentration of 50 mM HEPES buffer (pH=7.5), 10 mM N5-acetyl-1,5-diaminopentane, 10 mM pyruvate and 100 µM pyridoxyl 5' phosphate. Each enzyme activity assay reaction was initiated by adding a cell free extract of the ω-transaminase or the empty vector control to the assay buffer containing the N5-acetyl-1,5-diaminopentane then incubated at 25° C. for 4 h, with shaking at 250 rpm. The formation of L-alanine was quantified via RP-HPLC.

Each enzyme only control without N5-acetyl-1,5-diaminopentane demonstrated low base line conversion of pyruvate to L-alanine See FIG. 17.

Figure 15:
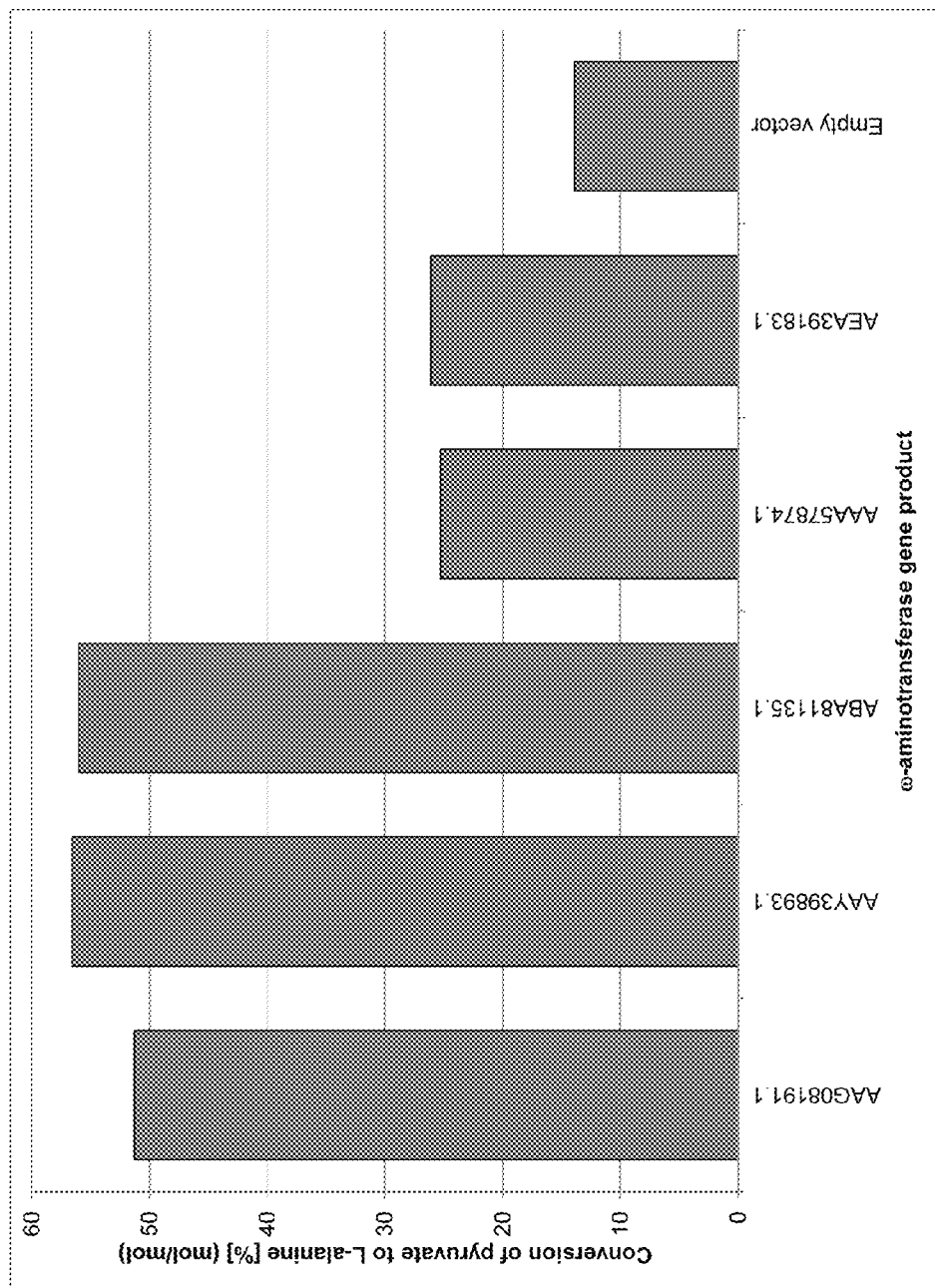
FIG. 15 is a bar graph showing the percent conversion after 4 hours of pyruvate to L-alanine (mol/mol) as a measure of the ω-transaminase activity of five ω-transaminase preparations for converting N5-acetyl-1,5-diaminopentane to N5-acetyl-5-aminopentanal relative to the empty vector control.

The gene product of SEQ ID NOs: 8, 10 accepted N5-acetyl-1,5-diaminopentane as substrate as confirmed against the empty vector control (see FIG. 15) and synthesized N5-acetyl-5-aminopentanal as reaction product.

Given the reversibility of the ω-transaminase activity (see Example 1), the gene products of SEQ ID NOs: 8, 10 accept N5-acetyl-5-aminopentanal as substrate forming N5-acetyl-1,5-diaminopentane.

Example 6

Enzyme Activity of Carboxylate Reductase Using Glutarate Semialdehyde as Substrate and Forming Pentanedial The N-terminal His-tagged carboxylate reductase of SEQ ID NO 7 (see Example 3 and FIG. 10) was assayed using glutarate semialdehyde as substrate. The enzyme activity assay was performed in triplicate in a buffer composed of a final concentration of 50 mM HEPES buffer (pH=7.5), 2 mM glutarate semialdehyde, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the glutarate semialdehyde and then incubated at room temperature for 20 min. The consumption of NADPH was monitored by absorbance at 340 nm. The enzyme only control without glutarate semialdehyde demonstrated low base line consumption of NADPH. See FIG. 12.

Figure 16:
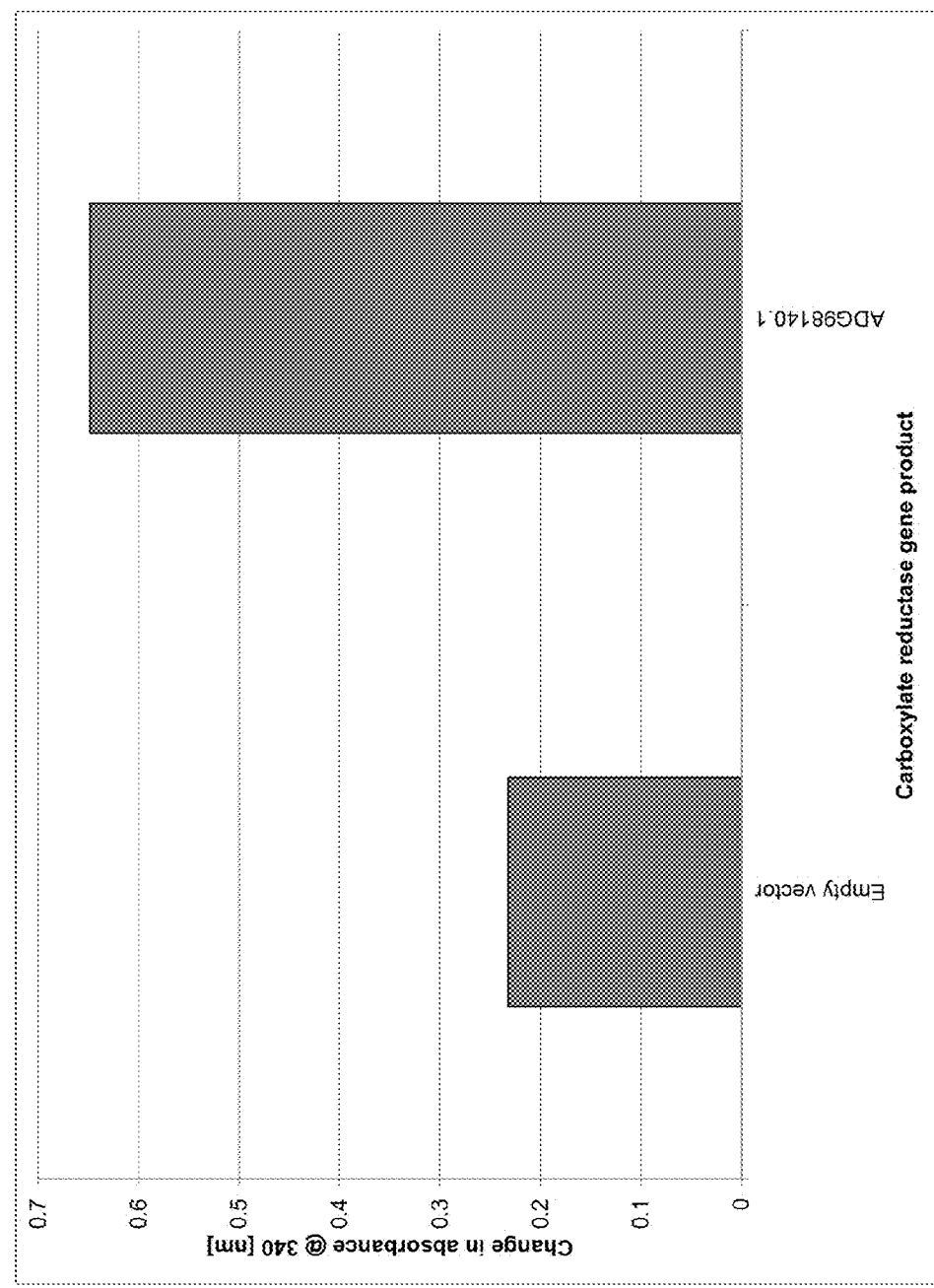
FIG. 16 is a bar graph showing the change in absorbance at 340 nm after 20 minutes, which is a measure of the consumption of NADPH and activity of a carboxylate reductase preparation for converting glutarate semialdehyde to pentanedial relative to the empty vector control.

The gene product of SEQ ID NO 7, enhanced by the gene product of sfp, accepted glutarate semialdehyde as substrate as confirmed against the empty vector control (see FIG. 16) and synthesized pentanedial.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of biosynthesizing a C5 building block selected from the group consisting of glutaric acid, 5-hydroxypentanoic acid, 5-aminopentanoic acid, cadaverine, and 1,5-pentanediol, in a recombinant host, the method comprising:
    (a) (i) enzymatically converting 2-oxo-adipate to 2-amino-adipate using at least one polypeptide having the activity of an alpha-aminotransaminase classified under EC 2.6.1.7 or EC 2.6.1.39, (ii) enzymatically converting 2-oxo-adipate to 5-oxopentanoate using at least one polypeptide having the activity of a 2-oxoacid decarboxylase classified under EC 4.1.1.71, EC 4.1.1.72, EC 4.1.1.43 or EC 4.1.1.74, or (iii) enzymatically converting 2-oxo-adipate to glutaryl-CoA using at least one polypeptide having the activity of a 2-oxoglutarate dehydrogenase complex classified under EC 1.2.4.2, EC 1.8.1.4 and EC 2.3.1.61;
    (b) enzymatically converting the 2-amino-adipate, 5-oxopentanoate, or glutaryl-CoA to the C5 building block, wherein:
    at least one polypeptide having the activity of a thioesterase classified under EC 3.1.2.-, a glutaconate CoA-transferase classified under EC 2.8.3.12, a succinate-CoA ligase classified under EC 6.2.1.5, an aldehyde dehydrogenase classified under EC 1.2.1.-, an acyl-[acp] thioesterase classified under EC 3.1.2.-, a 5-oxopentanoate dehydrogenase classified under EC 1.2.1.-, a 7-oxoheptanoate dehydrogenase classified under EC 1.2.1.-, or a 6-oxohexanoate dehydrogenase classified under EC 1.2.1.63 enzymatically forms a terminal carboxyl group of the C5 building block;
    at least one polypeptide having the activity of an alpha-amino decarboxylase classified under EC 4.1.1.-, a ω-transaminase classified under EC 2.6.1.-, or a deacetylase classified under EC 3.5.1.17 or EC 3.5.1.62 enzymatically forms a terminal amine group of the C5 building block; and/or
    at least one polypeptide having the activity of a 6-hydroxyhexanoate dehydrogenase classified under EC 1.1.1.258, a 5-hydroxypentanoate dehydrogenase classified under EC 1.1.1.-, a 4-hydroxybutyrate dehydratase classified under EC 1.1.1.-, or an alcohol dehydrogenase classified under EC 1.1.1- enzymatically forms a terminal hydroxyl group of the C5 building block.

2. The method of claim 1, wherein the polypeptide having the activity of a 2-oxoacid decarboxylase has at least 90% sequence identity to the amino acid sequence of SEQ ID NO: 1.

3. The method of claim 1, wherein the polypeptide having the activity of a 2-oxoglutarate dehydrogenase complex has at least 90% sequence identity to the amino acid sequence of SEQ ID NO: 16.

4. The method of claim 1, wherein the polypeptide having the activity of a thioesterase activity has at least 90% sequence identity to the amino acid sequence of SEQ ID NO: 17 or 18.

5. The method of claim 1, wherein the polypeptide having the activity of a ω-transaminase activity has at least 90% sequence identity to the amino acid sequence of any one of SEQ ID NOs: 8-13.

6. The method of claim 1, wherein the polypeptide having the activity of an alpha-amino decarboxylase has at least 90% sequence identity to the amino acid sequence of any one of SEQ ID NOs: 19-22.

7. The method of claim 1, wherein a polypeptide having the activity of a carboxylate reductase classified under EC 1.2.99.6 enzymatically forms a terminal aldehyde group as an intermediate in forming the C5 building block.

8. The method of claim 7, wherein the polypeptide having the activity of a carboxylate reductase has at least 90% sequence identity to the amino acid sequence of any one of SEQ ID NOs: 2-7.

9. The method of claim 7, wherein the polypeptide having the activity of a carboxylate reductase is used in combination with a polypeptide having the activity of a phosphopantetheine transferase, wherein the polypeptide having the activity of a phosphopantetheine transferase has at least 90% sequence identity to the amino acid sequence of SEQ ID NO: 14 or 15.

10. The method of claim 1, wherein the 2-oxo-adipate is obtained by enzymatically converting 2-oxo-glutarate to 2-oxo-adipate using at least one polypeptide having an activity selected from the group consisting of a 2-isopropylmalate synthase or homocitrate synthase classified under EC 2.3.3.14 or EC 2.3.3.13, a homoaconitate hydratase or 3-isopropylmalate dehydratase classified under EC 4.2.1.114, EC 4.2.1.36 or EC 4.2.1.33, and a homoisocitrate dehydrogenase or 3-isopropylmalate dehydrogenase classified under EC 1.1.1.85, EC 1.1.1.87 or EC 1.1.1.286.

11. The method of claim 1, wherein glutaryl-CoA is enzymatically converted to glutaric acid using at least one polypeptide having an activity selected from the group consisting of (i) a thioesterase classified under EC 3.1.2.-, (ii) a succinate-CoA-ligase classified under EC 6.2.1.5, (iii) a CoA-transferase classified under EC 2.8.3.-, (iv) an acylating dehydrogenase classified under EC 1.2.1.10 or EC 1.2.1.76 and an aldehyde dehydrogenase classified under EC 1.2.1.-, and (v) an aldehyde dehydrogenase classified under EC 1.2.1.3.

12. The method of claim 1, wherein 2-amino-adipate is enzymatically converted to 5-aminopentanoic acid using a polypeptide having the activity of an alpha-amino decarboxylase classified under EC 4.1.1.-.

13. The method of claim 1, wherein 5-oxopentanoic acid is enzymatically converted to 5-hydroxypentanoic acid using at least one polypeptide having an activity selected from the group consisting of a 5-hydroxypentanoate dehydrogenase classified under EC 1.1.1.-, a 6-hydroxyhexanoate dehydrogenase classified under EC 1.1.1.258, and an alcohol dehydrogenase classified under EC 1.1.1.-.

14. The method of claim 1, wherein 5-oxopentanoic acid is enzymatically converted to cadaverine using at least one polypeptide having an activity selected from the group consisting of a carboxylate reductase classified under EC 1.2.99.6 and a ω-transaminase classified under EC 2.6.1.-.

15. The method of claim 1, wherein the C5 building block is glutaric acid and the method further comprises enzymatically converting glutaric acid to 5-aminopentanoic acid using at least one polypeptide having an activity selected from the group consisting of a carboxylate reductase classified under EC 1.2.99.6 and a ω-transaminase classified under EC 2.6.1.-.

16. The method of claim 1, wherein the C5 building block is glutaric acid and the method further comprises enzymatically converting glutaric acid to 5-hydroxypentainoic acid using at least one polypeptide having an activity selected from the group consisting of a carboxylate reductase classified under EC 1.2.99.6 and an alcohol dehydrogenase classified under EC 1.1.1.-.

17. The method of claim 1, wherein the C5 building block is 5-aminopentanoic acid and the method further comprises enzymatically converting 5-aminopentanoic acid to cadaverine using at least one polypeptide having an activity selected from the group consisting of a carboxylate reductase classified under EC 1.2.99.6 and a ω-transaminase classified under EC 2.6.1.-.

18. The method of claim 1, wherein the C5 building block is 5-hydroxypentanoic acid and the method further comprises enzymatically converting 5-hydroxypentanoic acid to cadaverine using at least one polypeptide having an activity selected from the group consisting of a carboxylate reductase classified under EC 1.2.99.6, a ω-transaminase classified under EC 2.6.1.-, and an alcohol dehydrogenase classified under EC 1.1.1.-.

19. The method of claim 1, wherein the C5 building block is 5-hydroxypentanoic acid and the method further comprises enzymatically converting the 5-hydroxypentanoic acid to 1,5-pentanediol using at least one polypeptide having an activity selected from the group consisting of a carboxylate reductase classified under EC 1.2.99.6 and an alcohol dehydrogenase classified under EC 1.1.1.-.

20. The method of claim 1, wherein the C5 building block is 5-aminopentanoic acid and the method further comprises enzymatically converting the 5-aminopentanoic acid to cadaverine using at least one polypeptide having an activity selected from the group consisting of an N-acetyltransferase classified under EC 2.3.1.32, a carboxylate reductase classified under EC 1.2.99.6, a ω-transaminase classified under EC 2.6.1.-, and a deacetylase classified under EC 3.5.1.17 or EC 3.5.1.62.

21. A method for producing a bioderived 5-carbon compound comprising performing the method according to claim 1 under conditions and for a sufficient period of time to produce the bioderived 5-carbon compound, wherein, optionally, the bioderived 5-carbon compound is selected from the group consisting of glutaric acid, 5-hydroxypentanoic acid, 5-aminopentanoic acid, cadaverine, and 1,5-pentanediol, and combinations thereof.

* * * * *